(12) United States Patent
Bolognesi et al.

(10) Patent No.: US 7,252,958 B2
(45) Date of Patent: Aug. 7, 2007

(54) MODULATION OF TETRASPANIN FUNCTION

(75) Inventors: Martino Bolognesi, Torre d'Isola (IT); Guido Grandi, Segrate (IT)

(73) Assignee: Novartis Vaccines and Diagnostics S.R.L., Siena (IT)

(*) Notice: Subject to any disclaimer, the term of this patent is extended or adjusted under 35 U.S.C. 154(b) by 332 days.

(21) Appl. No.: 10/312,491

(22) PCT Filed: Jul. 3, 2001

(86) PCT No.: PCT/IB01/01458

§ 371 (c)(1),
(2), (4) Date: May 1, 2003

(87) PCT Pub. No.: WO02/02632

PCT Pub. Date: Jan. 10, 2002

(65) Prior Publication Data

US 2004/0023297 A1    Feb. 5, 2004

(30) Foreign Application Priority Data

Jul. 3, 2000  (GB) ................................ 0016362.6

(51) Int. Cl.
*G01N 33/53* (2006.01)
*C07K 14/00* (2006.01)
*C12P 21/06* (2006.01)

(52) U.S. Cl. ....................... 435/7.2; 530/350; 435/69.1

(58) Field of Classification Search .................... None
See application file for complete search history.

(56) References Cited

FOREIGN PATENT DOCUMENTS

WO    WO 0070076    11/2000

OTHER PUBLICATIONS

Levy, S. et al. "CD81 (TAPA-1): A molecule involved in signal transduction and cell adhesion in the immune system." Annu. Rev. Immunol. 1998 16: 89-109.*
Wells, Biochemistry 29:8509-8517, 1990.*
Ngo et al. Computational complexity, protein structure prediction, and the Levinthal paradox. In Merz and Le Grand (Eds.) The Protein Folding Problem and Tertiary Structure Prediction. Birkhauser:Boston, pp. 492-495, 1994.*
Bork et al., Trends in Genetics. 12(10):425-427, 1996.*
Skolnick et al., 18(1):34-39, 2000.*
Doerks et al., Trends in Genetics 14(6):248-250 1998.*
Smith et al., Nature Biotech. 15:1222-1223, 1997.*
Goldberg et al., "Cysteine residues of Photoreceptor Peripherin/RDS: Role in Subunit Assembly and Autosomal Dominant Retinitis Pigmentosa," Biochemistry, 37(2):680-685 (1998).
Maecker et al., "The Tetraspanin Super Family: Molecular Facilitators," FASEB Journal, Fed. of American Soc. For Experimental Biology, Bethesda, MD, US, 11(6):428-442 (1997).
Kitadokoro Kengo et al., "Estracellular Domain 3D Structure: Insight into the Tetraspanin Superfamily Structural Motifs," European Molecular Biology Oragnization Journal, 20(1-2): 12-18 (2001)

* cited by examiner

*Primary Examiner*—Gary Nickol
*Assistant Examiner*—Gyan Chandra
(74) *Attorney, Agent, or Firm*—Marcella Lillis; Roberta L. Robins; Alisa A. Harbin

(57) ABSTRACT

Tetraspanins have been found to dimerise. Methods for inhibiting or promoting the dimerisation of tetraspanins are provided, which may involve protein engineering of the tetraspanins themselves, or may rely on other molecules.

14 Claims, 6 Drawing Sheets

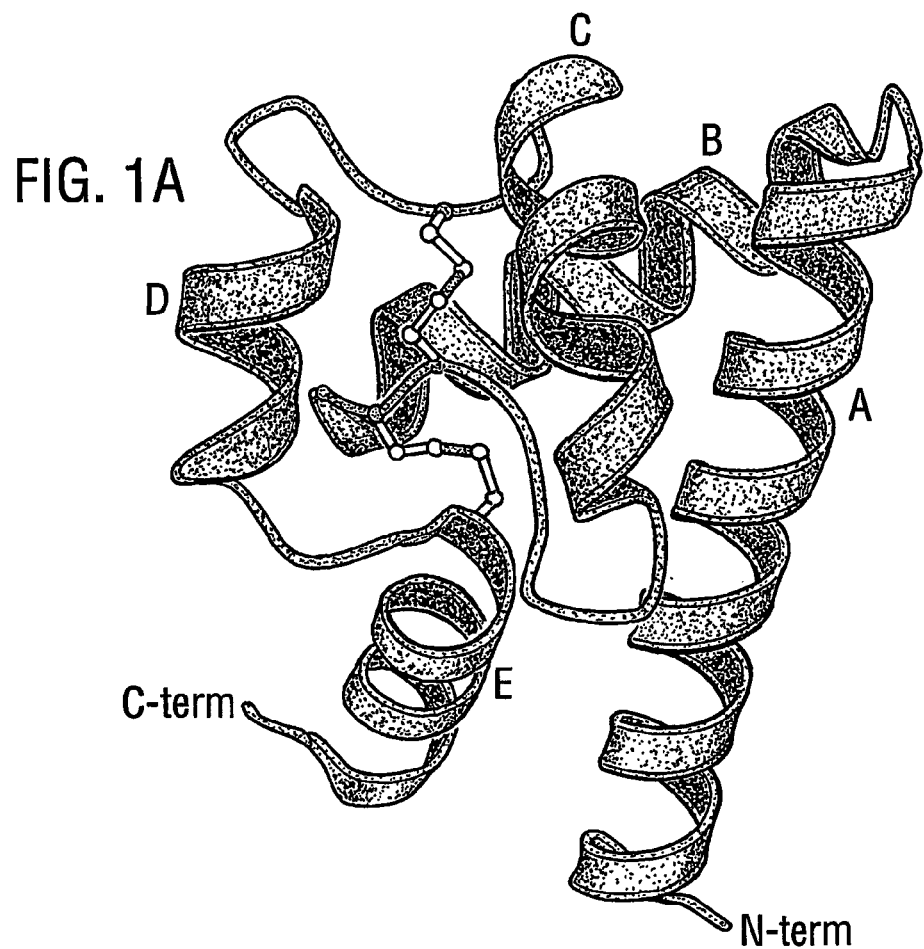

SEQUENCE LISTING

<160> NUMBER OF SEQ ID NOS: 15

<210> SEQ ID NO 1
<211> LENGTH: 236
<212> TYPE: PRT
<213> ORGANISM: Homo sapiens
<220> FEATURE:
<221> NAME/KEY: Human CD81
<223> OTHER INFORMATION: CD81 Full Sequence

<400> SEQUENCE: 1

Met Gly Val Glu Gly Cys Thr Lys Cys Ile Lys Tyr Leu Leu Phe Val
1               5                   10                  15

```
Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Ala Asn Asn Ala Lys
    130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235

<210> SEQ ID NO 2
<211> LENGTH: 89
<212> TYPE: PRT
<213> ORGANISM: Homo sapiens
<220> FEATURE:
<221> NAME/KEY: CD81 LEL
<223> OTHER INFORMATION: Large Extracellular Loop

<400> SEQUENCE: 2

Phe Val Asn Lys Asp Gln Ile Ala Lys Asp Val Lys Gln Phe Tyr Asp
1               5                   10                  15

Gln Ala Leu Gln Gln Ala Val Val Asp Asp Ala Asn Asn Ala Lys
            20                  25                  30

Ala Val Val Lys Thr Phe His Glu Thr Leu Asp Cys Cys Gly Ser Ser
        35                  40                  45

Thr Leu Thr Ala Leu Thr Thr Ser Val Leu Lys Asn Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85

<210> SEQ ID NO 3
<211> LENGTH: 89
<212> TYPE: PRT
<213> ORGANISM: Chlorocebus aethiops
<220> FEATURE:
<221> NAME/KEY: CD81 LEL
```

-continued

<223> OTHER INFORMATION: Green Monkey CD81 LEL

<400> SEQUENCE: 3

Phe Val Asn Lys Asp Gln Ile Ala Lys Asp Val Lys Gln Phe Tyr Asp
1               5                   10                  15

Gln Ala Leu Gln Gln Ala Val Val Asp Asp Ala Asn Asn Ala Lys
            20                  25                  30

Ala Val Val Lys Thr Phe His Glu Thr Val Asp Cys Cys Gly Ser Ser
            35                  40                  45

Thr Leu Ala Ala Leu Thr Thr Ser Val Leu Lys Asn Asn Leu Cys Pro
    50                  55                  60

Ser Gly Ser Asn Ile Ile Ser Asn Leu Leu Lys Asp Cys His Gln
65                  70                  75                  80

Lys Ile Asp Asp Phe Phe Ser Gly Lys
            85

<210> SEQ ID NO 4
<211> LENGTH: 89
<212> TYPE: PRT
<213> ORGANISM: Saguinus oedipus
<220> FEATURE:
<221> NAME/KEY: CD81 LEL
<223> OTHER INFORMATION: Tamarin CD81 LEL

<400> SEQUENCE: 4

Phe Val Asn Lys Asp Gln Ile Ala Lys Asp Val Lys Gln Phe Tyr Asp
1               5                   10                  15

Gln Ala Leu Gln Gln Ala Val Val Asp Asp Ala Asn Asn Ala Lys
            20                  25                  30

Ala Val Val Lys Thr Phe His Glu Thr Leu Asn Cys Cys Gly Ser Ser
            35                  40                  45

Thr Leu Ser Ala Leu Thr Thr Ser Met Leu Lys Asn Asn Leu Cys Pro
    50                  55                  60

Ser Gly Ser Ser Ile Ile Ser Asn Leu Phe Lys Glu Asp Cys His Gln
65                  70                  75                  80

Lys Ile Asp Glu Leu Phe Ser Gly Lys
            85

<210> SEQ ID NO 5
<211> LENGTH: 89
<212> TYPE: PRT
<213> ORGANISM: Mesocricetus auratus
<220> FEATURE:
<221> NAME/KEY: CD81 LEL
<223> OTHER INFORMATION: Hamster CD81 LEL

<400> SEQUENCE: 5

Phe Val Asn Lys Asp Gln Ile Ala Lys Asp Val Lys Gln Phe Tyr Asp
1               5                   10                  15

Gln Ala Leu Gln Gln Ala Val Val Asp Asp Ala Asn Asn Ala Lys
            20                  25                  30

Ala Val Val Lys Thr Phe His Glu Thr Leu Asn Cys Cys Gly Ser Asn
            35                  40                  45

Ala Leu Thr Ala Leu Thr Thr Ser Val Leu Lys Asn Ser Leu Cys Pro
    50                  55                  60

Ser Gly Thr Asn Ile Phe Asn Ser Leu Met Lys Glu Asp Cys His Gln
65                  70                  75                  80

Lys Ile Asp Glu Leu Phe Ser Gly Lys
            85

```
<210> SEQ ID NO 6
<211> LENGTH: 89
<212> TYPE: PRT
<213> ORGANISM: Rattus norvegicus
<220> FEATURE:
<221> NAME/KEY: CD81 LEL
<223> OTHER INFORMATION: Rat CD81 LEL

<400> SEQUENCE: 6

Phe Val Asn Lys Asp Gln Ile Ala Lys Asp Val Lys Gln Phe Tyr Asp
1               5                   10                  15

Gln Ala Leu Gln Gln Ala Val Met Asp Asp Ala Asn Asn Ala Lys
            20                  25                  30

Ala Val Val Lys Thr Phe His Glu Thr Leu Asn Cys Cys Gly Ser Asn
        35                  40                  45

Thr Leu Thr Thr Leu Thr Thr Ala Val Leu Arg Asn Ser Leu Cys Pro
    50                  55                  60

Ser Ser Ser Asn Ser Phe Thr Gln Leu Leu Lys Glu Asp Cys His Gln
65                  70                  75                  80

Lys Ile Asp Glu Leu Phe Ser Gly Lys
                85

<210> SEQ ID NO 7
<211> LENGTH: 89
<212> TYPE: PRT
<213> ORGANISM: Mus musculus
<220> FEATURE:
<221> NAME/KEY: CD81 LEL
<223> OTHER INFORMATION: Mouse CD81 LEL

<400> SEQUENCE: 7

Phe Val Asn Lys Asp Gln Ile Ala Lys Asp Val Lys Gln Phe Tyr Asp
1               5                   10                  15

Gln Ala Leu Gln Gln Ala Val Met Asp Asp Ala Asn Asn Ala Lys
            20                  25                  30

Ala Val Val Lys Thr Phe His Glu Thr Leu Asn Cys Cys Gly Ser Asn
        35                  40                  45

Ala Leu Thr Thr Leu Thr Thr Thr Ile Leu Arg Asn Thr Leu Cys Pro
    50                  55                  60

Ser Gly Gly Asn Ile Leu Thr Pro Leu Leu Gln Gln Asp Cys His Gln
65                  70                  75                  80

Lys Ile Asp Glu Leu Phe Ser Gly Lys
                85

<210> SEQ ID NO 8
<211> LENGTH: 82
<212> TYPE: PRT
<213> ORGANISM: Homo sapiens
<220> FEATURE:
<221> NAME/KEY: CD9

<400> SEQUENCE: 8

Tyr Ser His Lys Asp Glu Val Ile Lys Glu Val Gln Glu Phe Tyr Lys
1               5                   10                  15

Asp Thr Tyr Asn Lys Leu Lys Thr Lys Asp Glu Pro Gln Arg Glu Thr
            20                  25                  30

Leu Lys Ala Ile His Tyr Ala Leu Asn Cys Cys Gly Leu Ala Gly Gly
        35                  40                  45

Val Glu Gln Phe Ile Ser Asp Ile Cys Pro Lys Lys Asp Val Leu Glu
```

-continued

```
            50                  55                  60
Thr Phe Thr Val Lys Ser Cys Pro Asp Ala Ile Lys Glu Val Phe Asp
 65                  70                  75                  80

Asn Lys

<210> SEQ ID NO 9
<211> LENGTH: 77
<212> TYPE: PRT
<213> ORGANISM: Homo sapiens
<220> FEATURE:
<221> NAME/KEY: TSPAN2

<400> SEQUENCE: 9

Phe Ile Gly Lys Gly Val Ala Ile Arg His Val Gln Thr Met Tyr Glu
 1               5                  10                  15

Glu Ala Tyr Asn Asp Tyr Leu Lys Asp Arg Gly Lys Gly Asn Gly Thr
                20                  25                  30

Leu Ile Thr Phe Pro Leu Gln His Phe Gln Cys Cys Gly Lys Glu Ser
            35                  40                  45

Ser Glu Gln Val Gln Pro Thr Cys Pro Lys Glu Leu Leu Arg His Lys
        50                  55                  60

Asn Cys Ile Asp Glu Ile Glu Thr Ile Ile Ser Val Lys
 65                  70                  75

<210> SEQ ID NO 10
<211> LENGTH: 78
<212> TYPE: PRT
<213> ORGANISM: Mus musculus
<220> FEATURE:
<221> NAME/KEY: CD53

<400> SEQUENCE: 10

Phe Val Tyr Glu Gln Lys Leu Asn Thr Leu Val Ala Glu Gly Leu Asn
 1               5                  10                  15

Asp Ser Ile Gln His Tyr His Ser Asp Asn Ser Thr Met Lys Ala Trp
                20                  25                  30

Asp Phe Ile Gln Thr Gln Leu Gln Cys Cys Gly Val Asn Gly Ser Ser
            35                  40                  45

Asp Trp Thr Ser Gly Pro Pro Ser Ser Cys Pro Ser Gly Ala Asp Val
        50                  55                  60

Gln Gly Cys Tyr Asn Lys Ala Lys Ser Trp Phe His Ser Asn
 65                  70                  75

<210> SEQ ID NO 11
<211> LENGTH: 88
<212> TYPE: PRT
<213> ORGANISM: Homo sapiens
<220> FEATURE:
<221> NAME/KEY: CD82

<400> SEQUENCE: 11

Tyr Phe Asn Met Gly Lys Leu Lys Gln Glu Met Gly Gly Ile Val Thr
 1               5                  10                  15

Glu Leu Ile Arg Asp Tyr Asn Ser Ser Arg Glu Asp Ser Leu Gln Asp
                20                  25                  30

Ala Trp Asp Tyr Val Gln Ala Gln Val Lys Cys Cys Gly Trp Val Ser
            35                  40                  45

Phe Tyr Asn Trp Thr Asp Asn Ala Glu Tyr Pro Cys Ser Cys Glu Val
        50                  55                  60
```

-continued

Lys Gly Glu Glu Asp Asn Ser Val Tyr Gln Glu Gly Cys Met Glu Lys
65                  70                  75                  80

Val Gln Ala Trp Leu Gln Glu Asn
                85

<210> SEQ ID NO 12
<211> LENGTH: 86
<212> TYPE: PRT
<213> ORGANISM: Homo sapiens
<220> FEATURE:
<221> NAME/KEY: CD63

<400> SEQUENCE: 12

Tyr Val Phe Arg Asp Lys Val Met Ser Glu Phe Asn Asn Asn Phe Arg
1               5                   10                  15

Gln Gln Met Glu Asn Tyr Pro Lys Asn Asn His Thr Ala Ser Ile Leu
                20                  25                  30

Asp Arg Met Gln Ala Asp Phe Lys Cys Cys Gly Ala Ala Asn Tyr Thr
            35                  40                  45

Asp Ser Met Ser Lys Asn Arg Val Pro Asp Ser Cys Cys Cys Gly Ile
        50                  55                  60

Asn Phe Asn Glu Lys Ile His Lys Glu Gly Cys Val Glu Lys Ile Gly
65                  70                  75                  80

Gly Trp Leu Arg Lys Asn
                85

<210> SEQ ID NO 13
<211> LENGTH: 86
<212> TYPE: PRT
<213> ORGANISM: Homo sapiens
<220> FEATURE:
<221> NAME/KEY: TALLA1

<400> SEQUENCE: 13

Phe Val Phe Arg His Glu Ile Lys Asp Thr Phe Leu Arg Thr Tyr Thr
1               5                   10                  15

Asp Ala Met Gln Thr Tyr Asn Gly Asn Asp Glu Arg Ser Arg Ala Val
                20                  25                  30

Asp His Val Gln Arg Ser Leu Ser Cys Cys Gly Val Gln Asn Tyr Thr
            35                  40                  45

Asn Trp Ser Thr Ser His Gly Ile Pro Pro Ser Cys Cys Cys Asn Pro
        50                  55                  60

Gln Asp Leu His Asn Leu Thr Gln Lys Gly Cys Tyr Asp Leu Val Thr
65                  70                  75                  80

Ser Phe Met Glu Thr Asn
                85

<210> SEQ ID NO 14
<211> LENGTH: 86
<212> TYPE: PRT
<213> ORGANISM: Homo sapiens
<220> FEATURE:
<221> NAME/KEY: NET4

<400> SEQUENCE: 14

Phe Val Phe Lys Asp Trp Ile Lys Asp Gln Leu Tyr Phe Phe Ile Asn
1               5                   10                  15

Asn Asn Ile Arg Ala Tyr Arg Asp Asp Ile Asp Leu Gln Asn Leu Ile
                20                  25                  30

Asp Phe Thr Gln Glu Tyr Trp Gln Cys Cys Gly Ala Thr Asp Ser Asn

```
                     35                  40                  45
Ala Ser Arg Glu Arg Cys Gly Val Pro Phe Ser Cys Cys Thr Lys Asp
    50                  55                  60

Pro Ala Glu Asp Val Ile Tyr Thr Lys Gly Cys Val Pro Gln Phe Glu
65                  70                  75                  80

Lys Trp Leu Gln Asp Asn
                85

<210> SEQ ID NO 15
<211> LENGTH: 89
<212> TYPE: PRT
<213> ORGANISM: Artificial Sequence
<220> FEATURE:
<223> OTHER INFORMATION: Chimpanzee CD81 LEL

<400> SEQUENCE: 15

Phe Val Asn Lys Asp Gln Ile Ala Lys Asp Val Lys Gln Phe Tyr Asp
1               5                   10                  15

Gln Ala Leu Gln Gln Ala Val Val Asp Asp Ala Asn Asn Ala Lys
                20                  25                  30

Ala Val Val Lys Thr Phe His Glu Thr Leu Asp Cys Cys Gly Ser Ser
                35                  40                  45

Thr Leu Thr Ala Leu Thr Thr Ser Val Leu Lys Asn Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Phe Phe Ser Gly Lys
                85
```

MODULATION OF TETRASPANIN FUNCTION

TECHNICAL FIELD

This invention is in the field of tetraspanins, more particularly the modulation of their function.

BACKGROUND ART

Since its discovery in 1990, the tetraspanin superfamily (also known as TM4, 4TM, TM4SF, and tetraspans) has grown to include around 20 proteins [refs 1 & 2]. All of the members are cell-surface proteins that span the membrane four times, forming two extracellular loops. Some are found in organisms as primitive as schistosomes and nematodes.

The tetraspanins are diverse. Some are found in virtually all tissues (CD81, CD82, CD9, CD63), whereas others are highly restricted, such as CD37 (B cells) or CD53 (lymphoid and myeloid cells). Functionally, they are involved in diverse processes such as cell activation and proliferation, adhesion and motility, differentiation, and cancer. Many tetraspanins are being discovered as tumor-associated antigens, related to tumor growth and proliferation [2, 3]. This is in line with an emerging body of evidence indicating that tetraspanins are key players in the regulation of cell adhesion, proliferation, activation and migration. It has been proposed that all these functions may relate to the proteins' ability to act as 'molecular facilitators' which group specific cell-surface proteins and thus increase the formation and stability of functional signalling complexes.

DISCLOSURE OF THE INVENTION

The invention is based on the surprising discovery that CD81, a prototype tetraspanin, forms stable dimers. Modulation of the ability of tetraspanins to dimerise offers the ability to modulate their functional activity. Thus the invention provides, generally, methods for inhibiting or promoting the dimerisation of tetraspanins. These methods may involve protein engineering of the tetraspanins themselves, or may rely on other molecules.

Protein Engineering

The large extracellular loop (LEL; amino acids 113–201) (SEQ ID NO: 2) of human CD81 (SEQ ID NO: 1) has been shown to dimerise. There are two main regions of interface between monomers, involving the following amino acid residues:

(i) The first interface is between antiparallel α-helices and involves primarily residues Val114, Ile119, Val123, Gln125, Phe126 and Gln129. Gln129 in one monomer forms a hydrogen bond with Val114 in the other. Solvent-mediated interactions between exposed polar side chains are also involved at the rim of the contact region.

(ii) The second interface region includes residues Asn142, Val146, Thr149, Phe150, Thr153 and Leu154 in one monomer which contact Leu197, Phe198, Ser199 and Gly200 in the other monomer. Ser199 in one monomer forms a hydrogen bond with Asn142 in the other.

Mutation of these residues thus allows the dimerisation ability of CD81 to be modulated.

The corresponding amino acids in other tetraspanins can be similarly mutated. As the tetraspanins are highly homologous, an amino acid alignment allows the simple determination of the precise amino acids in other tetraspanins that correspond to those of CD81. One such alignment is shown in FIG. 2 herein, with residues corresponding to the CD81 contact residues highlighted. As an example, CD81 residue 114 can be seen to correspond to the following residues:

| Protein | Accession n° | CD81 residue 114 |
| --- | --- | --- |
| Human CD81 | NP_004347 | 114 |
| Human CD9 | NP_001760 | 112 |
| Human TSPAN2 | NP_005716 | 111 |
| Murine CD53 | NP_031677 | 105 |
| Human CD82 | NP_002222 | 108 |
| Human CD63 | NP_001771 | 106 |
| Human TALLA-1 | AAF44123 | 84 |
| Human NET4 | AAC17120 | 114 |

Thus the invention provides a method for modulating the ability of a tetraspanin protein to form dimers with the wild-type tetraspanin, comprising the steps of mutating at least one of the amino acids corresponding to human CD81 residues 114, 119, 123, 125, 126, 129, 142, 146, 149, 150, 153, 154, 197, 198, 199 and 200.

The tetraspanin is preferably human CD81 (SEQ ID NO: 1), which has the amino acid sequence:

```
  1 MGVEGCTKCI KYLLFVFNFV FWLAGGVILG VALWLRHDPQ TTNLLYLELG DKPAPNTFYV

61 GIYILTAVGA VMMFVGFLGC YGAIQESQCL LGTFFTCLVI LFACEVAAGI WGFVNKDQIA

121 KDVKQFYDQA LQQAVVDDDA NNAKAVVKTF HETLDCCGSS TLTALTTSVL KNNLCPSGSN

181 IISNLFKEDC HQKIDDLFSG KLYLIGIAAI VVAVIMIFEM ILSMVLCCGI RNSSVY
```

As the wild-type interface is largely non-polar (70% of 986 Å² in CD81), where it is desired to inhibit dimerisation, it is preferred that a non-polar residues should be replaced by polar residues (e.g. Ser, Thr, Tyr, Cys, Asn, Gln, Asp, Glu, Lys, Arg, His). Conversely, where promotion of dimerisation is desired, non-polar residues should be replaced by other non-polar residues (e.g. Ala, Gly, Val, Leu, Ile, Met, Pro, Trp, Phe).

The invention also provides (i) a mutant tetraspanin protein which, compared with the wild-type protein, has an increased ability to form a dimer with the wild-type protein, and (ii) a mutant tetraspanin protein which, compared with the wild-type protein, has a decreased ability to form a dimer with the wild-type protein.

The mutant tetraspanin preferably has a non-wild-type amino acid at one or more residues corresponding to human CD81 (SEQ ID NO: 1) residues 114, 119, 123, 125, 126, 129, 142, 146, 149, 150, 153, 154, 197, 198, 199 and 200.

The mutant tetraspanin is preferably a mutant human CD81.

The invention also provides a tetraspanin dimer, wherein one or both of the monomers is a mutant tetraspanin according to the invention. Where both monomers are mutants, they may carry the same or different mutations.

Compounds which Inhibit Dimerisation

As an alternative to modulating dimerisation capability by changing a tetraspanin's amino acid sequence, compounds which interact with the hydrophobic monomer:monomer interface and thereby inhibit or promote the interaction, can be used.

A variety of methods can be used to identify compounds which can bind to the interface, such as structure-based drug design methods or screening methods.

Structure-based Drug Design Techniques

Structure-based drug design techniques can be applied to structural representations of tetraspanins in order to identify compounds that interact at the monomer:monomer interface regions and block dimerisation. A variety of suitable techniques [e.g. ref. 4] are available to the skilled person.

The invention provides a computer-based method for identifying a ligand which can interact with a tetraspanin to promote or inhibit its ability to dimerise, comprising the steps of: (a) providing a 3D structural representation of the tetraspanin in a storage medium on a computer; and (b) using the computer to apply structure-based drug design techniques to the structural representation.

Software packages for implementing molecular modelling techniques for use in structure-based drug design include SYBYL [5], AMBER [6], CERIUS$^2$ [7], INSIGHT II [7], CATALYST [7], QUANTA [7], HYPERCHEM [8], CHEMSITE [9] etc.

This software can be used to determine binding surfaces of the tetraspanins in order to reveal features such as van der Waals contacts, electrostatic interactions, and/or hydrogen bonding opportunities. These binding surfaces may be used as follows:

Docking

Docking aligns the 3D structures of two or more molecules to predict the conformation of a complex formed from the molecules [e.g. ref 10]. According to the present invention, molecules are docked with a tetraspanin structure to assess their ability to interact with the tetraspanin.

Docking can be accomplished by either geometric matching of the ligand and its receptor or by minimising the energy of interaction. Geometric matching algorithms are preferred because of their relative speed.

Suitable docking algorithms include, but are not limited to:

DOCK [11], the prototypical program for structure-based drug design.

AUTODOCK [12, 6], which docks ligands in a flexible manner to receptors using grid-based Monte Carlo simulated annealing. The flexible nature of the AUTODOCK procedure helps to avoid bias (e.g. in orientation and conformation of the ligand in the active site) introduced by the user researcher [13] because, whilst the starting conformation in a rigid docking is normally biased towards an minimum energy conformation of the ligand, the binding conformation may be of relatively high conformational energy [14].

MOE-DOCK [15], in which a simulated annealing search algorithm is used to flexibly dock ligands. A grid-based energy evaluation is used to score docked conformations.

FLExX [5], which docks conformationally flexible ligands into a binding site using an incremental construction algorithm that builds the ligand in the site. Docked conformations are scored based on the strength of ligand-receptor interactions.

GOLD [16], a genetic algorithm for flexible ligand docking, with full ligand and partial protein flexibility. Energy functions are partly based on conformation and non-bonded contact information.

AFFINITY [7], which uses a two step process to dock ligands. First, initial placements of the ligand within the receptor are made using a Monte Carlo type procedure to search both conformational and Cartesian space. Second, a simulated annealing phase optimises the location of each ligand placement. During this phase, AFFINITY holds the 'bulk' of the receptor (atoms not in the binding site) rigid, while the binding site atoms and ligand atoms are movable.

$C^2$.LigandFit [7], which uses the energy of the ligand-receptor complex to automatically find best binding modes. Stochastic conformational search technique are used, and the best results from the conformational sampling are retained. A grid method is used to evaluate non-bonded interactions between the rigid receptor and the flexible ligand atoms.

Preferably, the docking algorithm is used in a 'high throughput' mode, in which members of large structural libraries of potential ligands are screened against the receptor structure [17].

Suitable structural libraries include the ACD (Available Chemical Directory, from MDL mc), AsInEx, Bionet, ComGenex, the Derwent World Drug Index (WDI), the Contact Service Company database, LaboTest, ChemBridge Express Pick, ChemStar, BioByteMasterFile, Orion, Sigma-Aldrich Library of Rare Chemicals (SALOR), Tricyclics for Automated Design (TRIAD), ILIAD database (University of California), the National Cancer Institute database (NCI), and the Aldrich, Fluka, Sigma and Maybridge catalogs. These are commercially available (e.g. the *HTS Chemicals* collections from Oxford Molecular, or the LeadQuest™ files from Tripos).

Pharmacophore Hypotheses

A pharmacophore (i.e. a collection of chemical features and 3D constraints that expresses specific characteristics responsible for activity) can be defined for a tetraspanin. The pharmacophore preferably includes surface-accessible features, more preferably including hydrogen bond donors and acceptors, charged/ionisable groups, and/or hydrophobic patches. These may be weighted depending on their relative importance in conferring activity [18].

Pharmacophores can be determined using software such as CATALYST (including HypoGen or HipHop) [7], CERIUS$^2$, or constructed by hand from a known conformation of a lead compound. The pharmacophore can be used to screen structural libraries, using a program such as CATALYST [7]. The CLIX program [19] can also be used, which searches for orientations of candidate molecules in structural databases that yield maximum spatial coincidence with chemical groups which interact with the receptor.

De Novo Compound Design

The binding surface or pharmacophore of a tetraspanin can be used to map favourable interaction positions for functional groups (e.g. protons, hydroxyl groups, amine groups, hydrophobic groups and/or divalent cations) or small molecule fragments. Compounds can then be designed de novo in which the relevant functional groups are located in the correct spatial relationship to interact with the tetraspanin.

Once functional groups or small molecule fragments which can interact with specific sites in the tetraspanin's binding surface have been identified, they can be linked in a single compound using either bridging fragments with the correct size and geometry or frameworks which can support the functional groups at favourable orientations, thereby providing a compound according to the invention. Whilst linking of functional groups in this way can be done manually, perhaps with the help of software such as QUANTA or SYBYL, automated or semi-automated de novo design approaches are also available:

- MCDLNG [20], which fills a receptor binding site with a close-packed array of generic atoms and uses a Monte Carlo procedure to randomly vary atom types, positions, bonding arrangements and other properties.
- MCSS/HOOK [21, 22, 7], which links multiple functional groups with molecular templates taken from a database.
- LUDI [23, 7], which computes the points of interaction that would ideally be fulfilled by a ligand, places fragments in the binding site based on their ability to interact with the receptor, and then connects them to produce a ligand.
- GROW [24], which starts with an initial 'seed' fragment (placed manually or automatically) and grows the ligand outwards.
- SPROUT [25], suite which includes modules to: identify favourable hydrogen bonding and hydrophobic regions within a binding pocket (HIPPO module); select functional groups and position them at target sites to form starting fragments for structure generation (EleFAnT); generate skeletons that satisfy the steric constraints of the binding pocket by growing spacer fragments onto the start fragments and then connecting the resulting part skeletons (SPIDeR); substitute hetero atoms into the skeletons to generate molecules with the electrostatic properties that are complementary to those of the receptor site (MARABOU). The solutions can be clustered and scored using the ALLigaTOR module.
- LEAPFROG [5], which evaluates ligands by making small stepwise structural changes and rapidly evaluating the binding energy of the new compound. Changes are kept or discarded based on the altered binding energy, and structures evolve to increase the interaction energy with the receptor.
- GROUPBUILD [26], which uses a library of common organic templates and a complete empirical force field description of the non-bonding interactions between a ligand and receptor to construct ligands that have chemically reasonable structure and have steric and electrostatic properties complimentary to the receptor binding site.
- CAVEAT [27], which designs linking units to constrain acyclic molecules.
- RASSE [28]

The Binding Site

To simplify computational complexity, algorithms for docking and ligand design will typically focus only on the binding site of a receptor—it is pointless to attempt to dock a ligand with a region in the receptor which is known not to be involved. Binding site identification is included in some algorithms (e.g. $C^2$.LigandFit, the 'Binding Site Analysis' module of INSIGHT II, the SPHGEN routine of DOCK). Some manual guidance may be required (e.g. AFFINITY).

Where a binding site has to be defined for a tetraspanin, this will typically comprise amino acids corresponding to human CD81 (SEQ ID NO: 1) residues (A) 114, 119, 123, 125, 126, 129, and/or (B) 142, 146, 149, 150, 153, 154, 197, 198, 199 and 200.

The Structural Representation

Structure-based design methods use a 3D structural representation of a tetraspanin. This may be a representation of (a) the complete tetraspanin, (b) a fragment of the tetraspanin that comprises the large extracellular loop (LEL), or (c) a fragment of the tetraspanin which includes the amino acids which interact with another tetraspanin to form a dimer.

The structural representation is preferably based on or derived from the atomic co-ordinates cd81lel.pdb as set out herein, which represents the CD81 tetraspanin LEL dimer [see also refs. 29, 30 & 31]. Suitable structural representations include 3D models and molecular surfaces derived from these atomic co-ordinates.

Variants of cd81lel.pdb can also be used for the invention, such as variants in which the r.m.s. deviation of the x, y and z co-ordinates for all heavy (i.e. not hydrogen) atoms are all less than 2.5 Å (e.g. less than 2 Å, preferably less than 1 Å, and more preferably less than 0.5 Å or less than 0.1 Å) compared with cd81.pdb. Co-ordinate transformations which retain the 3D spatial relationships of atoms may also be used to give suitable variants.

Preferred fragments of the tetraspanins whose co-ordinates can be used in the invention are:

- amino acids corresponding to human CD81 (SEQ ID NO: 1) residues 114, 119, 123, 125, 126, 129; and/or
- amino acids corresponding to human CD81 (SEQ ID NO: 1) residues 142, 146, 149, 150, 153, 154, 197, 198, 199 and 200.

It is preferred that the methods of the invention use only one protein chain i.e. only of the monomers in cd81lel.pdb. Where only one monomer is used, it is preferred to use the first monomer (residues 113–202) rather than the second (residues 213–302).

The water molecules in cd81lel.pdb can optionally be omitted when performing the methods of the invention.

The Storage Medium

The storage medium in which the tetraspanin structural representation is provided is preferably random-access memory (RAM), but may also be read-only memory (ROM e.g. CDROM), or a diskette. The storage medium may be local to the computer, or may be remote (e.g. a networked storage medium, including the internet).

Any suitable computer can be used in the present invention.

Testing Designed Compounds

The methods of the invention may comprise the further steps of: (c) providing a compound identified by said structure-based drug design techniques; and (d) contacting said compound with a tetraspanin, or a fragment thereof containing its LEL, and assaying the interaction between them.

Screening Methods

As well as using in silico methods, 'traditional' in vitro or in vivo methods of the pharmaceutical industry can be used to identify compounds that inhibit or promote dimerisation. The compounds may interact at the tetraspanin monomer:monomer interface regions. Typical assays will involve incubating test compounds with the tetraspanin of interest and observing whether dimerisation of the tetraspanin is promoted or inhibited, relative to wild-type:wild-type dimerisation.

In general, compounds will be identified by high-throughput screening libraries of test compounds. As well as using general compound libraries, more specific libraries can be used. These might be suggested by using the in silico approach discussed above—important pharmaceutical motifs in the ligands can be identified and mimicked in compound libraries (e.g. combinatorial libraries) for screening for dimerisation inhibition/promotion activity.

A recent approach to identifying molecules which interact at a protein:protein interface is described in reference 32, and the use of polypeptide display is described in reference 33.

Compounds and their Uses

The methods of the invention identify compounds that can that interact at tetraspanin monomer:monomer interface regions and either inhibit or promote dimerisation. These compounds may be designed de novo, may be known compounds, or may be based on known compounds. The compounds may be useful pharmaceuticals themselves, or may be prototypes which can be used for further pharmaceutical refinement (i.e. lead compounds) in order to improve binding affinity or other pharmacologically important features (e.g. bio-availability, toxicology, metabolism, pharmacokinetics etc.).

The invention thus provides: (i) a compound identified using the methods of the invention; (ii) a compound identified using the methods of the invention for use as a pharmaceutical; (iii) the use of a compound identified using the methods of the invention in the manufacture of a medicament; and (iv) a method of treating a patient, comprising administering an effective amount of a compound identified using the methods of the invention.

The invention also provides a compound which can either (i) interact with a tetraspanin protein and thereby inhibit the tetraspanin's ability to dimerise, or (ii) interact with a tetraspanin protein and thereby promote the tetraspanin's ability to dimerise.

The compounds of the invention preferably interact with a tetraspanin with a binding constant in the micromolar or, more preferably, nanomolar range or stronger.

Dimers

The invention also provides a tetraspanin in dimeric form.

This may be a homodimer (i.e. a dimer consisting of two identical tetraspanins) or a heterodimer (i.e. a dimer consisting of two different tetraspanins).

MODES FOR CARRYING OUT THE INVENTION

CD81-LEL Production

Figure 1B:
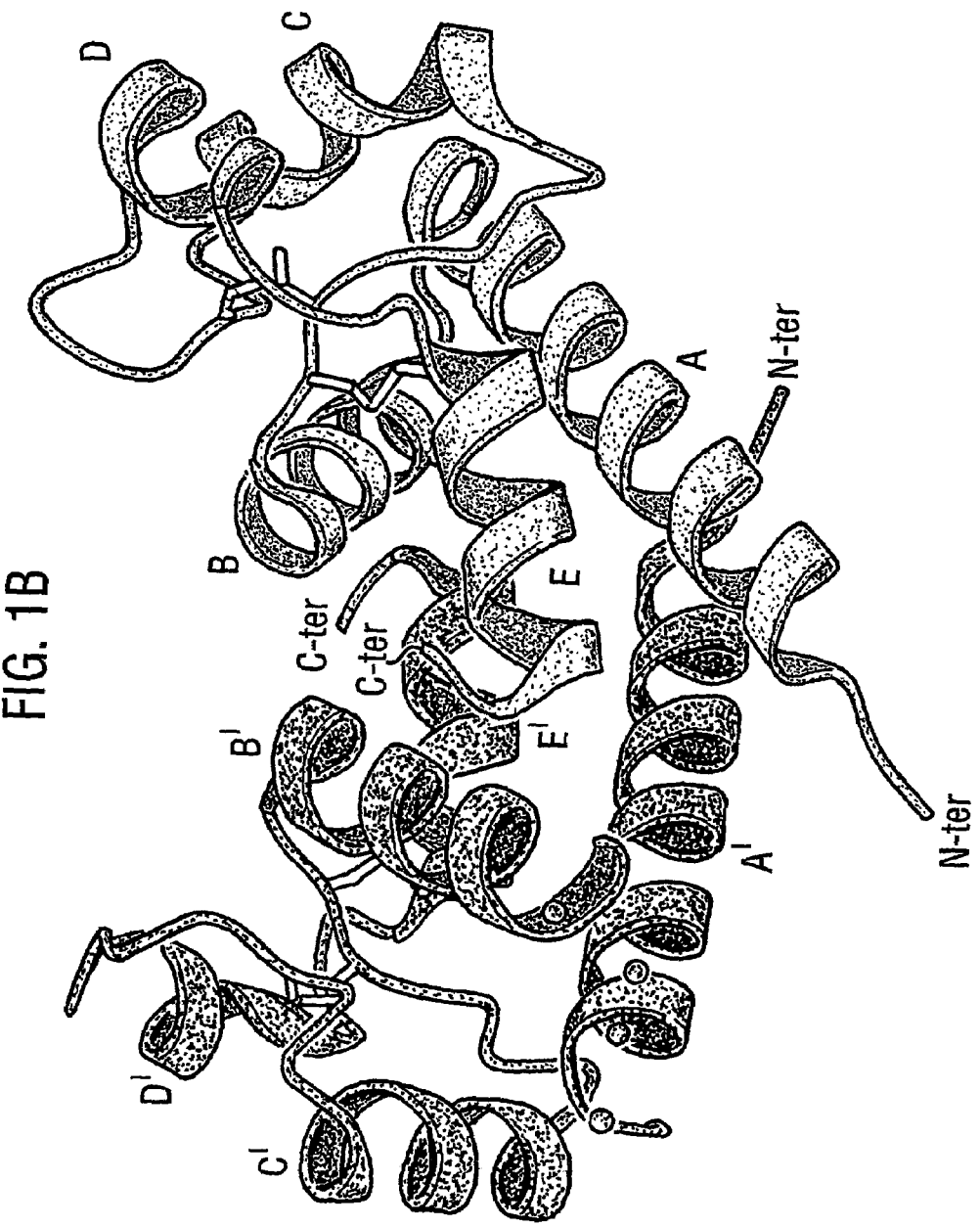
FIG. 1 shows: (1A) the CD81-LEL isolated chain tertiary structure, highlighting the head domain localisation relative to the N- and C-terminal helices (α-helices A and E, respectively), and the labelling of secondary structure elements. The two disulphide bridges are shown by yellow bonds; (1B) the dimeric CD81-LEL, showing the two subunits in blue and purple, with the helix labels distinguished by a ' symbol. The molecular two-fold axis is close to vertical, and located between the N- and C-termini of the two chains. Solid dots in the purple subunit trace an approximate path for the loops not observable in the electron density maps. (1C) A GRASP view of the molecular surface of the CD81-LEL dimer, in an orientation corresponding that of the blue subunit in panel 1A. This orientation brings α-helices C and D in the foreground; they can be recognised by comparison to panel A and by the low polarity region (white colour) in the upper part of the molecular surface.

CD81-LEL was purified from a recombinant E. coli strain as a fusion protein with the IgG binding domain of the S. aureus protein A. After purification of the chimeric protein, CD81-LEL was separated from the fusion by specific protease cleavage and further purified for the crystallization experiments. The purified protein was fully active as judged by the recombinant E2/CD81 inhibition of binding assay [35].

CD81-LEL Crystallisation

Crystals of CD81-LEL were obtained by mixing purified CD81-LEL at 10 mg/ml with 0.1M MES buffer (pH 6.0), 0.1M sodium chloride, and 10% PEG4000. The crystals belong to the monoclinic space group P2$_1$ (a=31.5 Å, b=77.2 Å, c=38.5 Å, β=107.4°), with two molecules per asymmetric unit (Vm of 2.16 Å$^3$/dalton). Crystals were flash-cooled at 100K with addition of 20% glycerol as cryoprotectant.

Whilst native crystals could be obtained easily, it was difficult to obtain suitable heavy atom derivatives for multiple isomorphous replacement techniques.

Three suitable derivatives were eventually produced, based on Lu, Hg and Pt:

| Parameter | Native 1 | LuCl$_3$ | Hg(Ac)$_2$ | K$_2$PtCl$_6$ | Native2 |
|---|---|---|---|---|---|
| Diffraction data | | | | | |
| Wavelength (Å) | 1.54 | 1.54 | 1.54 | 1.54 | 0.93 |
| Resolution (Å) | 2.7 | 2.7 | 3.0 | 3.3 | 1.6 |
| Unique reflections | 5136 | 4979 | 3619 | 2521 | 21557 |
| R$_{merge}$ (%) | 5.8 | 6.0 | 8.4 | 4.4 | 3.8 |
| Completeness (%) | 99.7 | 98.0 | 98.1 | 91.8 | 98.0 |
| | (99.4) | (93.4) | (97.1) | (87.5) | (93.1) |
| Redundancy | 3.4 | 2.0 | 3.2 | 8.2 | 6.9 |
| MIR phasing | | | | | |
| Phasing power/R$_{cullis}$ | | | | | |
| (acentric) | | 1.49/0.78 | 1.25/0.84 | 1.30/0.87 | |
| (centric) | | 1.16/0.82 | 0.98/0.85 | 0.90/0.89 | |
| (anom) | | 0.95/0.97 | 0.66/0.99 | 0.65/0.99 | |
| Overall FOM (acentric/centric) | | 0.63/0.58 | | | |
| Refinement | | | | | |
| Resolution range | | | | | 20.0–1.6 |
| R$_{factor}$/R$_{free}$ (%) | | | | | 18.7/23.8 |
| No. of protein atoms | | | | | 1345 |
| No. of solvent atoms | | | | | 194 |
| Ramachandran distribution | | | | | |
| % core | | | | | 92.4 |
| % allowed | | | | | 7.6 |
| % generous | | | | | 0.0 |
| % disallowed | | | | | 0.0 |
| r.m.s. bonds (Å) | | | | | 0.006 |
| r.m.s. angles (°) | | | | | 1.2 |
| Average B values (Å$^2$) | | | | | 35.2 |

NB:
R$_{merge}$ = ΣI Ii − <Ii> I/Σ <Ii>, where Ii is the observed intensity and <Ii> is the average intensity over symmetry equivalent measurements.
Phasing power = Σ|F$_H$|/Σ|F$_{PH}$(obs)I − IF$_{PH}$(calc)I I, where F$_{PH}$ and F$_H$ are the derivative and calculated heavy-atom structure factors, respectively.
R$_{cullis}$ = Σ||F$_{PH}$ − F$_P$I − IF$_H$(calc)I/IF$_{PH}$ − F$_P$I, where F$_{PH}$, F$_P$ and F$_H$ are the derivative, native and calculated heavy-atom structure factors, respectively.
R$_{factor}$ = Σ|F$_{obs}$|I − IF$_{calc}$|/Σ|F$_{obs}$|I. R$_{free}$ is the same as R$_{factor}$, but for a 5% subset of all reflections that were never used in crystallographic refinement.
FOM (Figure of merit) = IF(hkl)bestI/IF(hkl)I
Completeness is reported for all reflection and for the highest resolution shell.

Diffraction and Structure Solving

Native and derivative diffraction data were collected in house. Additional native data (at 1.6 Å resolution) were collected on beamline ID14 (ESRF, Grenoble, France), on a MAR CCD detector. All data were processed using DENZO and SCALEPACK [36] and merged using the CCP4 program suite [37]. Crystallographic phases were calculated with CCP4 programs and refined using SHARP [38] and SOLOMON [39]. The resulting electron density maps allowed about 80% of the two independent molecules to be traced. Model building and inspection was based on the O suite [40]. The structure was refined using CNS [41] and REFMAC [42]. 5% of the unique data were used to monitor the free R-factor. The final values for general R-factor and free R-factor are 18.7% and 23.8%, respectively. The refined model consists of 176 amino acids, with 194 water molecules, at 1.60 Å resolution. No residues are found in disallowed regions of the Ramachandran plot. Residues 238–241 are disordered in a A'B'loop.

Analysis of the Crystal Structure

FIG. 1A shows the CD81-LEL tertiary structure, which is essentially composed of five α-helices (A, B, C, D, E) spanning residues Asn115-Asp137, Ala140-Asp155, Leu165-Asn172, Asn180-Phe186 and Asp189-Gly200, respectively (amino acids numbered according to the full CD81 sequence; refs 43 & 44). A short 3$_{10}$ helical segment covers residues Leu162-Ala164. The anti-parallel A- and E-helices can be seen as the stalk of a mushroom-shaped molecule, whose head domain (about 60 residues) is built by packing of the shorter B-, C- and D-helices and their intervening loops (loops are defined by the helices they connect i.e. AB, ..., DE). A DALI search [45] of 3D protein structures did not show significant structural homology of the CD81-LEL fold to any known protein tertiary structure.

The dimeric assembly observed in the crystallographic asymmetric unit is shown in FIG. 1B. Two CD81-LEL chains assemble around a local two-fold axis, displaying intermolecular contacts mainly at the A:A' helix interface (a ' symbol distinguishes features of the partner subunit) and along the B-helix, which is in contact with the C-terminal region of the facing protomer. The subunit interface (986 Å$^2$) is composed of a polar residues for about 70% of its contact region.

The A:A' interface segment involves primarily residues Val114, Ile119, Val123, Gln125, Phe126 and Gln129, in both antiparallel helices, together with solvent mediated interactions between exposed polar side chains at the rim of the contact region. The second interface region includes residues Asn142, Val146, Thr149, Phe150, Thr153 & Leu154 which contact Leu197', Phe198', Ser199' & Gly200'. No water molecules are buried at the association interface.

Bivalent molecules (such as specific antibodies) capable of recognising human CD81 have been reported to have a higher affinity than E2 for CD81 [46]. In agreement with the crystal structure, this suggests that CD81 exists as a bomodimeric species at the cell surface. In the crystal structure, the distance between the D- and D'-helices is about 30 Å, close to the distance between antigen-binding sites in an assembled antibody molecule.

The C-terminal His-tag does not appear to have a structural influence because the proximity of N- and C-termini within each chain, permitted by the antiparallel arrangement of A- and E-helices, is compatible with their topological location between TM3 and TM4 of native CD81 [44]. Moreover, due to the quaternary structure two-fold symmetry, the N- and C-termini of the two protomers fall in a restricted area, but on opposite faces of the assembled dimer (FIG. 1B). This quaternary organization is compatible with inter- and intra-cellular aggregation of CD81 in homodimeric species, through the association interface described.

The overall shape of the CD81-LEL dimer is further characterized in FIG. 1C, as a surface displaying electrostatic potential. Besides the localization of negative potential in the central region of the dimer, a low polarity patch is present in a surface region comprising the C- and D-helices. In the crystal packing this region is virtually solvent inaccessible, due to extended contacts with a symmetry equivalent dimer.

Figure 3A:
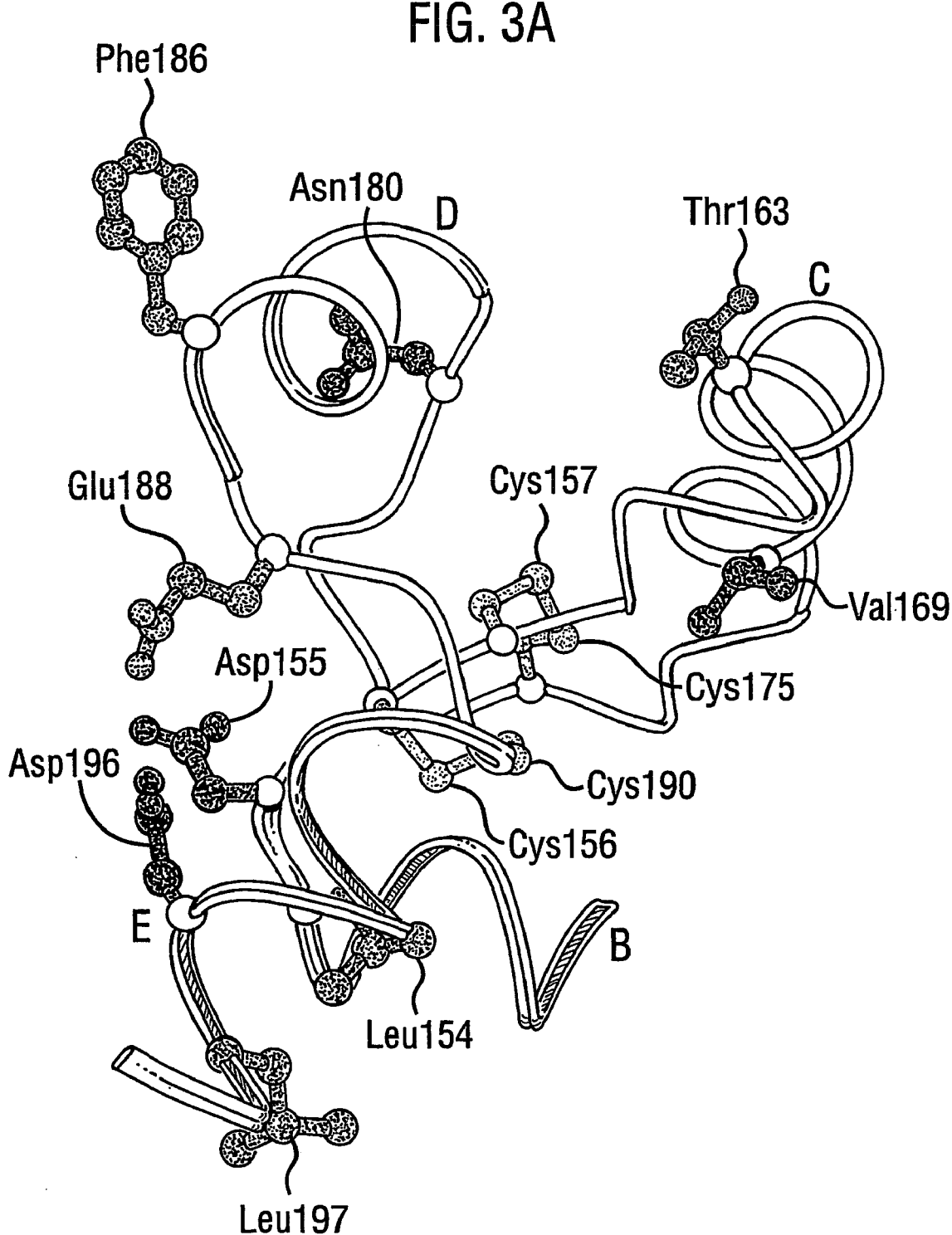
FIG. 3 shows: (3A) a schematic view of the location of Cys156—Cys190 and Cys 157—Cys175 disulphide bridges (yellow bonds) within the head domain of CD81-LEL. The additional residues displayed are the sites of mutation observed in agmCD81-LEL (green) and in tamCD81-LEL (red); (3B) the residues surrounding Tyr127, the head domain core, including electron density for the two disulphide bridges; (3C) a molecular surface representation of the CD81-LEL dimer, showing mutation sites 163, 186 and 196 (green patches) which have been shown to affect binding to HCV E2. Phe196 is in the upper-right part of the figure.

The CD81-LEL head domain is essentially composed of the last two turns of the A-helix, the B-, C-, D-helices, the intervening segments, and the DE loop. The domain fold is firstly stabilized by two tetraspanin-invariant intramolecular disulfide bridges [35, 43, 44, 46], which originate from two adjacent Cys residues (156 & 157) and are oriented approximately in opposite directions within the head domain (FIG. 3A). Their topological connections are Cys156-Cys190 and Cys157-Cys175: the first involves residues located at the C-terminus of the B-helix (Cys156) and at the N-terminus of the B-helix (Cys190); the second connects the BC segment (Cys157) with the CD loop region (Cys175). The latter region is fully exposed to solvent and specifically kinked towards the head domain core by virtue of the Cys157-Cys175 bridge. Of the four Cys residues, only Cys175 is partly accessible to solvent (20 Å$^2$).

The head domain is built around the core residue Tyr127, fully buried and surrounded by Leu131, Val47, Phe150, His151 and by the Asp128-His191 hydrogen-bonded saltbridge. Tyr127 OH atom is hydrogen-bonded to His151 NE2 atom (2.71 Å) and is 3.61 Å from the Cys190 Sγ atom (FIG. 3B). The imidazole ring of His151 is nestled between the two disulfide bridges, and is at hydrogen-bonding distance from Cys190 Sγ (3.56 Å). A hydrogen-bonding network involving Tyr127, His151 and Cys190 may play a role in regulating the redox properties of one or both disulfide bridges. Tyr127 is strictly conserved between species in CD81 (FIG. 2), and in all the CD9 sequences known to date; residue 191 is either His or Gln in amino acid sequences representing different tetraspanin sub-families (FIG. 2).

Sequence database surveys show that the tetraspanin family is composed of several sub-families (CD9, CD37, CD63, CD53, CD82, CD151 and others; ref. 43), for a total of about 160 amino acid sequences currently recognized. Among these, CD81 and CD9 families display close sequence (and thus structural) homology (23% residue identities are observed between human CD81-LEL and human CD9-LEL). FIG. 2 shows multiple amino acid sequence alignments of CD81-LEL from seven different species, together with human CD9-LEL and other tetraspanins. Sequence-based dendrogram analysis indicates that, within the sequences included in FIG. 2, human CD82-LEL is the one most distantly related to CD81-LEL (only 9% identical residues).

Figure 2:
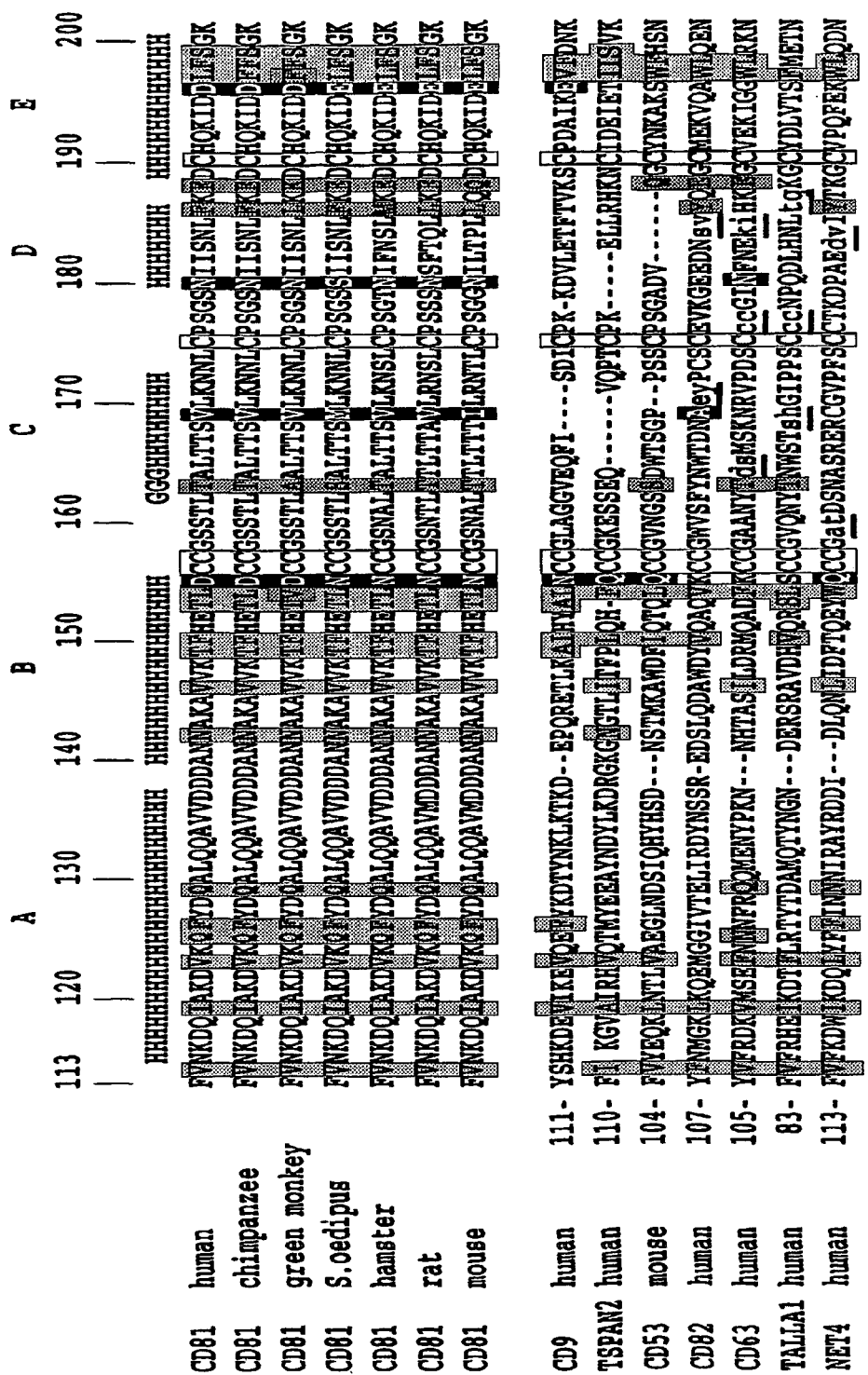
FIG. 2 shows an amino acid sequence alignment of LEL segments from mammalian CD81 and other tetraspanins. A symbol indicating the secondary structure [PROCHECK, ref. 34; H=α-helix; G=$3_{10}$ helix] is shown on the top line. On the leftmost column, name and organism are indicated. The accession numbers for the sequences used in the alignment are: human CD81 (SEQ ID NO: 2), NP_004347; Saguinus oedipus (SEQ ID NO: 4), CAB89875; rat (SEQ ID NO: 6), NP_037219; mouse (SEQ ID NO: 7), P35762; human CD9 (SEQ ID NO: 8), NP_001760; human TSPAN2 (SEQ ID NO: 9), NP_005716; mouse CD53 (SEQ ID NO: 10), NP_031677; human CD82 (SEQ ID NO: 11), NP_002222; human CD63 (SEQ ID NO: 12), NP_001771; human TALLA1 (SEQ ID NO: 13), AAF4412; human NET4 (SEQ ID NO: 14), AAC17120. Amino acid sequences of CD81 from chimpanzee (SEQ ID NO: 15), green monkey (SEQ ID NO: 3), and hamster (SEQ ID NO: 5) have been obtained from ref. 35. The last four sequences contain insertions which have not been included in the alignment to avoid the introduction of long gaps, located between pairs of underlined residues. In detail, the insertion stretches are: in CD82 (SEQ ID NO: 11), eLMNRPEVTy and sLSVRKG-FCEAPGNRTQSGNHPEDWPy; in CD63 (SEQ ID NO: 12), dWEKIPs, cINVTVGc and kAi; in TALLA1 (SEQ ID NO: 13), sPYFLEh, cMNETDc and tVAATKVNq; in NET4 (SEQ ID NO: 14), aFGADDWNLNIYFNCt and dVINTQCGYDARQKPEVDQQIv. The conserved Cys residues are enclosed in yellow boxes. Amino acids involved in the association interface are shown in pink boxes. The residues which are different between hCD81-LEL and agmCD81-LEL or tamCD81-LEL are marked in green or blue, respectively. Note that residue 163 is mutated in agmCD81-LEL and in tamCD81-LEL.
Figure 3B:
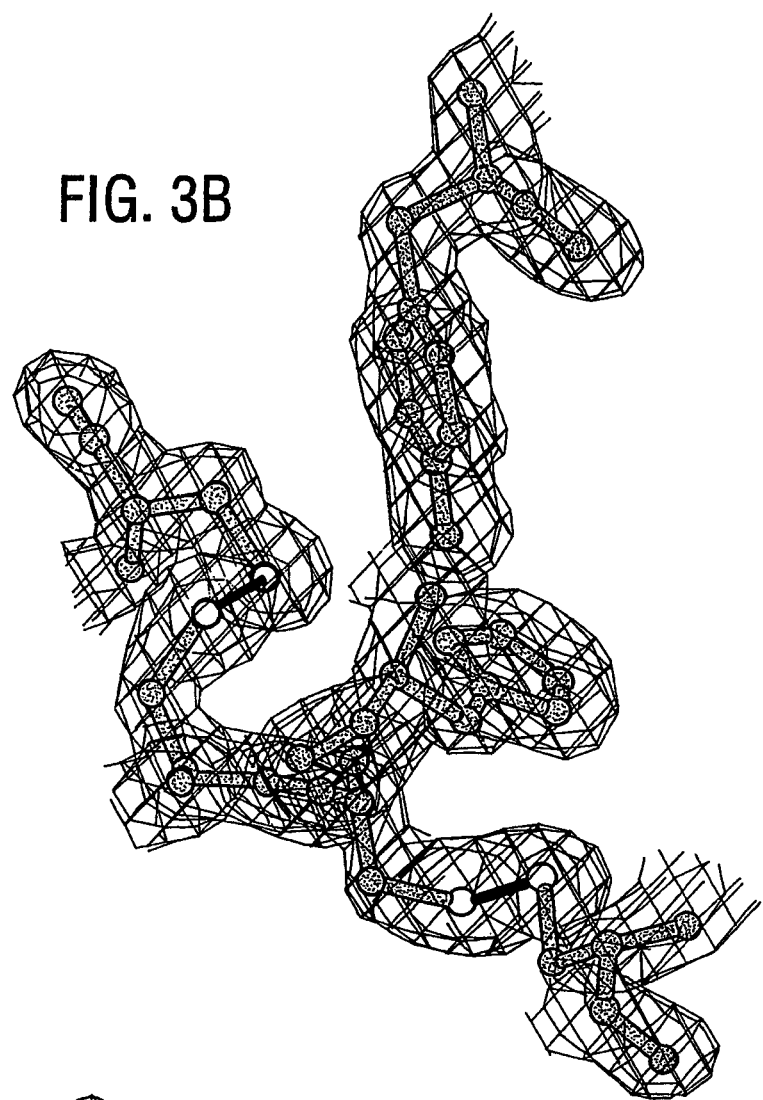

Besides the clearly recognized tetraspanin four-Cys consensus motif, inspection of the CD81 and CD9 alignment in FIG. 2 shows strict residue conservation at thirteen residues. Among these, four are charged amino acids (Lys116, Asp117, Lys148, and Lys201), which are totally solvent exposed in the assembled CD81-LEL dimer. The remaining nine conserved residues can be divided into three structural classes:

(a) Tyr127, His151 and Ile194 are buried residues involved in intramolecular interactions stabilizing the head domain and its contacts to the E-helix, as described above.

(b) Val123, Phe126, Leu154 and Phe198, which are primarily involved in subunit interface contacts, together with residues Ile119 and Phe150, conservatively substituted at the association interface. Conservation of the interface hydrophobic residues can be recognized throughout the sequence alignment of FIG. 2, suggesting that the observed subunit interface has a general functional significance for both homo- or hetero-dimeric tetraspanin association related to intra- or inter-cellular recognition processes.

(c) Gly158 and Pro176, both of which display unique positions and conformations (as indicated by their Ramachandran Φ, ψ pairs) within the head domain fold, occurring after the Cys156-Cys157 pair and after Cys175. The selection of Gly and Pro at sites 158 and 176, respectively, may be required by the structural constraints imposed on the CD loop by the Cys157-Cys175 bridge, coding its specific kink towards the B-helix.

Analysis of the available sequences indicates that tetraspanin LEL segments display enhanced residue variability, deletions or insertions in the protein segments 158–174 and 176–189, which are comprised between the two disulfide bridges (see FIG. 2). The two segments span the BC loop, the C- and the D-helices and the DE hinge i.e. mostly solvent-exposed regions of the head domain (see FIGS. 1B & 3A). The structural location and sequence variability of this protein region, as opposed to generally conserved protein interface and core regions, suggests its involvement in species- or tetraspanin-specific recognition processes.

No binding of the HCV E2 glycoprotein to african green monkey (*Chlorocebus aethiops*) CD81 has been observed, but the LELs of human and AGM CD81 differ at only five residues: 154, 163, 186, 188 and 197 [35]. Conversely, E2 does bind to tamarin (*Saguinus oedipus*) CD81 with high affinity, and it differs from human CD81 only at residues 155, 163, 169, 180 and 196. Three of the AGM mutations have been engineered into human CD81-LEL ad their binding properties versus recombinant E2 and anti-CD81 antibodies have been analysed in vitro [46]. Phe186 is the most critical residue affecting E2 binding, since the F186A mutation in human CD81-LEL fully impairs binding to E2 and to specific antibodies, the introduction of Phe186 in AGM CD81-LEL restores E2 binding, and tamarin CD81 displays Phe186 [35, 46, 47]. The Thr163Ala mutation marginally improves human CD81 binding to E2, whereas Asp196Glu mutation decreases binding to E2 [46].

Figure 3C:
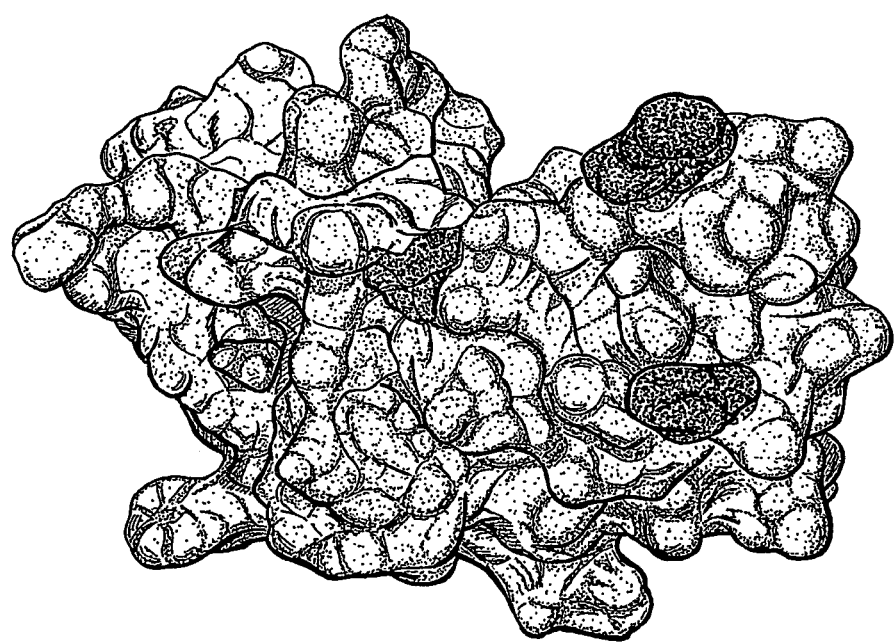

From a structural viewpoint, the tamarin and AGM mutated residues map in the head domain, with the exception of residues 196 and 197, which fall next to the C-terminus (see FIG. 3C), Leu197 being a subunit interface residue in human CD81. Residues 155, 163, 180, 186 and 188 are solvent exposed, such that their conservative substitution should not affect the domain conformation. On the other hand, the substitution of residues 154 and 169 is subject to polarity and residue size restrictions, since they occur at buried locations next to both disulfide bridges. In human CD81 Thr163 is located in the short $3_{10}$ segment preceding the C-helix, and Phe186 is the last residue in the D-helix. The two antiparallel helices build up a sort of narrow "canyon" sub-structure, whose floor is essentially defined by the Cys157-Cys175 disulfide connecting the CD loop to the domain core. Residues 163 and 186 are located at the canyon end opposing the CD loop (FIGS. 3A & 3C).

The mutant AGM and tamarin residues which affect E2 binding map to the C-, D-, E-helices, and the intervening segments i.e. residues mostly comprised within the two conserved disulfide bridges and including the 179–193 sequence stretch recognised as the minimal epitope for E2 binding [46]. Conformational integrity of this region is likely related to the oxidised state of the disulfide bridges, particularly the Cys157-Cys175 bridge; reduction of the disulfides impairs E2 and antibody recognition experiments [46, 48]. Sequence alignments show that the identified region displays highest residue variability within the CD81-LEL subfamily (FIG. 2), but also within other members of the tetraspanin family, which may bear specific residue deletions and insertions affecting the tertiary structure according to their molecular recognition requirements.

The conservation in the CD81 sequences of the hydrophobic residues Ile181, Ile182, Leu185, and Phe186 belonging to the D-helix (FIG. 2) is peculiar, since their solvent-exposed location (FIGS. 1C & 3A) should select against their conservation through species. Such an uncommon structural property, the extended intermolecular crystal contacts observed in this region, and the dramatic loss of E2 affinity related to Phe186 mutation, suggest that the D-helix region is the docking site for the viral glycoprotein E2.

Tetraspanin Dimers

Tetraspanins play a role in the lateral association of large cell-surface signalling complexes, but very little is known about how the tetraspanins interact to build up the so-called "tetraspan web". To investigate this, the LEL of CD81 was co-expressed in *E. coli* with the LELs from two other tetraspanins (CD82 and CD63) in an attempt to form heterodimers.

CD82-LEL and CD63-LEL were cloned in the expression vector pEZZ18 in the same way as described in reference 31. After PCR amplification, CD82-LEL was cloned into restriction sites EcoRI and HindIII, while CD63-LEL was cloned into SacI and HindIII. The resulting plasmids encode for fusion proteins having *S. aureus* Protein A at their N-terminus and a stretch of six histidine residues at the C-terminus. Between Protein A and LEL domains there is a thrombin cleavage site. The plasmid constructs were then transformed into *E. coli* DB1035 cells.

The fragment containing the Shine-Dalgarno sequence followed by the sequence encoding the Protein A-CD82-LEL-(His)$_6$ was amplified from pEZZ CD82 and cloned in the plasmid pEZZ CD81 at the HindIII restriction site. The resulting plasmid pEZZ CD81-CD82 was transformed into *E. coli* DB1035 cells. The same procedure was used to generate plasmid pEZZ CD81-CD63.

*E. coli* DB1035 containing plasmid pEZZ CD81-CD82 and *E. coli* DB1035 containing plasmid pEZZ CD81-CD63 were grown in LB broth containing ampicillin (100 μg/ml) at 37° C. for 16 hours and the cells were harvested by centrifugation and used to purify the recombinant proteins.

The co-expressed fusion proteins were purified using IgG Sepharose followed by thrombin digestion. The LEL-(His)$_6$ fragments were further purified using IMAC.

Co-purified CD81/CD82 LEL (150 ng) and CD81/CD63 LEL (50 ng) proteins were immunoprecipitated in a total volume of 0.1 ml for 2 hours at 4° C. under constant agitation in PBS, 0.1% Triton X-100, 0.3 mg/ml monoclonal antibodies against CD81, CD82 or CD63. To collect the immune complexes one third volume Protein G Sepharose (Amersham) was added and after 1 hour at 4° C. the resin was pelleted and washed two times with PBS, 0.1% Triton X-100. Co-precipitated molecules were eluted from immune complexes by incubation with 2×SDS gel-loading buffer (without reducing agents) at room temperature for 1 hour.

Immunoprecipitated molecules were separated by SDS-PAGE in non-reducing conditions. The proteins were then transferred to a PVDF membrane and the membrane was blocked overnight in PBS 0.05% Tween-20 10% non-fat dry milk. Blots were developed by incubation with specific mouse anti-CD81, anti-CD82 or anti-CD63 antibodies followed by incubation with peroxidase-conjugated anti-mouse IgG. Immunoreactive bands were visualised using the ECL Western blotting detection kit (Amersham).

Figure 4A:
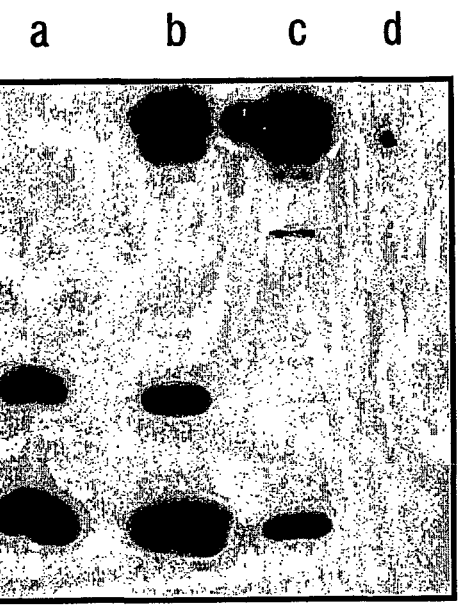
FIGS. 4 and 5 show Western blots of immunoprecipitated heterodimers.
Figure 4B:
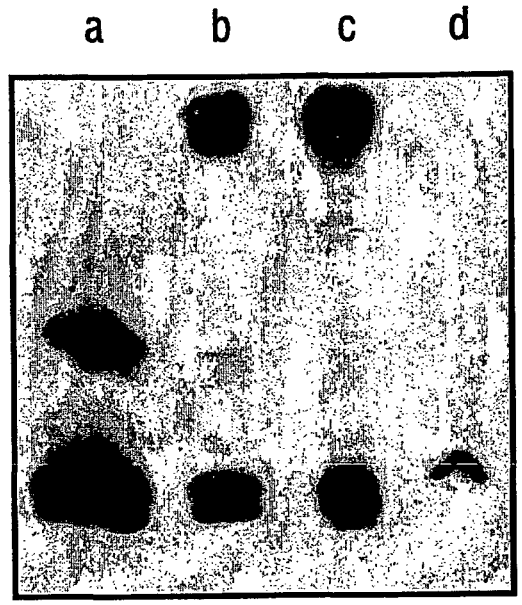

FIG. 4 shows that CD81-LEL and CD82-LEL associate. In FIG. 4A the blot was visualised with anti-CD81; in FIG. 4B anti-CD82 was used. The antibody used to immunoprecipitate proteins was either anti-CD81 (lane b) or anti-CD82 (lane c). It can be seen that the protein which is immunoprecipitated by anti-CD81 is recognised by both anti-CD81 and anti-CD82; similarly, the protein which is immunoprecipitated by anti-CD82 is recognised by both anti-CD82 and anti-CD81. Proteins not subjected to immunoprecipitation (lane a) or not stained with antibody (lane d) do not show either protein.

Figure 5A:
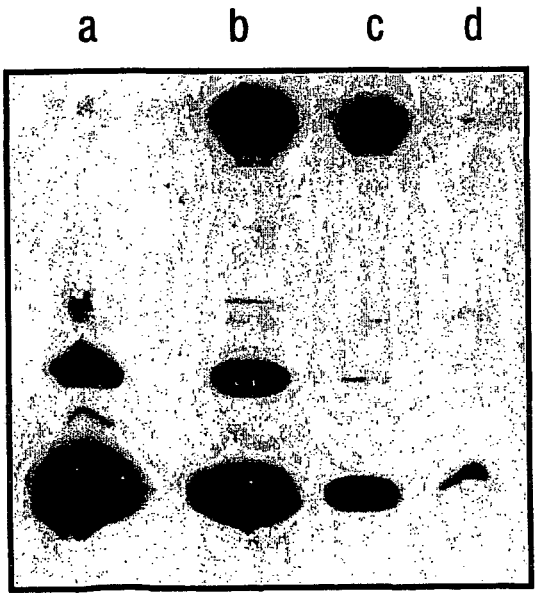
Figure 5B:
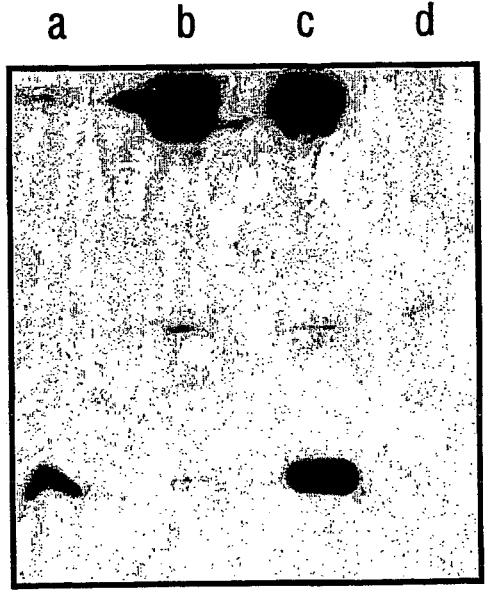

FIG. 5 shows similar results—the protein which is immunoprecipitated by anti-CD81 (lane b) is recognised by both anti-CD81 (FIG. 5A) and anti-CD63 (FIG. 5B); and the protein which is immunoprecipitated by anti-CD63 (lane c) is recognised by both anti-CD63 and anti-CD81.

It is thus evident that CD81 can form dimers with both CD63 and CD82, as well as with itself.

It will be understood that the invention has been described by way of example only and modifications may be made whilst remaining within the scope and spirit of the invention.

REFERENCES (the contents of which are hereby incorporated in full herein)

1—Maecker et al. (1997) *FASEB J* 11:428–442.
2—Levy et al. (1998) *Annu. Rev. Immunol.* 16:89
3—Radford et al. (1996) *Biochem Biophys Res Commun.* 222:13
4—Further details: *Rational drug design: novel methodology and practical applications*, ACS Symposium Series vol. 719 (Parrill & Reddy eds., 1991).
5—Available from Tripos Inc (tripos.com).
6—Available from Oxford Molecular (oxmol.co.uk/).
7—Available from Molecular Simulations Inc (msi.com/).
8—Available from Hypercube Inc (hyper.com/).
9—Available from Pyramid Learning (chemsite.org/).

10—Blaney & Dixon (1993) *Perspectives in Drug Discovery and Design* 1:301

11—Kuntz et al. (1982) *J. Mol. Biol.* 161: 269–288); available from UCSF.

12—Goodsell & Olson (1990) *Proteins: Structure, Function and Genetics* 8:195–202.

13—Meyer et al. (1995) *Persp. Drug Disc. Des.* 3:168–195

14—Nicklaus et al. (1995) *Bioorganic & Medicinal Chemistry* 3:411

15—Available from Chemical Computing Group Inc. (chemcomp.com/).

16—Jones et al. (1997) *J. Mol. Biol.* 267:727–748

17—Martin (1992) *J. Med Chem.* 35:2145–54.

18—also *Computer-Assisted Lead Finding and Optimization* (eds. Testra & Folkers, 1997).

19—Davic & Lawrence (1992) *Proteins* 12:31–41.

20—Gehlhaar et al. (1995) *J. Med. Chem.* 38:466–72.

21—Caflish et al. (1993) *J. Med. Chem.* 36:2142–67

22—Bisen et al. (1994) *Proteins: Str. Funct. Genet.* 19:199–221.

23—Bohm (1992) *J. Comp. Aided Molec. Design* 6:61–78.

24—Moon & Howe (1991) *Proteins: Str. Funct. Genet.* 11:314–328.

25—Available from chem.leeds.ac.uk/ICAMS/SPROUT.html.

26—Rotstein et al. (1993) *J. Med. Chem.* 36:1700.

27—Lauri & Bartlett (1994) *Comp. Aided Mol. Design* 8:51–66.

28—Lai (1996) *J. Chem. Inf. Comput. Sci.* 36:1187–1194.

29—File 1G8Q at the Protein Data Bank [rcsb.org/pdb/]

30—Kitadokoro et al. (2001) *Acta Crystallogr D Biol Crystallogr* 57:156–158.

31—Kitadokoro et al. (2001) *EMBO J.* 20:12–18.

32—Guo et al. (2000) *Science* 288:2042–45.

33—Jermutus & Osbom (2000) *TIBTECH* 18:280–281.

34—Laskowski et al. (1993) *J. Appl. Crystallogr.* 26:283

35—Pileri et al. (1998) *Science* 282:938–941.

36—Otwinowski & Minor (1996) *Methods Enzymol.* 276: 307.

37—CCP4, *Acta Crystallogr.* D50,760 (1994).

38—Fortelle &. Bricogne (1997) *Methods Enzymol.* B 472

39—Abrahams & Leslie (1996) *Acta Crystallogr.* D52,30.

40—Jones et al. (1991) *Acta Crystallogr.* A47,110

41—Brunget et al. (1998) *Acta Crystallogr.* D 54,905

42—Murshudov et al. (1997) *Acta Crystallogr.* D 53,240

43—Maecker et al. (1997) *FASEB J.* 11:428–42.

44—Levy et al. (1998) *Annu Rev Immunol.* 16:89–109

45—Holm & Sander (1993) *J. Mol. Biol.* 233,123

46—Higginbottom et al. (2000) *J. Virol.* 74:3642–9.

47—Meola et al. (2000) *J. Virol.* 74:5933.

48—Petracca et al. (2000) *J. Virol.* 74:4824–30.

```
                    PDB FILE LISTING - cd811e1.pdb

REMARK Written by O version 7.0.0
REMARK Mon Jun 26 07:13:19 2000
CRYST1   31.485      77.172     38.462   90.00 107.39    90.00
ORIGX1    1.000000   0.000000   0.000000   0.00000
ORIGX2    0.000000   1.000000   0.000000   0.00000
ORIGX3    0.000000   0.000000   1.000000   0.00000
SCALE1    0.031761  -0.000001   0.009946   0.00000
SCALE2    0.000000   0.012958   0.000000   0.00000
SCALE3    0.000000   0.000000   0.027245   0.00000
ATOM      1  CB   PHE  A13      13.054  44.460  -4.086  1.00  35.22   6
ATOM      2  CG   PHE  A13      13.550  44.904  -5.447  1.00  34.10   6
ATOM      3  CD1  PHE  A13      13.436  46.217  -5.867  1.00  33.03   6
ATOM      4  CD2  PHE  A13      14.097  43.957  -6.288  1.00  31.53   6
ATOM      5  CE1  PHE  A13      13.846  46.604  -7.112  1.00  41.68   6
ATOM      6  CE2  PHE  A13      14.536  44.353  -7.552  1.00  33.43   6
ATOM      7  CZ   PHE  A13      14.417  45.655  -7.929  1.00  29.35   6
ATOM      8  C    PHE  A13      13.055  44.591  -1.648  1.00  34.73   6
ATOM      9  O    PHE  A13      13.493  43.601  -1.095  1.00  35.94   8
ATOM     10  N    PHE  A13      15.194  44.738  -2.818  1.00  38.93   7
ATOM     11  CA   PHE  A13      13.749  45.121  -2.929  1.00  35.51   6
ATOM     12  N    VAL  A14      12.014  45.304  -1.292  1.00  30.69   7
ATOM     13  CA   VAL  A14      11.297  44.908  -0.047  1.00  30.59   6
ATOM     14  CB   VAL  A14      10.318  46.078   0.218  1.00  28.83   6
ATOM     15  CG1  VAL  A14       9.273  45.698   1.249  1.00  39.07   6
ATOM     16  CG2  VAL  A14      11.101  47.339   0.495  1.00  32.04   6
ATOM     17  C    VAL  A14      10.519  43.644  -0.291  1.00  33.72   6
ATOM     18  O    VAL  A14       9.766  43.438  -1.254  1.00  38.10   8
ATOM     19  N    ASN  A15      10.631  42.726   0.661  1.00  26.02   7
ATOM     20  CA   ASN  A15       9.999  41.431   0.616  1.00  26.31   6
ATOM     21  CB   ASN  A15      11.119  40.392   0.761  1.00  32.36   6
ATOM     22  CG   ASN  A15      10.695  38.985   0.416  1.00  36.81   6
ATOM     23  OD1  ASN  A15       9.539  38.606   0.608  1.00  37.44   8
ATOM     24  ND2  ASN  A15      11.665  38.213  -0.109  1.00  41.24   7
ATOM     25  C    ASN  A15       9.050  41.307   1.840  1.00  29.28   6
ATOM     26  O    ASN  A15       9.588  40.946   2.886  1.00  29.32   8
ATOM     27  N    LYS  A16       7.818  41.715   1.661  1.00  28.31   7
ATOM     28  CA   LYS  A16       6.877  41.671   2.790  1.00  30.52   6
ATOM     29  CB   LYS  A16       5.534  42.201   2.323  1.00  32.42   6
ATOM     30  CG   LYS  A16       4.438  42.302   3.360  1.00  40.71   6
ATOM     31  CD   LYS  A16       3.494  41.125   3.184  1.00  54.74   6
ATOM     32  CE   LYS  A16       2.097  41.504   3.656  1.00  50.77   6
ATOM     33  NZ   LYS  A16       1.233  40.305   3.663  1.00  45.99   7
ATOM     34  C    LYS  A16       6.740  40.325   3.467  1.00  29.54   6
```

-continued

| | | | | | | | | | | | |
|---|---|---|---|---|---|---|---|---|---|---|---|
| \multicolumn{12}{|c|}{PDB FILE LISTING - cd811e1.pdb} |

| ATOM | 35 | O | LYS | A | 116 | 6.720 | 40.232 | 4.696 | 1.00 | 27.76 | 8 |
| ATOM | 36 | N | ASP | A | 117 | 6.611 | 39.248 | 2.695 | 1.00 | 29.77 | 7 |
| ATOM | 37 | CA | ASP | A | 117 | 6.551 | 37.911 | 3.304 | 1.00 | 30.69 | 6 |
| ATOM | 38 | CB | ASP | A | 117 | 6.396 | 36.802 | 2.261 | 1.00 | 35.31 | 6 |
| ATOM | 39 | CG | ASP | A | 117 | 5.055 | 36.833 | 1.558 | 1.00 | 41.21 | 6 |
| ATOM | 40 | OD1 | ASP | A | 117 | 4.955 | 36.192 | 0.472 | 1.00 | 44.39 | 8 |
| ATOM | 41 | OD2 | ASP | A | 117 | 4.140 | 37.496 | 2.092 | 1.00 | 44.63 | 8 |
| ATOM | 42 | C | ASP | A | 117 | 7.800 | 37.628 | 4.109 | 1.00 | 31.27 | 6 |
| ATOM | 43 | O | ASP | A | 117 | 7.612 | 37.076 | 5.208 | 1.00 | 29.68 | 8 |
| ATOM | 44 | N | GLN | A | 118 | 9.006 | 37.962 | 3.675 | 1.00 | 27.32 | 7 |
| ATOM | 45 | CA | GLN | A | 118 | 10.192 | 37.645 | 4.471 | 1.00 | 23.79 | 6 |
| ATOM | 46 | CB | GLN | A | 118 | 11.500 | 37.816 | 3.709 | 1.00 | 33.42 | 6 |
| ATOM | 47 | CG | GLN | A | 118 | 12.392 | 36.592 | 3.917 | 1.00 | 50.37 | 6 |
| ATOM | 48 | CD | GLN | A | 118 | 11.870 | 35.402 | 3.136 | 1.00 | 55.11 | 6 |
| ATOM | 49 | OE1 | GLN | A | 118 | 11.385 | 34.436 | 3.730 | 1.00 | 61.81 | 8 |
| ATOM | 50 | NE2 | GLN | A | 118 | 11.933 | 35.435 | 1.806 | 1.00 | 55.23 | 7 |
| ATOM | 51 | C | GLN | A | 118 | 10.218 | 38.513 | 5.755 | 1.00 | 25.07 | 6 |
| ATOM | 52 | O | GLN | A | 118 | 10.575 | 38.027 | 6.842 | 1.00 | 28.38 | 8 |
| ATOM | 53 | N | ILE | A | 119 | 9.863 | 39.760 | 5.566 | 1.00 | 25.14 | 7 |
| ATOM | 54 | CA | ILE | A | 119 | 9.880 | 40.701 | 6.719 | 1.00 | 23.26 | 6 |
| ATOM | 55 | CB | ILE | A | 119 | 9.498 | 42.128 | 6.266 | 1.00 | 27.36 | 6 |
| ATOM | 56 | CG2 | ILE | A | 119 | 9.266 | 43.023 | 7.510 | 1.00 | 23.47 | 6 |
| ATOM | 57 | CG1 | ILE | A | 119 | 10.560 | 42.718 | 5.345 | 1.00 | 30.01 | 6 |
| ATOM | 58 | CD1 | ILE | A | 119 | 10.193 | 44.009 | 4.618 | 1.00 | 30.66 | 6 |
| ATOM | 59 | C | ILE | A | 119 | 8.938 | 40.184 | 7.788 | 1.00 | 23.31 | 6 |
| ATOM | 60 | O | ILE | A | 119 | 9.311 | 40.183 | 8.996 | 1.00 | 25.16 | 8 |
| ATOM | 61 | N | ALA | A | 120 | 7.712 | 39.788 | 7.412 | 1.00 | 24.17 | 7 |
| ATOM | 62 | CA | ALA | A | 120 | 6.781 | 39.316 | 8.463 | 1.00 | 25.04 | 6 |
| ATOM | 63 | CB | ALA | A | 120 | 5.384 | 38.976 | 7.916 | 1.00 | 29.48 | 6 |
| ATOM | 64 | C | ALA | A | 120 | 7.304 | 38.051 | 9.147 | 1.00 | 24.84 | 6 |
| ATOM | 65 | O | ALA | A | 120 | 7.234 | 37.964 | 10.377 | 1.00 | 25.63 | 8 |
| ATOM | 66 | N | LYS | A | 121 | 7.886 | 37.145 | 8.333 | 1.00 | 25.80 | 7 |
| ATOM | 67 | CA | LYS | A | 121 | 8.459 | 35.934 | 8.924 | 1.00 | 27.45 | 6 |
| ATOM | 68 | CB | LYS | A | 121 | 8.937 | 35.072 | 7.739 | 1.00 | 31.96 | 6 |
| ATOM | 69 | CG | LYS | A | 121 | 10.222 | 34.305 | 7.934 | 1.00 | 45.25 | 6 |
| ATOM | 70 | CD | LYS | A | 121 | 11.443 | 35.174 | 7.733 | 1.00 | 55.59 | 6 |
| ATOM | 71 | CE | LYS | A | 121 | 12.488 | 34.542 | 6.833 | 1.00 | 54.95 | 6 |
| ATOM | 72 | NZ | LYS | A | 121 | 13.434 | 35.534 | 6.259 | 1.00 | 49.41 | 7 |
| ATOM | 73 | C | LYS | A | 121 | 9.581 | 36.310 | 9.886 | 1.00 | 24.12 | 6 |
| ATOM | 74 | O | LYS | A | 121 | 9.630 | 35.792 | 11.038 | 1.00 | 26.90 | 8 |
| ATOM | 75 | N | ASP | A | 122 | 10.378 | 37.296 | 9.562 | 1.00 | 23.49 | 7 |
| ATOM | 76 | CA | ASP | A | 122 | 11.489 | 37.734 | 10.391 | 1.00 | 24.47 | 6 |
| ATOM | 77 | CB | ASP | A | 122 | 12.549 | 38.580 | 9.737 | 1.00 | 22.87 | 6 |
| ATOM | 78 | CG | ASP | A | 122 | 13.362 | 37.819 | 8.674 | 1.00 | 26.68 | 6 |
| ATOM | 79 | OD1 | ASP | A | 122 | 13.273 | 36.574 | 8.574 | 1.00 | 32.55 | 8 |
| ATOM | 80 | OD2 | ASP | A | 122 | 14.103 | 38.528 | 7.955 | 1.00 | 31.33 | 8 |
| ATOM | 81 | C | ASP | A | 122 | 10.982 | 38.456 | 11.665 | 1.00 | 24.38 | 6 |
| ATOM | 82 | O | ASP | A | 122 | 11.555 | 38.251 | 12.733 | 1.00 | 22.88 | 8 |
| ATOM | 83 | N | VAL | A | 123 | 9.945 | 39.256 | 11.552 | 1.00 | 24.91 | 7 |
| ATOM | 84 | CA | VAL | A | 123 | 9.363 | 39.886 | 12.747 | 1.00 | 22.20 | 6 |
| ATOM | 85 | CB | VAL | A | 123 | 8.288 | 40.939 | 12.399 | 1.00 | 18.76 | 6 |
| ATOM | 86 | CG1 | VAL | A | 123 | 7.800 | 41.562 | 13.705 | 1.00 | 20.06 | 6 |
| ATOM | 87 | CG2 | VAL | A | 123 | 9.037 | 42.026 | 11.568 | 1.00 | 23.40 | 6 |
| ATOM | 88 | C | VAL | A | 123 | 8.825 | 38.829 | 13.692 | 1.00 | 20.54 | 6 |
| ATOM | 89 | O | VAL | A | 123 | 9.008 | 38.889 | 14.911 | 1.00 | 22.54 | 8 |
| ATOM | 90 | N | LYS | A | 124 | 8.098 | 37.844 | 13.114 | 1.00 | 21.95 | 7 |
| ATOM | 91 | CA | LYS | A | 124 | 7.566 | 36.768 | 14.018 | 1.00 | 24.00 | 6 |
| ATOM | 92 | CB | LYS | A | 124 | 6.797 | 35.783 | 13.134 | 1.00 | 26.02 | 6 |
| ATOM | 93 | CG | LYS | A | 124 | 5.505 | 36.413 | 12.619 | 1.00 | 25.26 | 6 |
| ATOM | 94 | CD | LYS | A | 124 | 4.836 | 35.414 | 11.667 | 1.00 | 29.55 | 6 |
| ATOM | 95 | CE | LYS | A | 124 | 3.735 | 36.131 | 10.886 | 1.00 | 32.92 | 6 |
| ATOM | 96 | NZ | LYS | A | 124 | 3.115 | 35.139 | 9.941 | 1.00 | 31.45 | 7 |
| ATOM | 97 | C | LYS | A | 124 | 8.722 | 36.046 | 14.715 | 1.00 | 25.01 | 6 |
| ATOM | 98 | O | LYS | A | 124 | 8.678 | 35.783 | 15.931 | 1.00 | 24.77 | 8 |
| ATOM | 99 | N | GLN | A | 125 | 9.817 | 35.779 | 14.045 | 1.00 | 22.22 | 7 |
| ATOM | 100 | CA | GLN | A | 125 | 10.963 | 35.105 | 14.630 | 1.00 | 25.09 | 6 |
| ATOM | 101 | CB | GLN | A | 125 | 11.933 | 34.615 | 13.553 | 1.00 | 28.89 | 6 |
| ATOM | 102 | CG | GLN | A | 125 | 13.031 | 33.781 | 14.176 | 1.00 | 28.74 | 6 |
| ATOM | 103 | CD | GLN | A | 125 | 12.610 | 32.683 | 15.121 | 1.00 | 51.08 | 6 |
| ATOM | 104 | OE1 | GLN | A | 125 | 11.475 | 32.201 | 15.227 | 1.00 | 48.79 | 8 |
| ATOM | 105 | NE2 | GLN | A | 125 | 13.577 | 32.195 | 15.910 | 1.00 | 55.92 | 7 |
| ATOM | 106 | C | GLN | A | 125 | 11.677 | 35.939 | 15.667 | 1.00 | 22.42 | 6 |
| ATOM | 107 | O | GLN | A | 125 | 12.007 | 35.481 | 16.740 | 1.00 | 26.28 | 8 |
| ATOM | 108 | N | PHE | A | 126 | 11.872 | 37.249 | 15.396 | 1.00 | 21.19 | 7 |
| ATOM | 109 | CA | PHE | A | 126 | 12.395 | 38.149 | 16.407 | 1.00 | 23.84 | 6 |
| ATOM | 110 | CB | PHE | A | 126 | 12.358 | 39.571 | 15.868 | 1.00 | 20.40 | 6 |
| ATOM | 111 | CG | PHE | A | 126 | 12.978 | 40.587 | 16.762 | 1.00 | 22.25 | 6 |

-continued

| | | | | | | | | | | |
|---|---|---|---|---|---|---|---|---|---|---|
| \multicolumn{11}{c}{PDB FILE LISTING - cd811e1.pdb} |
| ATOM | 112 | CD1 | PHE | A | 126 | 14.372 | 40.659 | 16.802 | 1.00 | 24.92 | 6 |
| ATOM | 113 | CD2 | PHE | A | 126 | 12.201 | 41.422 | 17.567 | 1.00 | 24.93 | 6 |
| ATOM | 114 | CE1 | PHE | A | 126 | 14.990 | 41.588 | 17.628 | 1.00 | 28.09 | 6 |
| ATOM | 115 | CE2 | PHE | A | 126 | 12.844 | 42.353 | 18.368 | 1.00 | 21.69 | 6 |
| ATOM | 116 | CZ | PHE | A | 126 | 14.202 | 42.409 | 18.427 | 1.00 | 27.78 | 6 |
| ATOM | 117 | C | PHE | A | 126 | 11.592 | 38.131 | 17.688 | 1.00 | 21.94 | 6 |
| ATOM | 118 | O | PHE | A | 126 | 12.060 | 38.065 | 18.810 | 1.00 | 22.84 | 8 |
| ATOM | 119 | N | TYR | A | 127 | 10.246 | 38.180 | 17.534 | 1.00 | 19.86 | 7 |
| ATOM | 120 | CA | TYR | A | 127 | 9.349 | 38.135 | 18.698 | 1.00 | 20.03 | 6 |
| ATOM | 121 | CB | TYR | A | 127 | 7.865 | 38.224 | 18.184 | 1.00 | 23.84 | 6 |
| ATOM | 122 | CG | TYR | A | 127 | 6.918 | 37.987 | 19.351 | 1.00 | 21.94 | 6 |
| ATOM | 123 | CD1 | TYR | A | 127 | 6.577 | 38.925 | 20.305 | 1.00 | 21.20 | 6 |
| ATOM | 124 | CE1 | TYR | A | 127 | 5.735 | 38.634 | 21.368 | 1.00 | 17.80 | 6 |
| ATOM | 125 | CD2 | TYR | A | 127 | 6.394 | 36.687 | 19.461 | 1.00 | 21.35 | 6 |
| ATOM | 126 | CE2 | TYR | A | 127 | 5.542 | 36.351 | 20.521 | 1.00 | 23.38 | 6 |
| ATOM | 127 | CZ | TYR | A | 127 | 5.221 | 37.318 | 21.444 | 1.00 | 22.17 | 6 |
| ATOM | 128 | OH | TYR | A | 127 | 4.376 | 36.942 | 22.471 | 1.00 | 22.46 | 8 |
| ATOM | 129 | C | TYR | A | 127 | 9.552 | 36.818 | 19.437 | 1.00 | 18.72 | 6 |
| ATOM | 130 | O | TYR | A | 127 | 9.655 | 36.851 | 20.694 | 1.00 | 21.79 | 8 |
| ATOM | 131 | N | ASP | A | 128 | 9.606 | 35.711 | 18.693 | 1.00 | 23.27 | 7 |
| ATOM | 132 | CA | ASP | A | 128 | 9.726 | 34.407 | 19.418 | 1.00 | 22.55 | 6 |
| ATOM | 133 | CB | ASP | A | 128 | 9.674 | 33.283 | 18.359 | 1.00 | 25.98 | 6 |
| ATOM | 134 | CG | ASP | A | 128 | 8.249 | 33.014 | 17.910 | 1.00 | 29.92 | 6 |
| ATOM | 135 | OD1 | ASP | A | 128 | 8.110 | 32.180 | 16.988 | 1.00 | 32.49 | 8 |
| ATOM | 136 | OD2 | ASP | A | 128 | 7.294 | 33.586 | 18.464 | 1.00 | 27.69 | 8 |
| ATOM | 137 | C | ASP | A | 128 | 11.093 | 34.278 | 20.077 | 1.00 | 24.19 | 6 |
| ATOM | 138 | O | ASP | A | 128 | 11.158 | 33.755 | 21.208 | 1.00 | 22.87 | 8 |
| ATOM | 139 | N | GLN | A | 129 | 12.140 | 34.817 | 19.447 | 1.00 | 22.82 | 7 |
| ATOM | 140 | CA | GLN | A | 129 | 13.441 | 34.812 | 20.158 | 1.00 | 22.77 | 6 |
| ATOM | 141 | CB | GLN | A | 129 | 14.505 | 35.588 | 19.324 | 1.00 | 25.03 | 6 |
| ATOM | 142 | CG | GLN | A | 129 | 14.771 | 34.862 | 18.042 | 1.00 | 25.57 | 6 |
| ATOM | 143 | CD | GLN | A | 129 | 15.665 | 35.668 | 17.072 | 1.00 | 26.40 | 6 |
| ATOM | 144 | OE1 | GLN | A | 129 | 15.978 | 35.087 | 16.038 | 1.00 | 30.69 | 8 |
| ATOM | 145 | NE2 | GLN | A | 129 | 15.991 | 36.913 | 17.459 | 1.00 | 30.93 | 7 |
| ATOM | 146 | C | GLN | A | 129 | 13.299 | 35.632 | 21.434 | 1.00 | 22.40 | 6 |
| ATOM | 147 | O | GLN | A | 129 | 13.819 | 35.202 | 22.487 | 1.00 | 25.02 | 8 |
| ATOM | 148 | N | ALA | A | 130 | 12.695 | 36.829 | 21.395 | 1.00 | 20.16 | 7 |
| ATOM | 149 | CA | ALA | A | 130 | 12.602 | 37.564 | 22.647 | 1.00 | 19.19 | 6 |
| ATOM | 150 | CB | ALA | A | 130 | 12.049 | 39.003 | 22.397 | 1.00 | 21.18 | 6 |
| ATOM | 151 | C | ALA | A | 130 | 11.791 | 36.880 | 23.687 | 1.00 | 22.54 | 6 |
| ATOM | 152 | O | ALA | A | 130 | 12.047 | 36.945 | 24.912 | 1.00 | 22.88 | 8 |
| ATOM | 153 | N | LEU | A | 131 | 10.655 | 36.253 | 23.276 | 1.00 | 18.79 | 7 |
| ATOM | 154 | CA | LEU | A | 131 | 9.742 | 35.645 | 24.266 | 1.00 | 21.57 | 6 |
| ATOM | 155 | CB | LEU | A | 131 | 8.492 | 35.127 | 23.523 | 1.00 | 21.87 | 6 |
| ATOM | 156 | CG | LEU | A | 131 | 7.340 | 34.780 | 24.516 | 1.00 | 26.58 | 6 |
| ATOM | 157 | CD1 | LEU | A | 131 | 6.825 | 36.097 | 25.128 | 1.00 | 24.19 | 6 |
| ATOM | 158 | CD2 | LEU | A | 131 | 6.209 | 34.116 | 23.747 | 1.00 | 23.85 | 6 |
| ATOM | 159 | C | LEU | A | 131 | 10.454 | 34.451 | 24.948 | 1.00 | 21.60 | 6 |
| ATOM | 160 | O | LEU | A | 131 | 10.320 | 34.274 | 26.150 | 1.00 | 22.16 | 8 |
| ATOM | 161 | N | GLN | A | 132 | 11.181 | 33.692 | 24.137 | 1.00 | 22.17 | 7 |
| ATOM | 162 | CA | GLN | A | 132 | 11.884 | 32.531 | 24.707 | 1.00 | 23.12 | 6 |
| ATOM | 163 | CB | GLN | A | 132 | 12.508 | 31.669 | 23.581 | 1.00 | 22.76 | 6 |
| ATOM | 164 | CG | GLN | A | 132 | 11.381 | 30.963 | 22.796 | 1.00 | 24.05 | 6 |
| ATOM | 165 | CD | GLN | A | 132 | 11.961 | 30.193 | 21.606 | 1.00 | 25.65 | 6 |
| ATOM | 166 | OE1 | GLN | A | 132 | 11.936 | 28.946 | 21.582 | 1.00 | 28.29 | 8 |
| ATOM | 167 | NE2 | GLN | A | 132 | 12.428 | 30.852 | 20.541 | 1.00 | 25.24 | 7 |
| ATOM | 168 | C | GLN | A | 132 | 12.922 | 32.987 | 25.692 | 1.00 | 22.26 | 6 |
| ATOM | 169 | O | GLN | A | 132 | 13.006 | 32.389 | 26.770 | 1.00 | 23.25 | 8 |
| ATOM | 170 | N | GLN | A | 133 | 13.693 | 34.050 | 25.412 | 1.00 | 21.14 | 7 |
| ATOM | 171 | CA | GLN | A | 133 | 14.711 | 34.509 | 26.348 | 1.00 | 21.05 | 6 |
| ATOM | 172 | CB | GLN | A | 133 | 15.533 | 35.610 | 25.619 | 1.00 | 22.48 | 6 |
| ATOM | 173 | CG | GLN | A | 133 | 16.687 | 35.994 | 26.548 | 1.00 | 25.57 | 6 |
| ATOM | 174 | CD | GLN | A | 133 | 17.650 | 36.993 | 25.926 | 1.00 | 23.61 | 6 |
| ATOM | 175 | OE1 | GLN | A | 133 | 17.463 | 37.432 | 24.806 | 1.00 | 28.80 | 8 |
| ATOM | 176 | NE2 | GLN | A | 133 | 18.726 | 37.251 | 26.669 | 1.00 | 29.55 | 7 |
| ATOM | 177 | C | GLN | A | 133 | 14.070 | 35.146 | 27.572 | 1.00 | 22.02 | 6 |
| ATOM | 178 | O | GLN | A | 133 | 14.481 | 34.985 | 28.734 | 1.00 | 24.53 | 8 |
| ATOM | 179 | N | ALA | A | 134 | 12.946 | 35.879 | 27.368 | 1.00 | 22.25 | 7 |
| ATOM | 180 | CA | ALA | A | 134 | 12.270 | 36.531 | 28.489 | 1.00 | 24.32 | 6 |
| ATOM | 181 | CB | ALA | A | 134 | 11.058 | 37.332 | 27.987 | 1.00 | 24.55 | 6 |
| ATOM | 182 | C | ALA | A | 134 | 11.798 | 35.628 | 29.623 | 1.00 | 23.77 | 6 |
| ATOM | 183 | O | ALA | A | 134 | 11.708 | 35.947 | 30.819 | 1.00 | 27.92 | 8 |
| ATOM | 184 | N | VAL | A | 135 | 11.447 | 34.399 | 29.250 | 1.00 | 22.81 | 7 |
| ATOM | 185 | CA | VAL | A | 135 | 10.918 | 33.425 | 30.203 | 1.00 | 22.24 | 6 |
| ATOM | 186 | CB | VAL | A | 135 | 9.948 | 32.446 | 29.546 | 1.00 | 31.11 | 6 |
| ATOM | 187 | CG1 | VAL | A | 135 | 8.682 | 33.122 | 29.084 | 1.00 | 29.66 | 6 |
| ATOM | 188 | CG2 | VAL | A | 135 | 10.546 | 31.496 | 28.557 | 1.00 | 45.64 | 6 |

-continued

PDB FILE LISTING - cd811e1.pdb

| | | | | | | | | | | |
|---|---|---|---|---|---|---|---|---|---|---|
| ATOM | 189 | C | VAL | A | 135 | 12.043 | 32.676 | 30.843 | 1.00 | 25.73 | 6 |
| ATOM | 190 | O | VAL | A | 135 | 11.880 | 32.216 | 31.986 | 1.00 | 31.63 | 8 |
| ATOM | 191 | N | VAL | A | 136 | 13.147 | 32.472 | 30.135 | 1.00 | 30.36 | 7 |
| ATOM | 192 | CA | VAL | A | 136 | 14.211 | 31.649 | 30.768 | 1.00 | 29.23 | 6 |
| ATOM | 193 | CB | VAL | A | 136 | 14.704 | 30.717 | 29.663 | 1.00 | 30.54 | 6 |
| ATOM | 194 | CG1 | VAL | A | 136 | 15.653 | 31.427 | 28.727 | 1.00 | 28.12 | 6 |
| ATOM | 195 | CG2 | VAL | A | 136 | 15.237 | 29.401 | 30.184 | 1.00 | 33.07 | 6 |
| ATOM | 196 | C | VAL | A | 136 | 15.274 | 32.433 | 31.445 | 1.00 | 32.01 | 6 |
| ATOM | 197 | O | VAL | A | 136 | 16.080 | 31.921 | 32.242 | 1.00 | 35.58 | 8 |
| ATOM | 198 | N | ASP | A | 137 | 15.520 | 33.683 | 31.050 | 1.00 | 29.34 | 7 |
| ATOM | 199 | CA | ASP | A | 137 | 16.647 | 34.496 | 31.487 | 1.00 | 30.00 | 6 |
| ATOM | 200 | CB | ASP | A | 137 | 17.273 | 35.171 | 30.263 | 1.00 | 31.01 | 6 |
| ATOM | 201 | CG | ASP | A | 137 | 18.536 | 35.952 | 30.547 | 1.00 | 38.12 | 6 |
| ATOM | 202 | OD1 | ASP | A | 137 | 19.181 | 36.426 | 29.580 | 1.00 | 33.65 | 8 |
| ATOM | 203 | OD2 | ASP | A | 137 | 18.933 | 36.171 | 31.710 | 1.00 | 34.77 | 8 |
| ATOM | 204 | C | ASP | A | 137 | 16.127 | 35.551 | 32.450 | 1.00 | 35.73 | 6 |
| ATOM | 205 | O | ASP | A | 137 | 15.411 | 36.471 | 32.043 | 1.00 | 35.33 | 8 |
| ATOM | 206 | N | ASP | A | 138 | 16.486 | 35.444 | 33.718 | 1.00 | 41.35 | 7 |
| ATOM | 207 | CA | ASP | A | 138 | 16.026 | 36.345 | 34.735 | 1.00 | 44.53 | 6 |
| ATOM | 208 | CB | ASP | A | 138 | 16.349 | 35.881 | 36.159 | 1.00 | 55.88 | 6 |
| ATOM | 209 | CG | ASP | A | 138 | 14.551 | 35.422 | 36.525 | 0.00 | 27.18 | 6 |
| ATOM | 210 | OD1 | ASP | A | 138 | 14.174 | 34.275 | 36.165 | 0.00 | 27.18 | 8 |
| ATOM | 211 | OD2 | ASP | A | 138 | 13.773 | 36.235 | 37.082 | 0.00 | 27.18 | 8 |
| ATOM | 212 | C | ASP | A | 138 | 16.457 | 37.783 | 34.550 | 1.00 | 45.63 | 6 |
| ATOM | 213 | O | ASP | A | 138 | 15.642 | 38.619 | 34.905 | 1.00 | 46.37 | 8 |
| ATOM | 214 | N | ASP | A | 139 | 17.659 | 38.047 | 34.046 | 1.00 | 47.04 | 7 |
| ATOM | 215 | CA | ASP | A | 139 | 18.045 | 39.434 | 33.860 | 1.00 | 47.12 | 6 |
| ATOM | 216 | CB | ASP | A | 139 | 19.315 | 39.889 | 34.534 | 1.00 | 59.30 | 6 |
| ATOM | 217 | CG | ASP | A | 139 | 20.138 | 38.776 | 35.141 | 1.00 | 60.21 | 6 |
| ATOM | 218 | OD1 | ASP | A | 139 | 20.667 | 37.956 | 34.371 | 1.00 | 66.48 | 8 |
| ATOM | 219 | OD2 | ASP | A | 139 | 20.245 | 38.739 | 36.381 | 1.00 | 60.42 | 8 |
| ATOM | 220 | C | ASP | A | 139 | 17.980 | 39.852 | 32.397 | 1.00 | 44.11 | 6 |
| ATOM | 221 | O | ASP | A | 139 | 18.684 | 40.814 | 32.054 | 1.00 | 45.91 | 8 |
| ATOM | 222 | N | ALA | A | 140 | 17.165 | 39.159 | 31.588 | 1.00 | 36.40 | 7 |
| ATOM | 223 | CA | ALA | A | 140 | 17.097 | 39.640 | 30.176 | 1.00 | 34.34 | 6 |
| ATOM | 224 | CB | ALA | A | 140 | 16.549 | 38.514 | 29.305 | 1.00 | 29.85 | 6 |
| ATOM | 225 | C | ALA | A | 140 | 16.124 | 40.801 | 30.144 | 1.00 | 29.56 | 6 |
| ATOM | 226 | O | ALA | A | 140 | 14.956 | 40.665 | 29.725 | 1.00 | 28.22 | 8 |
| ATOM | 227 | N | ASN | A | 141 | 16.528 | 41.977 | 30.625 | 1.00 | 29.81 | 7 |
| ATOM | 228 | CA | ASN | A | 141 | 15.623 | 43.101 | 30.725 | 1.00 | 30.52 | 6 |
| ATOM | 229 | CB | ASN | A | 141 | 16.336 | 44.264 | 31.435 | 1.00 | 37.01 | 6 |
| ATOM | 230 | CG | ASN | A | 141 | 16.696 | 43.864 | 32.857 | 1.00 | 54.30 | 6 |
| ATOM | 231 | OD1 | ASN | A | 141 | 15.795 | 43.768 | 33.690 | 1.00 | 48.05 | 8 |
| ATOM | 232 | ND2 | ASN | A | 141 | 17.991 | 43.645 | 33.062 | 1.00 | 56.03 | 7 |
| ATOM | 233 | C | ASN | A | 141 | 15.225 | 43.622 | 29.319 | 1.00 | 25.07 | 6 |
| ATOM | 234 | O | ASN | A | 141 | 14.036 | 43.975 | 29.220 | 1.00 | 30.82 | 8 |
| ATOM | 235 | N | ASN | A | 142 | 16.189 | 43.580 | 28.407 | 1.00 | 32.80 | 7 |
| ATOM | 236 | CA | ASN | A | 142 | 15.802 | 44.039 | 27.068 | 1.00 | 27.52 | 6 |
| ATOM | 237 | CB | ASN | A | 142 | 16.955 | 44.259 | 26.125 | 1.00 | 32.75 | 6 |
| ATOM | 238 | CG | ASN | A | 142 | 17.649 | 45.601 | 26.305 | 1.00 | 52.93 | 6 |
| ATOM | 239 | OD1 | ASN | A | 142 | 18.857 | 45.697 | 26.058 | 1.00 | 59.14 | 8 |
| ATOM | 240 | ND2 | ASN | A | 142 | 16.922 | 46.626 | 26.735 | 1.00 | 57.80 | 7 |
| ATOM | 241 | C | ASN | A | 142 | 14.791 | 43.064 | 26.464 | 1.00 | 25.36 | 6 |
| ATOM | 242 | O | ASN | A | 142 | 13.788 | 43.551 | 25.878 | 1.00 | 26.29 | 8 |
| ATOM | 243 | N | ALA | A | 143 | 15.035 | 41.759 | 26.593 | 1.00 | 23.53 | 7 |
| ATOM | 244 | CA | ALA | A | 143 | 14.041 | 40.835 | 26.012 | 1.00 | 25.47 | 6 |
| ATOM | 245 | CB | ALA | A | 143 | 14.443 | 39.375 | 26.206 | 1.00 | 22.30 | 6 |
| ATOM | 246 | C | ALA | A | 143 | 12.661 | 41.003 | 26.568 | 1.00 | 24.29 | 6 |
| ATOM | 247 | O | ALA | A | 143 | 11.612 | 40.989 | 25.897 | 1.00 | 22.58 | 8 |
| ATOM | 248 | N | LYS | A | 144 | 12.519 | 41.185 | 27.922 | 1.00 | 21.87 | 7 |
| ATOM | 249 | CA | LYS | A | 144 | 11.258 | 41.408 | 28.541 | 1.00 | 20.70 | 6 |
| ATOM | 250 | CB | LYS | A | 144 | 11.375 | 41.391 | 30.083 | 1.00 | 28.64 | 6 |
| ATOM | 251 | CG | LYS | A | 144 | 11.856 | 40.022 | 30.597 | 1.00 | 26.79 | 6 |
| ATOM | 252 | CD | LYS | A | 144 | 12.210 | 40.226 | 32.089 | 1.00 | 31.38 | 6 |
| ATOM | 253 | CE | LYS | A | 144 | 13.007 | 39.023 | 32.585 | 1.00 | 45.61 | 6 |
| ATOM | 254 | NZ | LYS | A | 144 | 12.035 | 37.945 | 32.966 | 1.00 | 43.86 | 7 |
| ATOM | 255 | C | LYS | A | 144 | 10.663 | 42.717 | 28.045 | 1.00 | 19.65 | 6 |
| ATOM | 256 | O | LYS | A | 144 | 9.472 | 42.704 | 27.782 | 1.00 | 24.45 | 8 |
| ATOM | 257 | N | ALA | A | 145 | 11.500 | 43.758 | 27.888 | 1.00 | 22.72 | 7 |
| ATOM | 258 | CA | ALA | A | 145 | 10.889 | 45.019 | 27.383 | 1.00 | 24.10 | 6 |
| ATOM | 259 | CB | ALA | A | 145 | 11.949 | 46.097 | 27.451 | 1.00 | 23.70 | 6 |
| ATOM | 260 | C | ALA | A | 145 | 10.430 | 44.868 | 25.914 | 1.00 | 21.09 | 6 |
| ATOM | 261 | O | ALA | A | 145 | 9.302 | 45.355 | 25.644 | 1.00 | 21.56 | 8 |
| ATOM | 262 | N | VAL | A | 146 | 11.171 | 44.078 | 25.189 | 1.00 | 22.29 | 7 |
| ATOM | 263 | CA | VAL | A | 146 | 10.683 | 43.855 | 23.784 | 1.00 | 20.84 | 6 |
| ATOM | 264 | CB | VAL | A | 146 | 11.731 | 43.079 | 22.976 | 1.00 | 22.15 | 6 |
| ATOM | 265 | CG1 | VAL | A | 146 | 11.112 | 42.478 | 21.711 | 1.00 | 23.27 | 6 |

-continued

PDB FILE LISTING - cd811e1.pdb

| ATOM | 266 | CG2 | VAL | A | 146 | 12.898 | 44.014 | 22.734 | 1.00 | 22.16 | 6 |
|---|---|---|---|---|---|---|---|---|---|---|---|
| ATOM | 267 | C | VAL | A | 146 | 9.361 | 43.149 | 23.742 | 1.00 | 19.58 | 6 |
| ATOM | 268 | O | VAL | A | 146 | 8.394 | 43.563 | 23.088 | 1.00 | 21.79 | 8 |
| ATOM | 269 | N | VAL | A | 147 | 9.239 | 42.066 | 24.552 | 1.00 | 19.17 | 7 |
| ATOM | 270 | CA | VAL | A | 147 | 7.968 | 41.312 | 24.548 | 1.00 | 19.64 | 6 |
| ATOM | 271 | CB | VAL | A | 147 | 8.263 | 40.138 | 25.586 | 1.00 | 23.25 | 6 |
| ATOM | 272 | CG1 | VAL | A | 147 | 7.102 | 39.633 | 26.344 | 1.00 | 36.08 | 6 |
| ATOM | 273 | CG2 | VAL | A | 147 | 8.943 | 39.101 | 24.664 | 1.00 | 32.42 | 6 |
| ATOM | 274 | C | VAL | A | 147 | 6.844 | 42.194 | 25.068 | 1.00 | 20.95 | 6 |
| ATOM | 275 | O | VAL | A | 147 | 5.742 | 42.204 | 24.529 | 1.00 | 21.71 | 8 |
| ATOM | 276 | N | LYS | A | 148 | 7.072 | 42.924 | 26.178 | 1.00 | 19.59 | 7 |
| ATOM | 277 | CA | LYS | A | 148 | 5.979 | 43.783 | 26.688 | 1.00 | 21.04 | 6 |
| ATOM | 278 | CB | LYS | A | 148 | 6.499 | 44.431 | 27.981 | 1.00 | 26.20 | 6 |
| ATOM | 279 | CG | LYS | A | 148 | 6.574 | 43.388 | 29.093 | 1.00 | 27.82 | 6 |
| ATOM | 280 | CD | LYS | A | 148 | 6.786 | 44.057 | 30.419 | 1.00 | 30.78 | 6 |
| ATOM | 281 | CE | LYS | A | 148 | 8.007 | 44.919 | 30.523 | 1.00 | 46.34 | 6 |
| ATOM | 282 | NZ | LYS | A | 148 | 8.210 | 45.450 | 31.917 | 1.00 | 44.31 | 7 |
| ATOM | 283 | C | LYS | A | 148 | 5.564 | 44.894 | 25.702 | 1.00 | 20.08 | 6 |
| ATOM | 284 | O | LYS | A | 148 | 4.365 | 45.111 | 25.584 | 1.00 | 23.45 | 8 |
| ATOM | 285 | N | THR | A | 149 | 6.509 | 45.375 | 24.919 | 1.00 | 22.66 | 7 |
| ATOM | 286 | CA | THR | A | 149 | 6.199 | 46.426 | 23.955 | 1.00 | 24.54 | 6 |
| ATOM | 287 | CB | THR | A | 149 | 7.501 | 46.993 | 23.359 | 1.00 | 28.59 | 6 |
| ATOM | 288 | OG1 | THR | A | 149 | 8.175 | 47.743 | 24.398 | 1.00 | 27.03 | 8 |
| ATOM | 289 | CG2 | THR | A | 149 | 7.137 | 47.974 | 22.239 | 1.00 | 26.03 | 6 |
| ATOM | 290 | C | THR | A | 149 | 5.444 | 45.829 | 22.784 | 1.00 | 22.31 | 6 |
| ATOM | 291 | O | THR | A | 149 | 4.445 | 46.365 | 22.357 | 1.00 | 23.09 | 8 |
| ATOM | 292 | N | PHE | A | 150 | 5.840 | 44.627 | 22.338 | 1.00 | 20.35 | 7 |
| ATOM | 293 | CA | PHE | A | 150 | 5.032 | 43.967 | 21.295 | 1.00 | 20.84 | 6 |
| ATOM | 294 | CB | PHE | A | 150 | 5.656 | 42.622 | 20.813 | 1.00 | 19.43 | 6 |
| ATOM | 295 | CG | PHE | A | 150 | 6.572 | 42.840 | 19.638 | 1.00 | 19.28 | 6 |
| ATOM | 296 | CD1 | PHE | A | 150 | 7.767 | 43.517 | 19.804 | 1.00 | 23.21 | 6 |
| ATOM | 297 | CD2 | PHE | A | 150 | 6.223 | 42.279 | 18.424 | 1.00 | 22.14 | 6 |
| ATOM | 298 | CE1 | PHE | A | 150 | 8.628 | 43.662 | 18.709 | 1.00 | 24.38 | 6 |
| ATOM | 299 | CE2 | PHE | A | 150 | 7.090 | 42.460 | 17.318 | 1.00 | 26.48 | 6 |
| ATOM | 300 | CZ | PHE | A | 150 | 8.274 | 43.138 | 17.487 | 1.00 | 26.64 | 6 |
| ATOM | 301 | C | PHE | A | 150 | 3.639 | 43.730 | 21.816 | 1.00 | 21.43 | 6 |
| ATOM | 302 | O | PHE | A | 150 | 2.641 | 43.978 | 21.161 | 1.00 | 22.18 | 8 |
| ATOM | 303 | N | HIS | A | 151 | 3.492 | 43.160 | 23.052 | 1.00 | 19.41 | 7 |
| ATOM | 304 | CA | HIS | A | 151 | 2.136 | 42.899 | 23.534 | 1.00 | 20.29 | 6 |
| ATOM | 305 | CB | HIS | A | 151 | 2.327 | 42.196 | 24.892 | 1.00 | 20.50 | 6 |
| ATOM | 306 | CG | HIS | A | 151 | 2.926 | 40.818 | 24.756 | 1.00 | 19.00 | 6 |
| ATOM | 307 | CD2 | HIS | A | 151 | 3.109 | 39.943 | 23.786 | 1.00 | 21.53 | 6 |
| ATOM | 308 | ND1 | HIS | A | 151 | 3.430 | 40.277 | 25.923 | 1.00 | 24.13 | 7 |
| ATOM | 309 | CE1 | HIS | A | 151 | 3.844 | 39.057 | 25.645 | 1.00 | 22.94 | 6 |
| ATOM | 310 | NE2 | HIS | A | 151 | 3.714 | 38.809 | 24.336 | 1.00 | 23.76 | 7 |
| ATOM | 311 | C | HIS | A | 151 | 1.264 | 44.140 | 23.689 | 1.00 | 17.69 | 6 |
| ATOM | 312 | O | HIS | A | 151 | 0.092 | 44.031 | 23.367 | 1.00 | 20.84 | 8 |
| ATOM | 313 | N | GLU | A | 152 | 1.799 | 45.257 | 24.154 | 1.00 | 20.91 | 7 |
| ATOM | 314 | CA | GLU | A | 152 | 0.990 | 46.458 | 24.397 | 1.00 | 21.45 | 6 |
| ATOM | 315 | CB | GLU | A | 152 | 1.887 | 47.401 | 25.181 | 1.00 | 24.45 | 6 |
| ATOM | 316 | CG | GLU | A | 152 | 1.146 | 48.737 | 25.465 | 1.00 | 35.51 | 6 |
| ATOM | 317 | CD | GLU | A | 152 | 1.910 | 49.450 | 26.575 | 1.00 | 37.49 | 6 |
| ATOM | 318 | OE1 | GLU | A | 152 | 3.012 | 49.946 | 26.243 | 1.00 | 60.98 | 8 |
| ATOM | 319 | OE2 | GLU | A | 152 | 1.409 | 49.523 | 27.706 | 1.00 | 54.52 | 8 |
| ATOM | 320 | C | GLU | A | 152 | 0.652 | 47.073 | 23.016 | 1.00 | 24.93 | 6 |
| ATOM | 321 | O | GLU | A | 152 | −0.516 | 47.374 | 22.677 | 1.00 | 26.68 | 8 |
| ATOM | 322 | N | THR | A | 153 | 1.679 | 47.050 | 22.170 | 1.00 | 22.06 | 7 |
| ATOM | 323 | CA | THR | A | 153 | 1.553 | 47.631 | 20.837 | 1.00 | 23.76 | 6 |
| ATOM | 324 | CB | THR | A | 153 | 2.877 | 47.930 | 20.167 | 1.00 | 22.41 | 6 |
| ATOM | 325 | OG1 | THR | A | 153 | 3.719 | 48.778 | 20.982 | 1.00 | 25.19 | 8 |
| ATOM | 326 | CG2 | THR | A | 153 | 2.706 | 48.553 | 18.778 | 1.00 | 26.00 | 6 |
| ATOM | 327 | C | THR | A | 153 | 0.543 | 46.956 | 19.957 | 1.00 | 25.16 | 6 |
| ATOM | 328 | O | THR | A | 153 | −0.255 | 47.624 | 19.292 | 1.00 | 27.39 | 8 |
| ATOM | 329 | N | LEU | A | 154 | 0.581 | 45.631 | 19.880 | 1.00 | 24.12 | 7 |
| ATOM | 330 | CA | LEU | A | 154 | −0.293 | 44.865 | 19.028 | 1.00 | 24.17 | 6 |
| ATOM | 331 | CB | LEU | A | 154 | 0.475 | 43.699 | 18.382 | 1.00 | 24.04 | 6 |
| ATOM | 332 | CG | LEU | A | 154 | 1.735 | 44.158 | 17.692 | 1.00 | 23.64 | 6 |
| ATOM | 333 | CD1 | LEU | A | 154 | 2.505 | 42.926 | 17.202 | 1.00 | 28.71 | 6 |
| ATOM | 334 | CD2 | LEU | A | 154 | 1.410 | 45.020 | 16.462 | 1.00 | 27.37 | 6 |
| ATOM | 335 | C | LEU | A | 154 | −1.519 | 44.271 | 19.703 | 1.00 | 25.12 | 6 |
| ATOM | 336 | O | LEU | A | 154 | −2.253 | 43.539 | 19.036 | 1.00 | 30.55 | 8 |
| ATOM | 337 | N | ASP | A | 155 | −1.650 | 44.490 | 20.998 | 1.00 | 24.04 | 7 |
| ATOM | 338 | CA | ASP | A | 155 | −2.798 | 43.983 | 21.753 | 1.00 | 26.79 | 6 |
| ATOM | 339 | CB | ASP | A | 155 | −4.088 | 44.595 | 21.191 | 1.00 | 29.32 | 6 |
| ATOM | 340 | CG | ASP | A | 155 | −5.288 | 44.195 | 22.049 | 1.00 | 54.63 | 6 |
| ATOM | 341 | OD1 | ASP | A | 155 | −6.418 | 44.190 | 21.500 | 1.00 | 39.24 | 8 |
| ATOM | 342 | OD2 | ASP | A | 155 | −5.082 | 43.899 | 23.250 | 1.00 | 34.92 | 8 |

-continued

| PDB FILE LISTING - cd811e1.pdb | | | | | | | | | | |
|---|---|---|---|---|---|---|---|---|---|---|
| ATOM | 343 | C | ASP | A | 155 | −2.830 | 42.462 | 21.694 | 1.00 | 30.04 | 6 |
| ATOM | 344 | O | ASP | A | 155 | −3.750 | 41.884 | 21.134 | 1.00 | 29.77 | 8 |
| ATOM | 345 | N | CYS | A | 156 | −1.738 | 41.816 | 22.153 | 1.00 | 25.38 | 7 |
| ATOM | 346 | CA | CYS | A | 156 | −1.681 | 40.340 | 22.082 | 1.00 | 25.86 | 6 |
| ATOM | 347 | C | CYS | A | 156 | −0.797 | 39.854 | 23.234 | 1.00 | 26.35 | 6 |
| ATOM | 348 | O | CYS | A | 156 | −0.269 | 40.677 | 24.000 | 1.00 | 26.19 | 8 |
| ATOM | 349 | CB | CYS | A | 156 | −1.078 | 39.839 | 20.742 | 1.00 | 27.96 | 6 |
| ATOM | 350 | SG | CYS | A | 156 | 0.624 | 40.419 | 20.466 | 1.00 | 24.36 | 16 |
| ATOM | 351 | N | CYS | A | 157 | −0.843 | 38.518 | 23.399 | 1.00 | 26.36 | 7 |
| ATOM | 352 | CA | CYS | A | 157 | −0.036 | 37.954 | 24.518 | 1.00 | 27.31 | 6 |
| ATOM | 353 | C | CYS | A | 157 | 0.314 | 36.526 | 24.086 | 1.00 | 24.36 | 6 |
| ATOM | 354 | O | CYS | A | 157 | −0.521 | 35.614 | 23.957 | 1.00 | 27.45 | 8 |
| ATOM | 355 | CB | CYS | A | 157 | −0.965 | 37.922 | 25.747 | 1.00 | 33.17 | 6 |
| ATOM | 356 | SG | CYS | A | 157 | −0.201 | 37.056 | 27.129 | 1.00 | 32.57 | 16 |
| ATOM | 357 | N | GLY | A | 158 | 1.578 | 36.266 | 23.759 | 1.00 | 23.62 | 7 |
| ATOM | 358 | CA | GLY | A | 158 | 1.997 | 34.967 | 23.282 | 1.00 | 23.46 | 6 |
| ATOM | 359 | C | GLY | A | 158 | 1.882 | 34.721 | 21.802 | 1.00 | 24.98 | 6 |
| ATOM | 360 | O | GLY | A | 158 | 1.347 | 35.496 | 21.016 | 1.00 | 30.72 | 8 |
| ATOM | 361 | N | SER | A | 159 | 2.419 | 33.571 | 21.340 | 1.00 | 23.28 | 7 |
| ATOM | 362 | CA | SER | A | 159 | 2.365 | 33.214 | 19.927 | 1.00 | 25.33 | 6 |
| ATOM | 363 | CB | SER | A | 159 | 3.627 | 33.414 | 19.111 | 1.00 | 37.04 | 6 |
| ATOM | 364 | OG | SER | A | 159 | 4.687 | 32.681 | 19.726 | 1.00 | 32.95 | 8 |
| ATOM | 365 | C | SER | A | 159 | 1.906 | 31.752 | 19.744 | 1.00 | 29.87 | 8 |
| ATOM | 366 | O | SER | A | 159 | 2.043 | 30.944 | 20.645 | 1.00 | 28.52 | 8 |
| ATOM | 367 | N | SER | A | 160 | 1.525 | 31.513 | 18.498 | 1.00 | 28.89 | 7 |
| ATOM | 368 | CA | SER | A | 160 | 1.020 | 30.167 | 18.155 | 1.00 | 31.12 | 6 |
| ATOM | 369 | CB | SER | A | 160 | 0.229 | 30.282 | 16.851 | 1.00 | 29.35 | 6 |
| ATOM | 370 | OG | SER | A | 160 | 0.979 | 30.793 | 15.778 | 1.00 | 39.68 | 8 |
| ATOM | 371 | C | SER | A | 160 | 2.125 | 29.135 | 18.122 | 1.00 | 31.20 | 6 |
| ATOM | 372 | O | SER | A | 160 | 1.852 | 27.946 | 18.180 | 1.00 | 40.09 | 8 |
| ATOM | 373 | N | THR | A | 161 | 3.379 | 29.492 | 17.936 | 1.00 | 29.17 | 7 |
| ATOM | 374 | CA | THR | A | 161 | 4.535 | 28.620 | 17.923 | 1.00 | 31.95 | 6 |
| ATOM | 375 | CB | THR | A | 161 | 5.728 | 29.296 | 17.195 | 1.00 | 32.45 | 6 |
| ATOM | 376 | OG1 | THR | A | 161 | 5.881 | 30.601 | 17.775 | 1.00 | 30.29 | 8 |
| ATOM | 377 | CG2 | THR | A | 161 | 5.551 | 29.428 | 15.705 | 1.00 | 29.68 | 6 |
| ATOM | 378 | C | THR | A | 161 | 4.993 | 28.340 | 19.364 | 1.00 | 29.18 | 6 |
| ATOM | 379 | O | THR | A | 161 | 5.917 | 27.498 | 19.536 | 1.00 | 30.20 | 8 |
| ATOM | 380 | N | LEU | A | 162 | 4.419 | 29.014 | 20.331 | 1.00 | 25.69 | 7 |
| ATOM | 381 | CA | LEU | A | 162 | 4.856 | 28.893 | 21.717 | 1.00 | 27.41 | 6 |
| ATOM | 382 | CB | LEU | A | 162 | 5.756 | 30.118 | 22.008 | 1.00 | 23.42 | 6 |
| ATOM | 383 | CG | LEU | A | 162 | 7.098 | 30.162 | 21.291 | 1.00 | 24.84 | 6 |
| ATOM | 384 | CD1 | LEU | A | 162 | 7.779 | 31.516 | 21.585 | 1.00 | 23.56 | 6 |
| ATOM | 385 | CD2 | LEU | A | 162 | 8.040 | 29.030 | 21.756 | 1.00 | 25.57 | 6 |
| ATOM | 386 | C | LEU | A | 162 | 3.724 | 28.789 | 22.704 | 1.00 | 27.32 | 6 |
| ATOM | 387 | O | LEU | A | 162 | 3.776 | 29.267 | 23.841 | 1.00 | 25.57 | 8 |
| ATOM | 388 | N | THR | A | 163 | 2.651 | 28.111 | 22.252 | 1.00 | 33.24 | 7 |
| ATOM | 389 | CA | THR | A | 163 | 1.435 | 27.945 | 23.005 | 1.00 | 34.43 | 6 |
| ATOM | 390 | CB | THR | A | 163 | 0.321 | 27.242 | 22.231 | 1.00 | 47.90 | 6 |
| ATOM | 391 | OG1 | THR | A | 163 | 0.574 | 25.833 | 22.222 | 1.00 | 41.55 | 8 |
| ATOM | 392 | CG2 | THR | A | 163 | 0.333 | 27.684 | 20.769 | 1.00 | 37.28 | 6 |
| ATOM | 393 | C | THR | A | 163 | 1.633 | 27.365 | 24.386 | 1.00 | 33.67 | 6 |
| ATOM | 394 | O | THR | A | 163 | 1.027 | 27.836 | 25.334 | 1.00 | 37.42 | 8 |
| ATOM | 395 | N | ALA | A | 164 | 2.588 | 26.420 | 24.481 | 1.00 | 34.03 | 7 |
| ATOM | 396 | CA | ALA | A | 164 | 2.861 | 25.891 | 25.801 | 1.00 | 33.86 | 6 |
| ATOM | 397 | CB | ALA | A | 164 | 3.368 | 24.474 | 25.747 | 1.00 | 38.55 | 6 |
| ATOM | 398 | C | ALA | A | 164 | 3.581 | 26.799 | 26.735 | 1.00 | 34.37 | 6 |
| ATOM | 399 | O | ALA | A | 164 | 3.702 | 26.455 | 27.918 | 1.00 | 32.28 | 8 |
| ATOM | 400 | N | LEU | A | 165 | 4.067 | 27.970 | 26.286 | 1.00 | 33.08 | 7 |
| ATOM | 401 | CA | LEU | A | 165 | 4.711 | 28.931 | 27.152 | 1.00 | 31.61 | 6 |
| ATOM | 402 | CB | LEU | A | 165 | 5.768 | 29.707 | 26.306 | 1.00 | 27.45 | 6 |
| ATOM | 403 | CG | LEU | A | 165 | 7.210 | 29.476 | 26.442 | 1.00 | 27.02 | 6 |
| ATOM | 404 | CD1 | LEU | A | 165 | 8.028 | 30.517 | 25.763 | 1.00 | 24.12 | 6 |
| ATOM | 405 | CD2 | LEU | A | 165 | 7.803 | 28.611 | 27.487 | 1.00 | 27.64 | 6 |
| ATOM | 406 | C | LEU | A | 165 | 3.814 | 30.032 | 27.651 | 1.00 | 29.91 | 6 |
| ATOM | 407 | O | LEU | A | 165 | 4.166 | 30.745 | 28.591 | 1.00 | 31.12 | 8 |
| ATOM | 408 | N | THR | A | 166 | 2.565 | 30.108 | 27.104 | 1.00 | 32.70 | 7 |
| ATOM | 409 | CA | THR | A | 166 | 1.679 | 31.174 | 27.587 | 1.00 | 39.86 | 6 |
| ATOM | 410 | CB | THR | A | 166 | 0.417 | 31.275 | 26.724 | 1.00 | 36.59 | 6 |
| ATOM | 411 | OG1 | THR | A | 166 | 0.772 | 31.283 | 25.342 | 1.00 | 36.37 | 8 |
| ATOM | 412 | CG2 | THR | A | 166 | −0.426 | 32.496 | 27.035 | 1.00 | 43.25 | 6 |
| ATOM | 413 | C | THR | A | 166 | 1.507 | 31.273 | 29.078 | 1.00 | 40.96 | 6 |
| ATOM | 414 | O | THR | A | 166 | 1.550 | 32.372 | 29.663 | 1.00 | 38.71 | 8 |
| ATOM | 415 | N | THR | A | 167 | 1.389 | 30.162 | 29.818 | 1.00 | 41.60 | 7 |
| ATOM | 416 | CA | THR | A | 167 | 1.264 | 30.185 | 31.258 | 1.00 | 41.06 | 6 |
| ATOM | 417 | CB | THR | A | 167 | 1.145 | 28.770 | 31.877 | 1.00 | 56.92 | 6 |
| ATOM | 418 | OG1 | THR | A | 167 | 0.505 | 27.882 | 30.956 | 1.00 | 64.37 | 8 |
| ATOM | 419 | CG2 | THR | A | 167 | 0.315 | 28.860 | 33.144 | 1.00 | 53.26 | 6 |

-continued

| PDB FILE LISTING - cd811e1.pdb | | | | | | | | | | |
|---|---|---|---|---|---|---|---|---|---|---|
| ATOM | 420 | C | THR | A | 167 | 2.386 | 30.920 | 31.965 | 1.00 | 38.21 | 6 |
| ATOM | 421 | O | THR | A | 167 | 2.297 | 31.748 | 32.872 | 1.00 | 38.00 | 8 |
| ATOM | 422 | N | SER | A | 168 | 3.588 | 30.592 | 31.464 | 1.00 | 36.02 | 7 |
| ATOM | 423 | CA | SER | A | 168 | 4.823 | 31.175 | 31.912 | 1.00 | 32.03 | 6 |
| ATOM | 424 | CB | SER | A | 168 | 5.950 | 30.393 | 31.219 | 1.00 | 39.61 | 6 |
| ATOM | 425 | OG | SER | A | 168 | 7.128 | 30.624 | 31.944 | 1.00 | 41.71 | 8 |
| ATOM | 426 | C | SER | A | 168 | 4.884 | 32.652 | 31.518 | 1.00 | 30.79 | 6 |
| ATOM | 427 | O | SER | A | 168 | 5.266 | 33.502 | 32.301 | 1.00 | 33.91 | 8 |
| ATOM | 428 | N | VAL | A | 169 | 4.426 | 32.962 | 30.314 | 1.00 | 35.38 | 7 |
| ATOM | 429 | CA | VAL | A | 169 | 4.455 | 34.357 | 29.876 | 1.00 | 27.71 | 6 |
| ATOM | 430 | CB | VAL | A | 169 | 4.121 | 34.448 | 28.385 | 1.00 | 29.96 | 6 |
| ATOM | 431 | CG1 | VAL | A | 169 | 4.086 | 35.924 | 27.943 | 1.00 | 25.54 | 6 |
| ATOM | 432 | CG2 | VAL | A | 169 | 5.195 | 33.724 | 27.582 | 1.00 | 33.79 | 6 |
| ATOM | 433 | C | VAL | A | 169 | 3.604 | 35.213 | 30.817 | 1.00 | 32.85 | 6 |
| ATOM | 434 | O | VAL | A | 169 | 3.951 | 36.282 | 31.333 | 1.00 | 35.86 | 8 |
| ATOM | 435 | N | LEU | A | 170 | 2.431 | 34.704 | 31.152 | 1.00 | 35.39 | 7 |
| ATOM | 436 | CA | LEU | A | 170 | 1.500 | 35.385 | 32.050 | 1.00 | 39.23 | 6 |
| ATOM | 437 | CB | LEU | A | 170 | 0.244 | 34.542 | 32.100 | 1.00 | 35.15 | 6 |
| ATOM | 438 | CG | LEU | A | 170 | −0.801 | 34.822 | 31.014 | 1.00 | 38.80 | 6 |
| ATOM | 439 | CD1 | LEU | A | 170 | −2.126 | 34.272 | 31.565 | 1.00 | 42.41 | 6 |
| ATOM | 440 | CD2 | LEU | A | 170 | −0.976 | 36.292 | 30.731 | 1.00 | 45.02 | 6 |
| ATOM | 441 | C | LEU | A | 170 | 2.081 | 35.543 | 33.439 | 1.00 | 37.13 | 6 |
| ATOM | 442 | O | LEU | A | 170 | 2.037 | 36.613 | 34.032 | 1.00 | 38.03 | 8 |
| ATOM | 443 | N | LYS | A | 171 | 2.655 | 34.441 | 33.932 | 1.00 | 39.80 | 7 |
| ATOM | 444 | CA | LYS | A | 171 | 3.240 | 34.460 | 35.275 | 1.00 | 44.19 | 6 |
| ATOM | 445 | CB | LYS | A | 171 | 3.846 | 33.078 | 35.586 | 1.00 | 61.33 | 6 |
| ATOM | 446 | CG | LYS | A | 171 | 4.568 | 33.045 | 36.927 | 1.00 | 70.55 | 6 |
| ATOM | 447 | CD | LYS | A | 171 | 3.614 | 33.375 | 38.065 | 1.00 | 82.76 | 6 |
| ATOM | 448 | CE | LYS | A | 171 | 4.325 | 33.536 | 39.396 | 1.00 | 86.15 | 6 |
| ATOM | 449 | NZ | LYS | A | 171 | 3.605 | 34.470 | 40.306 | 1.00 | 86.50 | 7 |
| ATOM | 450 | C | LYS | A | 171 | 4.330 | 35.495 | 35.417 | 1.00 | 42.25 | 6 |
| ATOM | 451 | O | LYS | A | 171 | 4.501 | 36.069 | 36.505 | 1.00 | 40.60 | 8 |
| ATOM | 452 | N | ASN | A | 172 | 5.098 | 35.697 | 34.326 | 1.00 | 34.05 | 7 |
| ATOM | 453 | CA | ASN | A | 172 | 6.151 | 36.713 | 34.380 | 1.00 | 32.66 | 6 |
| ATOM | 454 | CB | ASN | A | 172 | 7.200 | 36.380 | 33.287 | 1.00 | 39.13 | 6 |
| ATOM | 455 | CG | ASN | A | 172 | 8.163 | 35.288 | 33.667 | 1.00 | 44.80 | 6 |
| ATOM | 456 | OD1 | ASN | A | 172 | 9.197 | 35.585 | 34.263 | 1.00 | 49.14 | 8 |
| ATOM | 457 | ND2 | ASN | A | 172 | 7.897 | 34.039 | 33.329 | 1.00 | 37.24 | 7 |
| ATOM | 458 | C | ASN | A | 172 | 5.661 | 38.135 | 34.153 | 1.00 | 32.11 | 6 |
| ATOM | 459 | O | ASN | A | 172 | 6.468 | 39.055 | 33.977 | 1.00 | 34.88 | 8 |
| ATOM | 460 | N | ASN | A | 173 | 4.358 | 38.394 | 34.203 | 1.00 | 31.68 | 7 |
| ATOM | 461 | CA | ASN | A | 173 | 3.768 | 39.716 | 34.061 | 1.00 | 29.24 | 6 |
| ATOM | 462 | CB | ASN | A | 173 | 4.009 | 40.629 | 35.235 | 1.00 | 35.84 | 6 |
| ATOM | 463 | CG | ASN | A | 173 | 3.450 | 39.955 | 36.506 | 1.00 | 36.42 | 6 |
| ATOM | 464 | OD1 | ASN | A | 173 | 2.591 | 39.085 | 36.396 | 1.00 | 39.55 | 8 |
| ATOM | 465 | ND2 | ASN | A | 173 | 4.002 | 40.381 | 37.626 | 1.00 | 53.62 | 7 |
| ATOM | 466 | C | ASN | A | 173 | 4.197 | 40.404 | 32.740 | 1.00 | 29.47 | 6 |
| ATOM | 467 | O | ASN | A | 173 | 4.307 | 41.640 | 32.703 | 1.00 | 32.55 | 8 |
| ATOM | 468 | N | LEU | A | 174 | 4.282 | 39.567 | 31.697 | 1.00 | 31.56 | 7 |
| ATOM | 469 | CA | LEU | A | 174 | 4.668 | 40.131 | 30.389 | 1.00 | 27.42 | 6 |
| ATOM | 470 | CB | LEU | A | 174 | 5.487 | 39.094 | 29.567 | 1.00 | 27.30 | 6 |
| ATOM | 471 | CG | LEU | A | 174 | 6.789 | 38.694 | 30.298 | 1.00 | 29.12 | 6 |
| ATOM | 472 | CD1 | LEU | A | 174 | 7.411 | 37.496 | 29.567 | 1.00 | 28.87 | 6 |
| ATOM | 473 | CD2 | LEU | A | 174 | 7.755 | 39.890 | 30.307 | 1.00 | 30.51 | 6 |
| ATOM | 474 | C | LEU | A | 174 | 3.472 | 40.556 | 29.553 | 1.00 | 30.31 | 6 |
| ATOM | 475 | O | LEU | A | 174 | 3.738 | 41.133 | 28.468 | 1.00 | 26.30 | 8 |
| ATOM | 476 | N | CYS | A | 175 | 2.255 | 40.276 | 30.006 | 1.00 | 30.27 | 7 |
| ATOM | 477 | CA | CYS | A | 175 | 1.110 | 40.728 | 29.213 | 1.00 | 30.49 | 6 |
| ATOM | 478 | C | CYS | A | 175 | 0.364 | 41.868 | 29.883 | 1.00 | 30.71 | 6 |
| ATOM | 479 | O | CYS | A | 175 | 0.383 | 41.960 | 31.119 | 1.00 | 28.85 | 8 |
| ATOM | 480 | CB | CYS | A | 175 | 0.225 | 39.531 | 28.885 | 1.00 | 33.22 | 6 |
| ATOM | 481 | SG | CYS | A | 175 | 1.157 | 38.382 | 27.797 | 1.00 | 34.32 | 16 |
| ATOM | 482 | N | PRO | A | 176 | −0.216 | 42.747 | 29.126 | 1.00 | 27.02 | 7 |
| ATOM | 483 | CD | PRO | A | 176 | −0.202 | 42.778 | 27.620 | 1.00 | 27.31 | 6 |
| ATOM | 484 | CA | PRO | A | 176 | −1.031 | 43.860 | 29.607 | 1.00 | 29.02 | 6 |
| ATOM | 485 | CB | PRO | A | 176 | −1.802 | 44.330 | 28.356 | 1.00 | 30.75 | 6 |
| ATOM | 486 | CG | PRO | A | 176 | −0.681 | 44.201 | 27.369 | 1.00 | 29.79 | 6 |
| ATOM | 487 | C | PRO | A | 176 | −2.061 | 43.417 | 30.656 | 1.00 | 28.74 | 6 |
| ATOM | 488 | O | PRO | A | 176 | −2.600 | 42.326 | 30.586 | 1.00 | 29.00 | 8 |
| ATOM | 489 | N | SER | A | 177 | −2.232 | 44.390 | 31.582 | 1.00 | 30.95 | 7 |
| ATOM | 490 | CA | SER | A | 177 | −3.173 | 44.142 | 32.688 | 1.00 | 35.36 | 6 |
| ATOM | 491 | CB | SER | A | 177 | −3.415 | 45.461 | 33.435 | 1.00 | 36.82 | 6 |
| ATOM | 492 | OG | SER | A | 177 | −2.202 | 46.102 | 33.764 | 1.00 | 45.84 | 8 |
| ATOM | 493 | C | SER | A | 177 | −4.485 | 43.656 | 32.120 | 1.00 | 38.68 | 6 |
| ATOM | 494 | O | SER | A | 177 | −4.918 | 44.231 | 31.107 | 1.00 | 42.81 | 8 |
| ATOM | 495 | N | GLY | A | 178 | −5.101 | 42.644 | 32.713 | 1.00 | 42.54 | 7 |
| ATOM | 496 | CA | GLY | A | 178 | −6.357 | 42.145 | 32.183 | 1.00 | 44.10 | 6 |

-continued

| | | | | | | | | | | |
|---|---|---|---|---|---|---|---|---|---|---|
| | | | PDB FILE LISTING - cd811e1.pdb | | | | | | | |
| ATOM | 497 | C | GLY | A | 178 | −6.180 | 40.771 | 31.571 | 1.00 | 47.58 | 6 |
| ATOM | 498 | O | GLY | A | 178 | −7.075 | 39.934 | 31.641 | 1.00 | 48.95 | 8 |
| ATOM | 499 | N | SER | A | 179 | −5.012 | 40.548 | 30.951 | 1.00 | 42.04 | 7 |
| ATOM | 500 | CA | SER | A | 179 | −4.715 | 39.262 | 30.363 | 1.00 | 39.16 | 6 |
| ATOM | 501 | CB | SER | A | 179 | −3.278 | 39.360 | 29.771 | 1.00 | 35.52 | 6 |
| ATOM | 502 | OG | SER | A | 179 | −3.444 | 40.056 | 28.515 | 1.00 | 44.97 | 8 |
| ATOM | 503 | C | SER | A | 179 | −4.702 | 38.152 | 31.410 | 1.00 | 41.15 | 6 |
| ATOM | 504 | O | SER | A | 179 | −4.185 | 38.285 | 32.522 | 1.00 | 38.03 | 8 |
| ATOM | 505 | N | ASN | A | 180 | −5.273 | 37.027 | 31.030 | 1.00 | 37.43 | 7 |
| ATOM | 506 | CA | ASN | A | 180 | −5.370 | 35.833 | 31.843 | 1.00 | 38.91 | 6 |
| ATOM | 507 | CB | ASN | A | 180 | −6.498 | 35.968 | 32.868 | 1.00 | 43.64 | 6 |
| ATOM | 508 | CG | ASN | A | 180 | −7.760 | 36.496 | 32.206 | 1.00 | 50.72 | 6 |
| ATOM | 509 | OD1 | ASN | A | 180 | −7.969 | 37.713 | 32.184 | 1.00 | 47.95 | 8 |
| ATOM | 510 | ND2 | ASN | A | 180 | −8.569 | 35.607 | 31.652 | 1.00 | 40.10 | 7 |
| ATOM | 511 | C | ASN | A | 180 | −5.659 | 34.707 | 30.844 | 1.00 | 39.79 | 6 |
| ATOM | 512 | O | ASN | A | 180 | −5.906 | 35.014 | 29.664 | 1.00 | 41.96 | 8 |
| ATOM | 513 | N | ILE | A | 181 | −5.508 | 33.473 | 31.256 | 1.00 | 40.01 | 7 |
| ATOM | 514 | CA | ILE | A | 181 | −5.631 | 32.321 | 30.375 | 1.00 | 35.08 | 6 |
| ATOM | 515 | CB | ILE | A | 181 | −5.369 | 31.007 | 31.114 | 1.00 | 43.35 | 6 |
| ATOM | 516 | CG2 | ILE | A | 181 | −6.180 | 30.867 | 32.394 | 1.00 | 50.56 | 6 |
| ATOM | 517 | CG1 | ILE | A | 181 | −5.664 | 29.800 | 30.226 | 1.00 | 37.17 | 6 |
| ATOM | 518 | CD1 | ILE | A | 181 | −5.177 | 28.476 | 30.772 | 1.00 | 61.09 | 6 |
| ATOM | 519 | C | ILE | A | 181 | −6.930 | 32.343 | 29.593 | 1.00 | 38.56 | 6 |
| ATOM | 520 | O | ILE | A | 181 | −6.896 | 32.286 | 28.357 | 1.00 | 39.50 | 8 |
| ATOM | 521 | N | ILE | A | 182 | −8.065 | 32.520 | 30.276 | 1.00 | 31.14 | 7 |
| ATOM | 522 | CA | ILE | A | 182 | −9.323 | 32.541 | 29.548 | 1.00 | 33.99 | 6 |
| ATOM | 523 | CB | ILE | A | 182 | −10.590 | 32.395 | 30.398 | 1.00 | 35.20 | 6 |
| ATOM | 524 | CG2 | ILE | A | 182 | −11.798 | 32.450 | 29.440 | 1.00 | 38.49 | 6 |
| ATOM | 525 | CG1 | ILE | A | 182 | −10.615 | 30.996 | 31.030 | 1.00 | 33.92 | 6 |
| ATOM | 526 | CD1 | ILE | A | 182 | −11.972 | 30.794 | 31.679 | 1.00 | 41.51 | 6 |
| ATOM | 527 | C | ILE | A | 182 | −9.453 | 33.664 | 28.548 | 1.00 | 33.21 | 6 |
| ATOM | 528 | O | ILE | A | 182 | −9.686 | 33.395 | 27.358 | 1.00 | 32.00 | 8 |
| ATOM | 529 | N | SER | A | 183 | −9.300 | 34.909 | 28.992 | 1.00 | 32.06 | 7 |
| ATOM | 530 | CA | SER | A | 183 | −9.481 | 36.019 | 28.046 | 1.00 | 30.17 | 6 |
| ATOM | 531 | CB | SER | A | 183 | −9.173 | 37.363 | 28.705 | 1.00 | 40.84 | 6 |
| ATOM | 532 | OG | SER | A | 183 | −7.832 | 37.387 | 29.180 | 1.00 | 50.43 | 8 |
| ATOM | 533 | C | SER | A | 183 | −8.539 | 35.849 | 26.867 | 1.00 | 29.79 | 6 |
| ATOM | 534 | O | SER | A | 183 | −8.841 | 36.209 | 25.719 | 1.00 | 30.43 | 8 |
| ATOM | 535 | N | ASN | A | 184 | −7.325 | 35.342 | 27.158 | 1.00 | 29.85 | 7 |
| ATOM | 536 | CA | ASN | A | 184 | −6.366 | 35.206 | 26.073 | 1.00 | 29.42 | 6 |
| ATOM | 537 | CB | ASN | A | 184 | −4.954 | 35.100 | 26.613 | 1.00 | 32.69 | 6 |
| ATOM | 538 | CG | ASN | A | 184 | −3.909 | 35.579 | 25.617 | 1.00 | 39.32 | 6 |
| ATOM | 539 | OD1 | ASN | A | 184 | −3.902 | 36.737 | 25.180 | 1.00 | 38.73 | 8 |
| ATOM | 540 | ND2 | ASN | A | 184 | −3.026 | 34.659 | 25.253 | 1.00 | 37.01 | 7 |
| ATOM | 541 | C | ASN | A | 184 | −6.767 | 34.168 | 25.046 | 1.00 | 29.90 | 6 |
| ATOM | 542 | O | ASN | A | 184 | −6.416 | 34.312 | 23.886 | 1.00 | 30.55 | 8 |
| ATOM | 543 | N | LEU | A | 185 | −7.594 | 33.180 | 25.400 | 1.00 | 28.17 | 7 |
| ATOM | 544 | CA | LEU | A | 185 | −8.022 | 32.190 | 24.418 | 1.00 | 28.14 | 6 |
| ATOM | 545 | CB | LEU | A | 185 | −8.792 | 31.069 | 25.170 | 1.00 | 31.80 | 6 |
| ATOM | 546 | CG | LEU | A | 185 | −7.873 | 30.228 | 26.077 | 1.00 | 37.24 | 6 |
| ATOM | 547 | CD1 | LEU | A | 185 | −8.734 | 29.247 | 26.874 | 1.00 | 38.22 | 6 |
| ATOM | 548 | CD2 | LEU | A | 185 | −6.862 | 29.482 | 25.200 | 1.00 | 30.41 | 6 |
| ATOM | 549 | C | LEU | A | 185 | −8.978 | 32.794 | 23.390 | 1.00 | 25.61 | 6 |
| ATOM | 550 | O | LEU | A | 185 | −9.127 | 32.198 | 22.304 | 1.00 | 29.28 | 8 |
| ATOM | 551 | N | PHE | A | 186 | −9.577 | 33.930 | 23.688 | 1.00 | 25.10 | 7 |
| ATOM | 552 | CA | PHE | A | 186 | −10.524 | 34.523 | 22.720 | 1.00 | 28.91 | 6 |
| ATOM | 553 | CB | PHE | A | 186 | −11.725 | 35.124 | 23.488 | 1.00 | 28.71 | 6 |
| ATOM | 554 | CG | PHE | A | 186 | −12.636 | 34.083 | 24.083 | 1.00 | 31.64 | 6 |
| ATOM | 555 | CD1 | PHE | A | 186 | −12.428 | 33.583 | 25.332 | 1.00 | 30.09 | 6 |
| ATOM | 556 | CD2 | PHE | A | 186 | −13.724 | 33.670 | 23.346 | 1.00 | 29.23 | 6 |
| ATOM | 557 | CE1 | PHE | A | 186 | −13.280 | 32.604 | 25.875 | 1.00 | 34.13 | 6 |
| ATOM | 558 | CE2 | PHE | A | 186 | −14.599 | 32.724 | 23.893 | 1.00 | 27.11 | 6 |
| ATOM | 559 | CZ | PHE | A | 186 | −14.364 | 32.192 | 25.124 | 1.00 | 31.22 | 6 |
| ATOM | 560 | C | PHE | A | 186 | −9.888 | 35.661 | 21.919 | 1.00 | 28.36 | 6 |
| ATOM | 561 | O | PHE | A | 186 | −10.575 | 36.472 | 21.302 | 1.00 | 30.96 | 8 |
| ATOM | 562 | N | LYS | A | 187 | −8.558 | 35.744 | 21.959 | 1.00 | 29.55 | 7 |
| ATOM | 563 | CA | LYS | A | 187 | −7.849 | 36.800 | 21.204 | 1.00 | 30.12 | 6 |
| ATOM | 564 | CB | LYS | A | 187 | −6.981 | 37.575 | 22.229 | 1.00 | 30.88 | 6 |
| ATOM | 565 | CG | LYS | A | 187 | −7.821 | 38.654 | 22.890 | 1.00 | 43.39 | 6 |
| ATOM | 566 | CD | LYS | A | 187 | −7.047 | 39.391 | 23.958 | 1.00 | 48.15 | 6 |
| ATOM | 567 | CE | LYS | A | 187 | −6.085 | 40.405 | 23.339 | 1.00 | 41.67 | 6 |
| ATOM | 568 | NZ | LYS | A | 187 | −5.759 | 41.430 | 24.369 | 1.00 | 42.64 | 7 |
| ATOM | 569 | C | LYS | A | 187 | −6.869 | 36.185 | 20.213 | 1.00 | 27.72 | 6 |
| ATOM | 570 | O | LYS | A | 187 | −6.370 | 35.086 | 20.445 | 1.00 | 28.84 | 8 |
| ATOM | 571 | N | GLU | A | 188 | −6.606 | 36.916 | 19.110 | 1.00 | 26.40 | 7 |
| ATOM | 572 | CA | GLU | A | 188 | −5.608 | 36.498 | 18.144 | 1.00 | 24.95 | 6 |
| ATOM | 573 | CB | GLU | A | 188 | −5.558 | 37.520 | 16.994 | 1.00 | 30.53 | 6 |

-continued

| | | PDB FILE LISTING - cd811e1.pdb | | | | | | | |
|---|---|---|---|---|---|---|---|---|---|
| ATOM | 574 | CG | GLU | A | 188 | −6.924 | 37.605 | 16.315 | 1.00 | 39.56 | 6 |
| ATOM | 575 | CD | GLU | A | 188 | −6.932 | 38.457 | 15.068 | 1.00 | 58.60 | 6 |
| ATOM | 576 | OE1 | GLU | A | 188 | −6.597 | 39.661 | 15.133 | 1.00 | 57.62 | 8 |
| ATOM | 577 | OE2 | GLU | A | 188 | −7.290 | 37.897 | 14.009 | 1.00 | 64.79 | 8 |
| ATOM | 578 | C | GLU | A | 188 | −4.194 | 36.601 | 18.808 | 1.00 | 20.96 | 6 |
| ATOM | 579 | O | GLU | A | 188 | −4.014 | 37.439 | 19.683 | 1.00 | 25.27 | 8 |
| ATOM | 580 | N | ASP | A | 189 | −3.380 | 35.673 | 18.394 | 1.00 | 25.32 | 7 |
| ATOM | 581 | CA | ASP | A | 189 | −2.027 | 35.623 | 18.967 | 1.00 | 22.63 | 6 |
| ATOM | 582 | CB | ASP | A | 189 | −1.380 | 34.237 | 18.781 | 1.00 | 28.31 | 6 |
| ATOM | 583 | CG | ASP | A | 189 | −0.770 | 34.114 | 17.422 | 1.00 | 24.61 | 6 |
| ATOM | 584 | OD1 | ASP | A | 189 | 0.473 | 33.884 | 17.302 | 1.00 | 27.48 | 8 |
| ATOM | 585 | OD2 | ASP | A | 189 | −1.347 | 34.337 | 16.351 | 1.00 | 35.01 | 8 |
| ATOM | 586 | C | ASP | A | 189 | −1.167 | 36.691 | 18.300 | 1.00 | 22.86 | 6 |
| ATOM | 587 | O | ASP | A | 189 | −1.537 | 37.330 | 17.273 | 1.00 | 24.00 | 8 |
| ATOM | 588 | N | CYS | A | 190 | 0.065 | 36.811 | 18.805 | 1.00 | 22.75 | 7 |
| ATOM | 589 | CA | CYS | A | 190 | 0.956 | 37.851 | 18.216 | 1.00 | 21.64 | 6 |
| ATOM | 590 | C | CYS | A | 190 | 1.352 | 37.562 | 16.782 | 1.00 | 21.74 | 6 |
| ATOM | 591 | O | CYS | A | 190 | 1.569 | 38.596 | 16.081 | 1.00 | 24.29 | 8 |
| ATOM | 592 | CB | CYS | A | 190 | 2.133 | 38.128 | 19.101 | 1.00 | 23.60 | 6 |
| ATOM | 593 | SG | CYS | A | 190 | 1.730 | 38.711 | 20.756 | 1.00 | 26.96 | 16 |
| ATOM | 594 | N | HIS | A | 191 | 1.496 | 36.339 | 16.299 | 1.00 | 22.50 | 7 |
| ATOM | 595 | CA | HIS | A | 191 | 1.881 | 36.196 | 14.901 | 1.00 | 21.71 | 6 |
| ATOM | 596 | CB | HIS | A | 191 | 2.232 | 34.740 | 14.596 | 1.00 | 26.64 | 6 |
| ATOM | 597 | CG | HIS | A | 191 | 3.551 | 34.362 | 15.222 | 1.00 | 26.82 | 6 |
| ATOM | 598 | CD2 | HIS | A | 191 | 4.355 | 34.965 | 16.093 | 1.00 | 26.94 | 6 |
| ATOM | 599 | ND1 | HIS | A | 191 | 4.129 | 33.171 | 14.866 | 1.00 | 29.12 | 7 |
| ATOM | 600 | CE1 | HIS | A | 191 | 5.285 | 33.094 | 15.532 | 1.00 | 25.60 | 6 |
| ATOM | 601 | NE2 | HIS | A | 191 | 5.427 | 34.114 | 16.334 | 1.00 | 25.91 | 7 |
| ATOM | 602 | C | HIS | A | 191 | 0.831 | 36.773 | 14.002 | 1.00 | 21.74 | 6 |
| ATOM | 603 | O | HIS | A | 191 | 1.141 | 37.315 | 12.904 | 1.00 | 24.92 | 8 |
| ATOM | 604 | N | GLN | A | 192 | −0.436 | 36.475 | 14.363 | 1.00 | 26.00 | 7 |
| ATOM | 605 | CA | GLN | A | 192 | −1.530 | 36.988 | 13.529 | 1.00 | 26.00 | 6 |
| ATOM | 606 | CB | GLN | A | 192 | −2.890 | 36.549 | 14.130 | 1.00 | 25.26 | 6 |
| ATOM | 607 | CG | GLN | A | 192 | −3.979 | 37.056 | 13.177 | 1.00 | 36.23 | 6 |
| ATOM | 608 | CD | GLN | A | 192 | −3.954 | 36.524 | 11.775 | 1.00 | 42.56 | 6 |
| ATOM | 609 | OE1 | GLN | A | 192 | −4.126 | 35.350 | 11.486 | 1.00 | 46.38 | 8 |
| ATOM | 610 | NE2 | GLN | A | 192 | −3.772 | 37.366 | 10.753 | 1.00 | 34.35 | 7 |
| ATOM | 611 | C | GLN | A | 192 | −1.505 | 38.503 | 13.534 | 1.00 | 25.56 | 6 |
| ATOM | 612 | O | GLN | A | 192 | −1.717 | 39.139 | 12.485 | 1.00 | 25.01 | 8 |
| ATOM | 613 | N | LYS | A | 193 | −1.318 | 39.155 | 14.685 | 1.00 | 22.99 | 7 |
| ATOM | 614 | CA | LYS | A | 193 | −1.206 | 40.597 | 14.767 | 1.00 | 21.22 | 6 |
| ATOM | 615 | CB | LYS | A | 193 | −1.188 | 41.124 | 16.218 | 1.00 | 20.84 | 6 |
| ATOM | 616 | CG | LYS | A | 193 | −2.495 | 40.778 | 16.896 | 1.00 | 22.00 | 6 |
| ATOM | 617 | CD | LYS | A | 193 | −3.688 | 41.482 | 16.250 | 1.00 | 28.69 | 6 |
| ATOM | 618 | CE | LYS | A | 193 | −4.963 | 41.573 | 17.081 | 1.00 | 42.13 | 6 |
| ATOM | 619 | NZ | LYS | A | 193 | −4.903 | 42.588 | 18.149 | 1.00 | 42.68 | 7 |
| ATOM | 620 | C | LYS | A | 193 | −0.033 | 41.140 | 13.970 | 1.00 | 23.50 | 6 |
| ATOM | 621 | O | LYS | A | 193 | −0.182 | 42.216 | 13.366 | 1.00 | 24.64 | 8 |
| ATOM | 622 | N | ILE | A | 194 | 1.095 | 40.444 | 13.924 | 1.00 | 20.30 | 7 |
| ATOM | 623 | CA | ILE | A | 194 | 2.211 | 40.878 | 13.074 | 1.00 | 22.70 | 6 |
| ATOM | 624 | CB | ILE | A | 194 | 3.436 | 39.972 | 13.318 | 1.00 | 22.09 | 6 |
| ATOM | 625 | CG2 | ILE | A | 194 | 4.487 | 40.101 | 12.184 | 1.00 | 23.81 | 6 |
| ATOM | 626 | CG1 | ILE | A | 194 | 3.920 | 40.404 | 14.714 | 1.00 | 20.79 | 6 |
| ATOM | 627 | CD1 | ILE | A | 194 | 4.915 | 39.428 | 15.349 | 1.00 | 24.12 | 6 |
| ATOM | 628 | C | ILE | A | 194 | 1.767 | 40.836 | 11.632 | 1.00 | 22.66 | 6 |
| ATOM | 629 | O | ILE | A | 194 | 1.942 | 41.791 | 10.879 | 1.00 | 23.54 | 8 |
| ATOM | 630 | N | ASP | A | 195 | 1.079 | 39.728 | 11.287 | 1.00 | 25.86 | 7 |
| ATOM | 631 | CA | ASP | A | 195 | 0.636 | 39.644 | 9.875 | 1.00 | 28.42 | 6 |
| ATOM | 632 | CB | ASP | A | 195 | −0.154 | 38.334 | 9.694 | 1.00 | 30.81 | 6 |
| ATOM | 633 | CG | ASP | A | 195 | 0.736 | 37.219 | 9.172 | 1.00 | 43.61 | 6 |
| ATOM | 634 | OD1 | ASP | A | 195 | 0.354 | 36.035 | 9.317 | 1.00 | 40.90 | 8 |
| ATOM | 635 | OD2 | ASP | A | 195 | 1.786 | 37.567 | 8.637 | 1.00 | 40.27 | 8 |
| ATOM | 636 | C | ASP | A | 195 | −0.330 | 40.800 | 9.581 | 1.00 | 25.57 | 6 |
| ATOM | 637 | O | ASP | A | 195 | −0.257 | 41.436 | 8.510 | 1.00 | 28.18 | 8 |
| ATOM | 638 | N | ASP | A | 196 | −1.223 | 41.116 | 10.487 | 1.00 | 25.86 | 7 |
| ATOM | 639 | CA | ASP | A | 196 | −2.214 | 42.186 | 10.297 | 1.00 | 27.70 | 6 |
| ATOM | 640 | CB | ASP | A | 196 | −3.190 | 42.304 | 11.477 | 1.00 | 27.67 | 6 |
| ATOM | 641 | CG | ASP | A | 196 | −4.130 | 41.117 | 11.536 | 1.00 | 35.55 | 6 |
| ATOM | 642 | OD1 | ASP | A | 196 | −4.182 | 40.386 | 10.527 | 1.00 | 37.44 | 8 |
| ATOM | 643 | OD2 | ASP | A | 196 | −4.830 | 40.899 | 12.549 | 1.00 | 40.00 | 8 |
| ATOM | 644 | C | ASP | A | 196 | −1.520 | 43.522 | 10.070 | 1.00 | 30.21 | 6 |
| ATOM | 645 | O | ASP | A | 196 | −1.970 | 44.383 | 9.300 | 1.00 | 29.23 | 8 |
| ATOM | 646 | N | LEU | A | 197 | −0.448 | 43.765 | 10.821 | 1.00 | 26.41 | 7 |
| ATOM | 647 | CA | LEU | A | 197 | 0.329 | 44.989 | 10.638 | 1.00 | 24.54 | 6 |
| ATOM | 648 | CB | LEU | A | 197 | 1.464 | 45.064 | 11.623 | 1.00 | 22.89 | 6 |
| ATOM | 649 | CG | LEU | A | 197 | 2.400 | 46.254 | 11.546 | 1.00 | 24.59 | 6 |
| ATOM | 650 | CD1 | LEU | A | 197 | 1.789 | 47.610 | 11.857 | 1.00 | 28.10 | 6 |

-continued

| PDB FILE LISTING - cd811e1.pdb | | | | | | | | | |
|---|---|---|---|---|---|---|---|---|---|
| ATOM | 651 | CD2 | LEU | A | 197 | 3.592 | 45.960 | 12.455 | 1.00 | 27.91 | 6 |
| ATOM | 652 | C | LEU | A | 197 | 0.858 | 45.132 | 9.195 | 1.00 | 22.96 | 6 |
| ATOM | 653 | O | LEU | A | 197 | 0.744 | 46.208 | 8.599 | 1.00 | 25.34 | 8 |
| ATOM | 654 | N | PHE | A | 198 | 1.456 | 44.113 | 8.670 | 1.00 | 22.19 | 7 |
| ATOM | 655 | CA | PHE | A | 198 | 2.074 | 44.173 | 7.320 | 1.00 | 26.14 | 6 |
| ATOM | 656 | CB | PHE | A | 198 | 3.191 | 43.158 | 7.237 | 1.00 | 25.23 | 6 |
| ATOM | 657 | CG | PHE | A | 198 | 4.401 | 43.555 | 8.043 | 1.00 | 24.37 | 6 |
| ATOM | 658 | CD1 | PHE | A | 198 | 4.583 | 43.021 | 9.311 | 1.00 | 27.98 | 6 |
| ATOM | 659 | CD2 | PHE | A | 198 | 5.290 | 44.493 | 7.600 | 1.00 | 26.06 | 6 |
| ATOM | 660 | CE1 | PHE | A | 198 | 5.669 | 43.416 | 10.068 | 1.00 | 26.50 | 6 |
| ATOM | 661 | CE2 | PHE | A | 198 | 6.376 | 44.898 | 8.324 | 1.00 | 26.50 | 6 |
| ATOM | 662 | CZ | PHE | A | 198 | 6.583 | 44.349 | 9.584 | 1.00 | 24.03 | 6 |
| ATOM | 663 | C | PHE | A | 198 | 1.063 | 44.075 | 6.215 | 1.00 | 27.88 | 6 |
| ATOM | 664 | O | PHE | A | 198 | 1.389 | 44.527 | 5.119 | 1.00 | 29.23 | 8 |
| ATOM | 665 | N | SER | A | 199 | −0.163 | 43.662 | 6.554 | 1.00 | 30.11 | 7 |
| ATOM | 666 | CA | SER | A | 199 | −1.196 | 43.609 | 5.519 | 1.00 | 32.39 | 6 |
| ATOM | 667 | CB | SER | A | 199 | −1.975 | 42.287 | 5.669 | 1.00 | 34.42 | 6 |
| ATOM | 668 | OG | SER | A | 199 | −2.802 | 42.466 | 6.800 | 1.00 | 43.38 | 8 |
| ATOM | 669 | C | SER | A | 199 | −2.129 | 44.790 | 5.572 | 1.00 | 32.01 | 6 |
| ATOM | 670 | O | SER | A | 199 | −3.108 | 44.873 | 4.809 | 1.00 | 36.63 | 8 |
| ATOM | 671 | N | GLY | A | 200 | −1.936 | 45.715 | 6.497 | 1.00 | 26.46 | 7 |
| ATOM | 672 | CA | GLY | A | 200 | −2.719 | 46.913 | 6.622 | 1.00 | 30.24 | 6 |
| ATOM | 673 | C | GLY | A | 200 | −4.089 | 46.697 | 7.221 | 1.00 | 37.40 | 6 |
| ATOM | 674 | O | GLY | A | 200 | −5.045 | 47.396 | 6.885 | 1.00 | 42.48 | 8 |
| ATOM | 675 | N | LYS | A | 201 | −4.195 | 45.797 | 8.186 | 1.00 | 35.07 | 7 |
| ATOM | 676 | CA | LYS | A | 201 | −5.466 | 45.583 | 8.887 | 1.00 | 39.63 | 6 |
| ATOM | 677 | CB | LYS | A | 201 | −5.761 | 44.094 | 9.088 | 1.00 | 41.19 | 6 |
| ATOM | 678 | CG | LYS | A | 201 | −5.538 | 43.369 | 7.769 | 1.00 | 43.81 | 6 |
| ATOM | 679 | CD | LYS | A | 201 | −6.418 | 42.142 | 7.586 | 1.00 | 52.66 | 6 |
| ATOM | 680 | CE | LYS | A | 201 | −6.541 | 41.945 | 6.069 | 1.00 | 53.36 | 6 |
| ATOM | 681 | NZ | LYS | A | 201 | −6.396 | 43.284 | 5.415 | 1.00 | 53.44 | 6 |
| ATOM | 682 | C | LYS | A | 201 | −5.373 | 46.308 | 10.219 | 1.00 | 44.11 | 6 |
| ATOM | 683 | O | LYS | A | 201 | −5.967 | 47.376 | 10.421 | 1.00 | 48.21 | 8 |
| ATOM | 684 | N | HIS | A | 202 | −4.645 | 45.700 | 11.127 | 1.00 | 41.73 | 7 |
| ATOM | 685 | CA | HIS | A | 202 | −4.429 | 46.288 | 12.448 | 1.00 | 47.06 | 6 |
| ATOM | 686 | C | HIS | A | 202 | −4.966 | 47.699 | 12.541 | 1.00 | 50.86 | 6 |
| ATOM | 687 | O | HIS | A | 202 | −6.043 | 47.930 | 13.140 | 1.00 | 51.62 | 8 |
| ATOM | 688 | CB | HIS | A | 202 | −2.892 | 46.295 | 12.678 | 1.00 | 39.32 | 6 |
| ATOM | 689 | CG | HIS | A | 202 | −2.571 | 45.523 | 13.918 | 1.00 | 54.43 | 6 |
| ATOM | 690 | ND1 | HIS | A | 202 | −3.177 | 45.808 | 15.124 | 1.00 | 60.36 | 7 |
| ATOM | 691 | CD2 | HIS | A | 202 | −1.740 | 44.481 | 14.121 | 1.00 | 32.15 | 6 |
| ATOM | 692 | CE1 | HIS | A | 202 | −2.714 | 44.975 | 16.050 | 1.00 | 58.04 | 6 |
| ATOM | 693 | NE2 | HIS | A | 202 | −1.847 | 44.161 | 15.461 | 1.00 | 66.87 | 7 |
| ATOM | 694 | CB | PHE | B | 213 | 19.717 | 35.136 | 16.091 | 0.00 | 34.83 | 6 |
| ATOM | 695 | CG | PHE | B | 213 | 20.197 | 34.465 | 17.321 | 0.00 | 44.80 | 6 |
| ATOM | 696 | CD1 | PHE | B | 213 | 21.533 | 34.182 | 17.521 | 0.00 | 58.13 | 6 |
| ATOM | 697 | CD2 | PHE | B | 213 | 19.319 | 34.146 | 18.350 | 0.00 | 62.44 | 6 |
| ATOM | 698 | CE1 | PHE | B | 213 | 21.983 | 33.580 | 18.677 | 0.00 | 56.87 | 6 |
| ATOM | 699 | CE2 | PHE | B | 213 | 19.751 | 33.535 | 19.518 | 0.00 | 69.83 | 6 |
| ATOM | 700 | CZ | PHE | B | 213 | 21.091 | 33.243 | 19.683 | 0.00 | 53.63 | 6 |
| ATOM | 701 | C | PHE | B | 213 | 18.658 | 35.823 | 13.931 | 1.00 | 38.28 | 6 |
| ATOM | 702 | O | PHE | B | 213 | 19.511 | 36.353 | 13.199 | 1.00 | 40.98 | 8 |
| ATOM | 703 | N | PHE | B | 213 | 20.058 | 33.920 | 13.960 | 0.00 | 39.06 | 7 |
| ATOM | 704 | CA | PHE | B | 213 | 18.949 | 34.523 | 14.688 | 1.00 | 37.25 | 6 |
| ATOM | 705 | N | VAL | B | 214 | 17.444 | 36.311 | 14.059 | 1.00 | 28.83 | 7 |
| ATOM | 706 | CA | VAL | B | 214 | 17.111 | 37.604 | 13.427 | 1.00 | 27.89 | 6 |
| ATOM | 707 | CB | VAL | B | 214 | 15.585 | 37.806 | 13.482 | 1.00 | 22.89 | 6 |
| ATOM | 708 | CG1 | VAL | B | 214 | 15.193 | 39.183 | 12.890 | 1.00 | 26.71 | 6 |
| ATOM | 709 | CG2 | VAL | B | 214 | 14.947 | 36.736 | 12.598 | 1.00 | 28.90 | 6 |
| ATOM | 710 | C | VAL | B | 214 | 17.745 | 38.665 | 14.270 | 1.00 | 28.77 | 6 |
| ATOM | 711 | O | VAL | B | 214 | 17.533 | 38.794 | 15.474 | 1.00 | 28.76 | 8 |
| ATOM | 712 | N | ASN | B | 215 | 18.444 | 39.614 | 13.620 | 1.00 | 29.41 | 7 |
| ATOM | 713 | CA | ASN | B | 215 | 19.127 | 40.646 | 14.396 | 1.00 | 28.39 | 6 |
| ATOM | 714 | CB | ASN | B | 215 | 20.442 | 40.928 | 13.643 | 1.00 | 32.91 | 6 |
| ATOM | 715 | CG | ASN | B | 215 | 21.148 | 42.093 | 14.265 | 1.00 | 39.44 | 6 |
| ATOM | 716 | OD1 | ASN | B | 215 | 21.865 | 41.881 | 15.245 | 1.00 | 53.33 | 8 |
| ATOM | 717 | ND2 | ASN | B | 215 | 20.905 | 43.288 | 13.757 | 1.00 | 37.32 | 7 |
| ATOM | 718 | C | ASN | B | 215 | 18.259 | 41.895 | 14.501 | 1.00 | 27.27 | 6 |
| ATOM | 719 | O | ASN | B | 215 | 17.705 | 42.313 | 13.486 | 1.00 | 27.80 | 8 |
| ATOM | 720 | N | LYS | B | 216 | 18.223 | 42.525 | 15.657 | 1.00 | 29.93 | 7 |
| ATOM | 721 | CA | LYS | B | 216 | 17.420 | 43.699 | 15.889 | 1.00 | 30.04 | 6 |
| ATOM | 722 | CB | LYS | B | 216 | 17.601 | 44.227 | 17.320 | 1.00 | 38.33 | 6 |
| ATOM | 723 | CG | LYS | B | 216 | 17.259 | 45.678 | 17.506 | 1.00 | 51.27 | 6 |
| ATOM | 724 | CD | LYS | B | 216 | 18.220 | 46.399 | 18.436 | 1.00 | 60.50 | 6 |
| ATOM | 725 | CE | LYS | B | 216 | 17.949 | 47.901 | 18.401 | 1.00 | 41.22 | 6 |
| ATOM | 726 | NZ | LYS | B | 216 | 18.269 | 48.521 | 19.723 | 1.00 | 56.24 | 7 |
| ATOM | 727 | C | LYS | B | 216 | 17.571 | 44.843 | 14.896 | 1.00 | 32.97 | 6 |

-continued

PDB FILE LISTING - cd811e1.pdb

| ATOM | 728 | O | LYS | B | 216 | 16.642 | 45.376 | 14.285 | 1.00 | 32.82 | 8 |
|---|---|---|---|---|---|---|---|---|---|---|---|
| ATOM | 729 | N | ASP | B | 217 | 18.815 | 45.234 | 14.662 | 1.00 | 30.39 | 7 |
| ATOM | 730 | CA | ASP | B | 217 | 19.079 | 46.384 | 13.755 | 1.00 | 28.18 | 6 |
| ATOM | 731 | CB | ASP | B | 217 | 20.615 | 46.597 | 13.856 | 1.00 | 37.07 | 6 |
| ATOM | 732 | CG | ASP | B | 217 | 20.974 | 47.025 | 15.271 | 1.00 | 50.77 | 6 |
| ATOM | 733 | OD1 | ASP | B | 217 | 20.325 | 47.961 | 15.789 | 1.00 | 50.99 | 8 |
| ATOM | 734 | OD2 | ASP | B | 217 | 21.873 | 46.381 | 15.855 | 1.00 | 48.20 | 8 |
| ATOM | 735 | C | ASP | B | 217 | 18.710 | 46.045 | 12.326 | 1.00 | 27.65 | 6 |
| ATOM | 736 | O | ASP | B | 217 | 18.209 | 46.917 | 11.586 | 1.00 | 29.68 | 8 |
| ATOM | 737 | N | GLN | B | 218 | 18.945 | 44.818 | 11.903 | 1.00 | 26.96 | 7 |
| ATOM | 738 | CA | GLN | B | 218 | 18.641 | 44.363 | 10.567 | 1.00 | 26.89 | 6 |
| ATOM | 739 | CB | GLN | B | 218 | 19.194 | 43.015 | 10.137 | 1.00 | 28.58 | 6 |
| ATOM | 740 | CG | GLN | B | 218 | 18.876 | 42.625 | 8.703 | 1.00 | 28.47 | 6 |
| ATOM | 741 | CD | GLN | B | 218 | 19.550 | 43.604 | 7.748 | 1.00 | 39.80 | 6 |
| ATOM | 742 | OE1 | GLN | B | 218 | 20.732 | 43.897 | 7.957 | 1.00 | 49.83 | 8 |
| ATOM | 743 | NE2 | GLN | B | 218 | 18.880 | 44.111 | 6.730 | 1.00 | 37.47 | 7 |
| ATOM | 744 | C | GLN | B | 218 | 17.118 | 44.408 | 10.342 | 1.00 | 26.99 | 6 |
| ATOM | 745 | O | GLN | B | 218 | 16.688 | 44.970 | 9.349 | 1.00 | 23.66 | 8 |
| ATOM | 746 | N | ILE | B | 219 | 16.361 | 43.806 | 11.268 | 1.00 | 22.98 | 7 |
| ATOM | 747 | CA | ILE | B | 219 | 14.909 | 43.777 | 11.054 | 1.00 | 22.46 | 6 |
| ATOM | 748 | CB | ILE | B | 219 | 14.209 | 42.791 | 11.998 | 1.00 | 24.01 | 6 |
| ATOM | 749 | CG2 | ILE | B | 219 | 14.320 | 43.076 | 13.484 | 1.00 | 23.36 | 6 |
| ATOM | 750 | CG1 | ILE | B | 219 | 12.723 | 42.606 | 11.625 | 1.00 | 27.82 | 6 |
| ATOM | 751 | CD1 | ILE | B | 219 | 12.575 | 42.170 | 10.187 | 1.00 | 28.39 | 6 |
| ATOM | 752 | C | ILE | B | 219 | 14.345 | 45.182 | 11.118 | 1.00 | 23.15 | 6 |
| ATOM | 753 | O | ILE | B | 219 | 13.418 | 45.528 | 10.374 | 1.00 | 24.69 | 8 |
| ATOM | 754 | N | ALA | B | 220 | 14.870 | 46.029 | 11.972 | 1.00 | 21.24 | 7 |
| ATOM | 755 | CA | ALA | B | 220 | 14.395 | 47.403 | 12.053 | 1.00 | 23.02 | 6 |
| ATOM | 756 | CB | ALA | B | 220 | 14.940 | 48.146 | 13.226 | 1.00 | 28.82 | 6 |
| ATOM | 757 | C | ALA | B | 220 | 14.573 | 48.131 | 10.730 | 1.00 | 23.96 | 6 |
| ATOM | 758 | O | ALA | B | 220 | 13.704 | 48.838 | 10.261 | 1.00 | 23.87 | 8 |
| ATOM | 759 | N | LYS | B | 221 | 15.767 | 47.916 | 10.161 | 1.00 | 25.79 | 7 |
| ATOM | 760 | CA | LYS | B | 221 | 16.086 | 48.555 | 8.865 | 1.00 | 26.23 | 6 |
| ATOM | 761 | CB | LYS | B | 221 | 17.518 | 48.106 | 8.505 | 1.00 | 23.73 | 6 |
| ATOM | 762 | CG | LYS | B | 221 | 17.859 | 48.602 | 7.084 | 1.00 | 32.18 | 6 |
| ATOM | 763 | CD | LYS | B | 221 | 19.349 | 48.458 | 6.835 | 1.00 | 48.70 | 6 |
| ATOM | 764 | CE | LYS | B | 221 | 19.738 | 48.828 | 5.402 | 1.00 | 49.31 | 6 |
| ATOM | 765 | NZ | LYS | B | 221 | 18.639 | 48.516 | 4.446 | 1.00 | 60.95 | 7 |
| ATOM | 766 | C | LYS | B | 221 | 15.111 | 48.086 | 7.783 | 1.00 | 26.25 | 6 |
| ATOM | 767 | O | LYS | B | 221 | 14.595 | 48.870 | 6.961 | 1.00 | 24.99 | 8 |
| ATOM | 768 | N | ASP | B | 222 | 14.904 | 46.759 | 7.727 | 1.00 | 24.13 | 7 |
| ATOM | 769 | CA | ASP | B | 222 | 13.988 | 46.167 | 6.775 | 1.00 | 23.28 | 6 |
| ATOM | 770 | CB | ASP | B | 222 | 13.982 | 44.670 | 6.968 | 1.00 | 26.58 | 6 |
| ATOM | 771 | CG | ASP | B | 222 | 15.288 | 43.945 | 6.671 | 1.00 | 37.75 | 6 |
| ATOM | 772 | OD1 | ASP | B | 222 | 16.177 | 44.545 | 6.002 | 1.00 | 35.10 | 8 |
| ATOM | 773 | OD2 | ASP | B | 222 | 15.441 | 42.777 | 7.110 | 1.00 | 31.39 | 8 |
| ATOM | 774 | C | ASP | B | 222 | 12.586 | 46.747 | 6.890 | 1.00 | 24.42 | 8 |
| ATOM | 775 | O | ASP | B | 222 | 11.842 | 46.970 | 5.918 | 1.00 | 25.24 | 8 |
| ATOM | 776 | N | VAL | B | 223 | 12.130 | 46.917 | 8.182 | 1.00 | 22.06 | 7 |
| ATOM | 777 | CA | VAL | B | 223 | 10.773 | 47.427 | 8.389 | 1.00 | 20.51 | 6 |
| ATOM | 778 | CB | VAL | B | 223 | 10.346 | 47.208 | 9.897 | 1.00 | 19.83 | 6 |
| ATOM | 779 | CG1 | VAL | B | 223 | 8.934 | 47.819 | 10.090 | 1.00 | 20.77 | 6 |
| ATOM | 780 | CG2 | VAL | B | 223 | 10.265 | 45.693 | 10.021 | 1.00 | 22.25 | 6 |
| ATOM | 781 | C | VAL | B | 223 | 10.653 | 48.898 | 8.031 | 1.00 | 21.93 | 6 |
| ATOM | 782 | O | VAL | B | 223 | 9.636 | 49.304 | 7.482 | 1.00 | 23.92 | 8 |
| ATOM | 783 | N | LYS | B | 224 | 11.687 | 49.704 | 8.307 | 1.00 | 24.30 | 7 |
| ATOM | 784 | CA | LYS | B | 224 | 11.651 | 51.102 | 7.873 | 1.00 | 22.31 | 6 |
| ATOM | 785 | CB | LYS | B | 224 | 12.864 | 51.841 | 8.430 | 1.00 | 23.89 | 6 |
| ATOM | 786 | CG | LYS | B | 224 | 12.817 | 51.931 | 9.959 | 1.00 | 26.32 | 6 |
| ATOM | 787 | CD | LYS | B | 224 | 14.034 | 52.827 | 10.307 | 1.00 | 30.62 | 6 |
| ATOM | 788 | CE | LYS | B | 224 | 14.495 | 52.556 | 11.713 | 1.00 | 36.62 | 6 |
| ATOM | 789 | NZ | LYS | B | 224 | 15.946 | 52.883 | 11.937 | 1.00 | 36.97 | 7 |
| ATOM | 790 | C | LYS | B | 224 | 11.724 | 51.116 | 6.341 | 1.00 | 22.74 | 6 |
| ATOM | 791 | O | LYS | B | 224 | 11.013 | 51.991 | 5.787 | 1.00 | 24.89 | 8 |
| ATOM | 792 | N | GLN | B | 225 | 12.380 | 50.174 | 5.720 | 1.00 | 23.32 | 7 |
| ATOM | 793 | CA | GLN | B | 225 | 12.371 | 50.203 | 4.236 | 1.00 | 25.62 | 6 |
| ATOM | 794 | CB | GLN | B | 225 | 13.406 | 49.210 | 3.710 | 1.00 | 32.12 | 6 |
| ATOM | 795 | CG | GLN | B | 225 | 13.606 | 49.177 | 2.203 | 1.00 | 38.34 | 6 |
| ATOM | 796 | CD | GLN | B | 225 | 14.606 | 48.107 | 1.788 | 1.00 | 49.03 | 6 |
| ATOM | 797 | OE1 | GLN | B | 225 | 14.901 | 47.117 | 2.477 | 1.00 | 39.12 | 8 |
| ATOM | 798 | NE2 | GLN | B | 225 | 15.160 | 48.322 | 0.591 | 1.00 | 50.68 | 7 |
| ATOM | 799 | C | GLN | B | 225 | 11.015 | 49.920 | 3.658 | 1.00 | 26.59 | 6 |
| ATOM | 800 | O | GLN | B | 225 | 10.508 | 50.492 | 2.680 | 1.00 | 27.36 | 8 |
| ATOM | 801 | N | PHE | B | 226 | 10.302 | 48.952 | 4.258 | 1.00 | 25.80 | 7 |
| ATOM | 802 | CA | PHE | B | 226 | 8.971 | 48.534 | 3.933 | 1.00 | 20.22 | 6 |
| ATOM | 803 | CB | PHE | B | 226 | 8.522 | 47.339 | 4.808 | 1.00 | 24.02 | 6 |
| ATOM | 804 | CG | PHE | B | 226 | 7.074 | 47.012 | 4.701 | 1.00 | 23.15 | 6 |

-continued

PDB FILE LISTING - cd811e1.pdb

| ATOM | 805 | CD1 | PHE | B | 226 | 6.628 | 46.093 | 3.758 | 1.00 | 31.92 | 6 |
|---|---|---|---|---|---|---|---|---|---|---|---|
| ATOM | 806 | CD2 | PHE | B | 226 | 6.116 | 47.603 | 5.521 | 1.00 | 24.40 | 6 |
| ATOM | 807 | CE1 | PHE | B | 226 | 5.300 | 45.763 | 3.633 | 1.00 | 31.15 | 6 |
| ATOM | 808 | CE2 | PHE | B | 226 | 4.777 | 47.282 | 5.405 | 1.00 | 27.17 | 6 |
| ATOM | 809 | CZ | PHE | B | 226 | 4.358 | 46.347 | 4.480 | 1.00 | 30.58 | 6 |
| ATOM | 810 | C | PHE | B | 226 | 8.048 | 49.722 | 4.129 | 1.00 | 25.25 | 6 |
| ATOM | 811 | O | PHE | B | 226 | 7.144 | 49.992 | 3.322 | 1.00 | 24.87 | 8 |
| ATOM | 812 | N | TYR | B | 227 | 8.134 | 50.368 | 5.323 | 1.00 | 23.99 | 7 |
| ATOM | 813 | CA | TYR | B | 227 | 7.292 | 51.560 | 5.541 | 1.00 | 22.94 | 6 |
| ATOM | 814 | CB | TYR | B | 227 | 7.513 | 52.055 | 6.995 | 1.00 | 24.23 | 6 |
| ATOM | 815 | CG | TYR | B | 227 | 6.875 | 53.415 | 7.212 | 1.00 | 23.07 | 6 |
| ATOM | 816 | CD1 | TYR | B | 227 | 5.501 | 53.551 | 7.469 | 1.00 | 22.96 | 6 |
| ATOM | 817 | CE1 | TYR | B | 227 | 4.873 | 54.758 | 7.629 | 1.00 | 22.01 | 6 |
| ATOM | 818 | CD2 | TYR | B | 227 | 7.591 | 54.580 | 7.177 | 1.00 | 23.12 | 6 |
| ATOM | 819 | CE2 | TYR | B | 227 | 6.985 | 55.813 | 7.341 | 1.00 | 26.09 | 6 |
| ATOM | 820 | CZ | TYR | B | 227 | 5.634 | 55.910 | 7.543 | 1.00 | 23.78 | 6 |
| ATOM | 821 | OH | TYR | B | 227 | 5.113 | 57.191 | 7.727 | 1.00 | 28.18 | 8 |
| ATOM | 822 | C | TYR | B | 227 | 7.513 | 52.644 | 4.489 | 1.00 | 21.85 | 6 |
| ATOM | 823 | O | TYR | B | 227 | 6.545 | 53.199 | 3.930 | 1.00 | 27.43 | 8 |
| ATOM | 824 | N | ASP | B | 228 | 8.769 | 52.943 | 4.220 | 1.00 | 23.83 | 7 |
| ATOM | 825 | CA | ASP | B | 228 | 9.117 | 53.991 | 3.230 | 1.00 | 25.77 | 6 |
| ATOM | 826 | CB | ASP | B | 228 | 10.610 | 54.172 | 3.106 | 1.00 | 26.19 | 6 |
| ATOM | 827 | CG | ASP | B | 228 | 11.279 | 54.729 | 4.348 | 1.00 | 27.12 | 6 |
| ATOM | 828 | OD1 | ASP | B | 228 | 10.518 | 55.146 | 5.256 | 1.00 | 28.17 | 8 |
| ATOM | 829 | OD2 | ASP | B | 228 | 12.537 | 54.751 | 4.378 | 1.00 | 31.94 | 8 |
| ATOM | 830 | C | ASP | B | 228 | 8.519 | 53.695 | 1.862 | 1.00 | 25.92 | 6 |
| ATOM | 831 | O | ASP | B | 228 | 7.956 | 54.619 | 1.257 | 1.00 | 28.03 | 8 |
| ATOM | 832 | N | GLN | B | 229 | 8.540 | 52.452 | 1.469 | 1.00 | 27.73 | 7 |
| ATOM | 833 | CA | GLN | B | 229 | 7.956 | 52.045 | 0.199 | 1.00 | 31.06 | 6 |
| ATOM | 834 | CB | GLN | B | 229 | 8.436 | 50.632 | −0.154 | 1.00 | 32.10 | 6 |
| ATOM | 835 | CG | GLN | B | 229 | 7.569 | 50.055 | −1.271 | 1.00 | 40.19 | 6 |
| ATOM | 836 | CD | GLN | B | 229 | 8.063 | 48.701 | −1.765 | 1.00 | 35.54 | 6 |
| ATOM | 837 | OE1 | GLN | B | 229 | 7.397 | 47.704 | −1.552 | 1.00 | 55.35 | 8 |
| ATOM | 838 | NE2 | GLN | B | 229 | 9.228 | 48.759 | −2.400 | 1.00 | 49.50 | 7 |
| ATOM | 839 | C | GLN | B | 229 | 6.462 | 52.183 | 0.174 | 1.00 | 29.95 | 6 |
| ATOM | 840 | O | GLN | B | 229 | 5.849 | 52.694 | −0.755 | 1.00 | 30.54 | 8 |
| ATOM | 841 | N | ALA | B | 230 | 5.752 | 51.857 | 1.285 | 1.00 | 28.41 | 7 |
| ATOM | 842 | CA | ALA | B | 230 | 4.294 | 52.032 | 1.330 | 1.00 | 24.57 | 6 |
| ATOM | 843 | CB | ALA | B | 230 | 3.798 | 51.420 | 2.650 | 1.00 | 29.26 | 6 |
| ATOM | 844 | C | ALA | B | 230 | 3.929 | 53.503 | 1.291 | 1.00 | 27.29 | 6 |
| ATOM | 845 | O | ALA | B | 230 | 2.899 | 53.939 | 0.741 | 1.00 | 30.79 | 8 |
| ATOM | 846 | N | LEU | B | 231 | 4.736 | 54.350 | 1.937 | 1.00 | 24.06 | 7 |
| ATOM | 847 | CA | LEU | B | 231 | 4.454 | 55.788 | 1.977 | 1.00 | 26.67 | 6 |
| ATOM | 848 | CB | LEU | B | 231 | 5.489 | 56.473 | 2.816 | 1.00 | 33.38 | 6 |
| ATOM | 849 | CG | LEU | B | 231 | 5.296 | 57.803 | 3.506 | 1.00 | 35.20 | 6 |
| ATOM | 850 | CD1 | LEU | B | 231 | 4.007 | 57.825 | 4.338 | 1.00 | 36.95 | 6 |
| ATOM | 851 | CD2 | LEU | B | 231 | 6.470 | 57.979 | 4.478 | 1.00 | 30.01 | 6 |
| ATOM | 852 | C | LEU | B | 231 | 4.544 | 56.325 | 0.526 | 1.00 | 28.69 | 6 |
| ATOM | 853 | O | LEU | B | 231 | 3.664 | 57.109 | 0.174 | 1.00 | 32.37 | 8 |
| ATOM | 854 | N | GLN | B | 232 | 5.594 | 55.890 | −0.151 | 1.00 | 28.25 | 7 |
| ATOM | 855 | CA | GLN | B | 232 | 5.788 | 56.301 | −1.539 | 1.00 | 26.43 | 6 |
| ATOM | 856 | CB | GLN | B | 232 | 7.123 | 55.916 | −2.154 | 1.00 | 27.83 | 6 |
| ATOM | 857 | CG | GLN | B | 232 | 7.104 | 56.319 | −3.651 | 1.00 | 40.21 | 6 |
| ATOM | 858 | CD | GLN | B | 232 | 7.235 | 57.824 | −3.813 | 1.00 | 44.86 | 6 |
| ATOM | 859 | OE1 | GLN | B | 232 | 8.250 | 58.422 | −3.452 | 1.00 | 47.98 | 8 |
| ATOM | 860 | NE2 | GLN | B | 232 | 6.207 | 58.469 | −4.365 | 1.00 | 59.78 | 7 |
| ATOM | 861 | C | GLN | B | 232 | 4.602 | 55.793 | −2.328 | 1.00 | 32.25 | 6 |
| ATOM | 862 | O | GLN | B | 232 | 3.988 | 56.547 | −3.078 | 1.00 | 34.60 | 8 |
| ATOM | 863 | N | GLN | B | 233 | 4.268 | 54.515 | −2.235 | 1.00 | 30.14 | 7 |
| ATOM | 864 | CA | GLN | B | 233 | 3.120 | 53.953 | −2.896 | 1.00 | 31.57 | 6 |
| ATOM | 865 | CB | GLN | B | 233 | 3.050 | 52.432 | −2.787 | 1.00 | 36.28 | 6 |
| ATOM | 866 | CG | GLN | B | 233 | 4.251 | 51.705 | −3.354 | 1.00 | 48.59 | 6 |
| ATOM | 867 | CD | GLN | B | 233 | 4.203 | 50.201 | −3.105 | 1.00 | 57.17 | 6 |
| ATOM | 868 | OE1 | GLN | B | 233 | 3.292 | 49.661 | −2.475 | 1.00 | 55.45 | 8 |
| ATOM | 869 | NE2 | GLN | B | 233 | 5.212 | 49.490 | −3.609 | 1.00 | 52.72 | 7 |
| ATOM | 870 | C | GLN | B | 233 | 1.795 | 54.588 | −2.597 | 1.00 | 36.59 | 6 |
| ATOM | 871 | O | GLN | B | 233 | 0.978 | 54.775 | −3.490 | 1.00 | 33.24 | 8 |
| ATOM | 872 | N | ALA | B | 234 | 1.500 | 54.941 | −1.342 | 1.00 | 34.08 | 7 |
| ATOM | 873 | CA | ALA | B | 234 | 0.236 | 55.543 | −0.953 | 1.00 | 31.39 | 6 |
| ATOM | 874 | CB | ALA | B | 234 | 0.233 | 55.805 | 0.554 | 1.00 | 38.61 | 6 |
| ATOM | 875 | C | ALA | B | 234 | −0.023 | 56.910 | −1.579 | 1.00 | 37.11 | 6 |
| ATOM | 876 | O | ALA | B | 234 | −1.162 | 57.369 | −1.539 | 1.00 | 40.52 | 8 |
| ATOM | 877 | N | VAL | B | 235 | 1.020 | 57.582 | −1.993 | 1.00 | 35.31 | 7 |
| ATOM | 878 | CA | VAL | B | 235 | 0.886 | 58.936 | −2.523 | 1.00 | 45.20 | 6 |
| ATOM | 879 | CB | VAL | B | 235 | 2.237 | 59.674 | −2.510 | 1.00 | 45.97 | 6 |
| ATOM | 880 | CG1 | VAL | B | 235 | 2.240 | 60.797 | −3.520 | 1.00 | 57.51 | 6 |
| ATOM | 881 | CG2 | VAL | B | 235 | 2.552 | 60.112 | −1.095 | 1.00 | 52.58 | 6 |

-continued

PDB FILE LISTING - cd811e1.pdb

| ATOM | 882 | C | VAL | B | 235 | 0.303 | 58.949 | −3.917 | 1.00 | 47.01 | 6 |
|------|-----|-----|-----|---|-----|--------|--------|---------|------|-------|---|
| ATOM | 883 | O | VAL | B | 235 | −0.462 | 59.839 | −4.250 | 1.00 | 44.05 | 8 |
| ATOM | 884 | N | VAL | B | 236 | 0.545 | 57.898 | −4.675 | 1.00 | 53.53 | 7 |
| ATOM | 885 | CA | VAL | B | 236 | 0.086 | 57.778 | −6.044 | 1.00 | 60.39 | 6 |
| ATOM | 886 | CB | VAL | B | 236 | 1.147 | 57.008 | −6.861 | 1.00 | 61.99 | 6 |
| ATOM | 887 | CG1 | VAL | B | 236 | 2.528 | 57.201 | −6.254 | 1.00 | 60.20 | 6 |
| ATOM | 888 | CG2 | VAL | B | 236 | 0.778 | 55.535 | −6.904 | 1.00 | 55.70 | 6 |
| ATOM | 889 | C | VAL | B | 236 | −1.253 | 57.088 | −6.212 | 1.00 | 62.78 | 6 |
| ATOM | 890 | O | VAL | B | 236 | −1.887 | 56.597 | −5.282 | 1.00 | 63.95 | 8 |
| ATOM | 891 | N | ASP | B | 237 | −1.720 | 57.051 | −7.456 | 1.00 | 65.68 | 7 |
| ATOM | 892 | CA | ASP | B | 237 | −2.972 | 56.428 | −7.831 | 1.00 | 67.82 | 6 |
| ATOM | 893 | CB | ASP | B | 237 | −2.741 | 54.984 | −8.278 | 1.00 | 72.56 | 6 |
| ATOM | 894 | CG | ASP | B | 237 | −2.597 | 54.853 | −9.782 | 1.00 | 75.01 | 6 |
| ATOM | 895 | OD1 | ASP | B | 237 | −2.837 | 55.847 | −10.500 | 1.00 | 71.57 | 8 |
| ATOM | 896 | OD2 | ASP | B | 237 | −2.249 | 53.743 | −10.241 | 1.00 | 73.99 | 8 |
| ATOM | 897 | C | ASP | B | 237 | −4.041 | 56.492 | −6.756 | 1.00 | 67.93 | 6 |
| ATOM | 898 | O | ASP | B | 237 | −3.990 | 57.440 | −5.938 | 1.00 | 69.24 | 8 |
| ATOM | 899 | CB | ASN | C | 242 | −2.832 | 47.036 | −0.049 | 1.00 | 52.44 | 6 |
| ATOM | 900 | CG | ASN | C | 242 | −3.531 | 46.708 | 1.256 | 1.00 | 53.59 | 6 |
| ATOM | 901 | OD1 | ASN | C | 242 | −4.754 | 46.644 | 1.309 | 1.00 | 68.85 | 8 |
| ATOM | 902 | ND2 | ASN | C | 242 | −2.755 | 46.521 | 2.306 | 1.00 | 62.22 | 7 |
| ATOM | 903 | C | ASN | C | 242 | −2.213 | 49.417 | 0.387 | 1.00 | 39.79 | 6 |
| ATOM | 904 | O | ASN | C | 242 | −2.332 | 49.370 | 1.630 | 1.00 | 39.72 | 8 |
| ATOM | 905 | N | ASN | C | 242 | −3.171 | 48.676 | −1.871 | 1.00 | 39.76 | 7 |
| ATOM | 906 | CA | ASN | C | 242 | −3.103 | 48.497 | −0.415 | 1.00 | 43.08 | 6 |
| ATOM | 907 | N | ALA | C | 243 | −1.401 | 50.254 | −0.254 | 1.00 | 36.60 | 7 |
| ATOM | 908 | CA | ALA | C | 243 | −0.491 | 51.133 | 0.430 | 1.00 | 34.21 | 6 |
| ATOM | 909 | CB | ALA | C | 243 | 0.480 | 51.825 | −0.534 | 1.00 | 32.11 | 6 |
| ATOM | 910 | C | ALA | C | 243 | −1.151 | 52.133 | 1.366 | 1.00 | 36.65 | 6 |
| ATOM | 911 | O | ALA | C | 243 | −0.621 | 52.349 | 2.471 | 1.00 | 33.63 | 8 |
| ATOM | 912 | N | LYS | C | 244 | −2.309 | 52.694 | 0.990 | 1.00 | 31.22 | 7 |
| ATOM | 913 | CA | LYS | C | 244 | −2.931 | 53.638 | 1.903 | 1.00 | 35.12 | 6 |
| ATOM | 914 | CB | LYS | C | 244 | −4.102 | 54.402 | 1.304 | 1.00 | 38.30 | 6 |
| ATOM | 915 | CG | LYS | C | 244 | −3.677 | 55.244 | 0.096 | 1.00 | 47.69 | 6 |
| ATOM | 916 | CD | LYS | C | 244 | −4.704 | 56.314 | −0.233 | 1.00 | 59.26 | 6 |
| ATOM | 917 | CE | LYS | C | 244 | −4.248 | 57.259 | −1.342 | 1.00 | 45.56 | 6 |
| ATOM | 918 | NZ | LYS | C | 244 | −3.736 | 56.493 | −2.515 | 1.00 | 48.06 | 7 |
| ATOM | 919 | C | LYS | C | 244 | −3.251 | 52.942 | 3.219 | 1.00 | 31.26 | 6 |
| ATOM | 920 | O | LYS | C | 244 | −3.045 | 53.522 | 4.294 | 1.00 | 37.97 | 8 |
| ATOM | 921 | N | ALA | C | 245 | −3.851 | 51.759 | 3.155 | 1.00 | 35.96 | 7 |
| ATOM | 922 | CA | ALA | C | 245 | −4.202 | 51.044 | 4.371 | 1.00 | 35.05 | 6 |
| ATOM | 923 | CB | ALA | C | 245 | −5.204 | 49.931 | 4.208 | 1.00 | 37.25 | 6 |
| ATOM | 924 | C | ALA | C | 245 | −2.983 | 50.617 | 5.184 | 1.00 | 32.82 | 6 |
| ATOM | 925 | O | ALA | C | 245 | −3.059 | 50.740 | 6.420 | 1.00 | 29.94 | 8 |
| ATOM | 926 | N | VAL | C | 246 | −1.907 | 50.246 | 4.499 | 1.00 | 33.79 | 7 |
| ATOM | 927 | CA | VAL | C | 246 | −0.705 | 49.866 | 5.266 | 1.00 | 29.90 | 6 |
| ATOM | 928 | CB | VAL | C | 246 | 0.366 | 49.269 | 4.369 | 1.00 | 29.88 | 6 |
| ATOM | 929 | CG1 | VAL | C | 246 | 0.056 | 47.917 | 3.771 | 1.00 | 34.43 | 6 |
| ATOM | 930 | CG2 | VAL | C | 246 | 1.773 | 49.346 | 4.931 | 1.00 | 29.74 | 6 |
| ATOM | 931 | C | VAL | C | 246 | −0.168 | 51.083 | 5.984 | 1.00 | 30.62 | 6 |
| ATOM | 932 | O | VAL | C | 246 | 0.208 | 51.067 | 7.166 | 1.00 | 29.83 | 8 |
| ATOM | 933 | N | VAL | C | 247 | −0.095 | 52.225 | 5.269 | 1.00 | 28.26 | 7 |
| ATOM | 934 | CA | VAL | C | 247 | 0.348 | 53.468 | 5.911 | 1.00 | 25.89 | 6 |
| ATOM | 935 | CB | VAL | C | 247 | 0.316 | 54.634 | 4.873 | 1.00 | 32.16 | 6 |
| ATOM | 936 | CG1 | VAL | C | 247 | 0.468 | 55.966 | 5.600 | 1.00 | 29.03 | 6 |
| ATOM | 937 | CG2 | VAL | C | 247 | 1.529 | 54.419 | 3.961 | 1.00 | 37.46 | 6 |
| ATOM | 938 | C | VAL | C | 247 | −0.533 | 53.832 | 7.100 | 1.00 | 28.13 | 6 |
| ATOM | 939 | O | VAL | C | 247 | −0.035 | 54.171 | 8.176 | 1.00 | 27.03 | 8 |
| ATOM | 940 | N | LYS | C | 248 | −1.851 | 53.790 | 6.935 | 1.00 | 25.46 | 7 |
| ATOM | 941 | CA | LYS | C | 248 | −2.739 | 54.143 | 8.033 | 1.00 | 28.62 | 6 |
| ATOM | 942 | CB | LYS | C | 248 | −4.215 | 54.072 | 7.623 | 1.00 | 41.92 | 6 |
| ATOM | 943 | CG | LYS | C | 248 | −5.117 | 54.460 | 8.801 | 1.00 | 55.47 | 6 |
| ATOM | 944 | CD | LYS | C | 248 | −6.509 | 53.868 | 8.678 | 1.00 | 53.90 | 6 |
| ATOM | 945 | CE | LYS | C | 248 | −7.538 | 54.663 | 9.470 | 1.00 | 57.26 | 6 |
| ATOM | 946 | NZ | LYS | C | 248 | −7.729 | 56.016 | 8.867 | 1.00 | 64.95 | 7 |
| ATOM | 947 | C | LYS | C | 248 | −2.548 | 53.220 | 9.240 | 1.00 | 27.15 | 6 |
| ATOM | 948 | O | LYS | C | 248 | −2.552 | 53.715 | 10.363 | 1.00 | 27.05 | 8 |
| ATOM | 949 | N | THR | C | 249 | −2.356 | 51.947 | 8.963 | 1.00 | 27.77 | 7 |
| ATOM | 950 | CA | THR | C | 249 | −2.134 | 50.940 | 9.998 | 1.00 | 25.68 | 6 |
| ATOM | 951 | CB | THR | C | 249 | −2.085 | 49.544 | 9.335 | 1.00 | 32.70 | 6 |
| ATOM | 952 | OG1 | THR | C | 249 | −3.453 | 49.231 | 8.992 | 1.00 | 33.92 | 8 |
| ATOM | 953 | CG2 | THR | C | 249 | −1.680 | 48.496 | 10.385 | 1.00 | 28.13 | 6 |
| ATOM | 954 | C | THR | C | 249 | −0.862 | 51.225 | 10.734 | 1.00 | 21.92 | 6 |
| ATOM | 955 | O | THR | C | 249 | −0.862 | 51.153 | 11.973 | 1.00 | 26.37 | 8 |
| ATOM | 956 | N | PHE | C | 250 | 0.224 | 51.510 | 10.052 | 1.00 | 24.01 | 7 |
| ATOM | 957 | CA | PHE | C | 250 | 1.452 | 51.874 | 10.753 | 1.00 | 22.16 | 6 |
| ATOM | 958 | CB | PHE | C | 250 | 2.617 | 51.986 | 9.764 | 1.00 | 23.90 | 6 |

-continued

| PDB FILE LISTING - cd811e1.pdb | | | | | | | | | | |
|---|---|---|---|---|---|---|---|---|---|---|
| ATOM | 959 | CG | PHE | C | 250 | 3.359 | 50.719 | 9.523 | 1.00 | 20.12 | 6 |
| ATOM | 960 | CD1 | PHE | C | 250 | 2.740 | 49.629 | 8.943 | 1.00 | 26.67 | 6 |
| ATOM | 961 | CD2 | PHE | C | 250 | 4.703 | 50.639 | 9.883 | 1.00 | 24.12 | 6 |
| ATOM | 962 | CE1 | PHE | C | 250 | 3.448 | 48.448 | 8.753 | 1.00 | 25.84 | 6 |
| ATOM | 963 | CE2 | PHE | C | 250 | 5.393 | 49.449 | 9.704 | 1.00 | 26.95 | 6 |
| ATOM | 964 | CZ | PHE | C | 250 | 4.788 | 48.377 | 9.098 | 1.00 | 26.24 | 6 |
| ATOM | 965 | C | PHE | C | 250 | 1.272 | 53.105 | 11.613 | 1.00 | 23.98 | 6 |
| ATOM | 966 | O | PHE | C | 250 | 1.713 | 53.163 | 12.779 | 1.00 | 23.60 | 8 |
| ATOM | 967 | N | HIS | C | 251 | 0.654 | 54.143 | 11.040 | 1.00 | 23.00 | 7 |
| ATOM | 968 | CA | HIS | C | 251 | 0.506 | 55.406 | 11.779 | 1.00 | 24.29 | 6 |
| ATOM | 969 | CB | HIS | C | 251 | −0.108 | 56.474 | 10.895 | 1.00 | 28.22 | 6 |
| ATOM | 970 | CG | HIS | C | 251 | 0.848 | 56.857 | 9.809 | 1.00 | 22.07 | 6 |
| ATOM | 971 | CD2 | HIS | C | 251 | 2.172 | 56.586 | 9.687 | 1.00 | 20.33 | 6 |
| ATOM | 972 | ND1 | HIS | C | 251 | 0.474 | 57.604 | 8.733 | 1.00 | 27.95 | 7 |
| ATOM | 973 | CE1 | HIS | C | 251 | 1.546 | 57.774 | 7.977 | 1.00 | 24.46 | 6 |
| ATOM | 974 | NE2 | HIS | C | 251 | 2.594 | 57.162 | 8.476 | 1.00 | 23.12 | 7 |
| ATOM | 975 | C | HIS | C | 251 | −0.307 | 55.195 | 13.030 | 1.00 | 20.90 | 6 |
| ATOM | 976 | O | HIS | C | 251 | 0.070 | 55.675 | 14.085 | 1.00 | 27.74 | 8 |
| ATOM | 977 | N | GLU | C | 252 | −1.409 | 54.479 | 12.901 | 1.00 | 24.95 | 7 |
| ATOM | 978 | CA | GLU | C | 252 | −2.287 | 54.246 | 14.059 | 1.00 | 28.46 | 6 |
| ATOM | 979 | CB | GLU | C | 252 | −3.544 | 53.531 | 13.532 | 1.00 | 33.82 | 6 |
| ATOM | 980 | CG | GLU | C | 252 | −4.584 | 54.560 | 13.085 | 1.00 | 50.99 | 6 |
| ATOM | 981 | CD | GLU | C | 252 | −5.218 | 55.177 | 14.320 | 1.00 | 58.60 | 6 |
| ATOM | 982 | OE1 | GLU | C | 252 | −5.078 | 54.538 | 15.384 | 1.00 | 71.21 | 8 |
| ATOM | 983 | OE2 | GLU | C | 252 | −5.827 | 56.258 | 14.217 | 1.00 | 74.51 | 8 |
| ATOM | 984 | C | GLU | C | 252 | −1.649 | 53.320 | 15.076 | 1.00 | 25.23 | 6 |
| ATOM | 985 | O | GLU | C | 252 | −1.725 | 53.623 | 16.292 | 1.00 | 27.62 | 8 |
| ATOM | 986 | N | THR | C | 253 | −0.948 | 52.285 | 14.608 | 1.00 | 24.22 | 7 |
| ATOM | 987 | CA | THR | C | 253 | −0.336 | 51.351 | 15.541 | 1.00 | 25.24 | 6 |
| ATOM | 988 | CB | THR | C | 253 | 0.122 | 50.084 | 14.769 | 1.00 | 30.19 | 6 |
| ATOM | 989 | OG1 | THR | C | 253 | −1.087 | 49.511 | 14.236 | 1.00 | 29.93 | 8 |
| ATOM | 990 | CG2 | THR | C | 253 | 0.659 | 49.055 | 15.758 | 1.00 | 29.01 | 6 |
| ATOM | 991 | C | THR | C | 253 | 0.830 | 51.942 | 16.282 | 1.00 | 26.99 | 6 |
| ATOM | 992 | O | THR | C | 253 | 0.987 | 51.670 | 17.488 | 1.00 | 26.85 | 8 |
| ATOM | 993 | N | LEU | C | 254 | 1.663 | 52.716 | 15.590 | 1.00 | 25.36 | 7 |
| ATOM | 994 | CA | LEU | C | 254 | 2.892 | 53.221 | 16.188 | 1.00 | 25.88 | 6 |
| ATOM | 995 | CB | LEU | C | 254 | 4.109 | 53.104 | 15.238 | 1.00 | 26.52 | 6 |
| ATOM | 996 | CG | LEU | C | 254 | 4.359 | 51.782 | 14.532 | 1.00 | 28.64 | 6 |
| ATOM | 997 | CD1 | LEU | C | 254 | 5.319 | 51.868 | 13.356 | 1.00 | 26.29 | 6 |
| ATOM | 998 | CD2 | LEU | C | 254 | 4.785 | 50.714 | 15.546 | 1.00 | 31.46 | 6 |
| ATOM | 999 | C | LEU | C | 254 | 2.771 | 54.634 | 16.713 | 1.00 | 23.22 | 6 |
| ATOM | 1000 | O | LEU | C | 254 | 3.703 | 55.129 | 17.323 | 1.00 | 29.91 | 8 |
| ATOM | 1001 | N | ASP | C | 255 | 1.650 | 55.306 | 16.425 | 1.00 | 26.04 | 7 |
| ATOM | 1002 | CA | ASP | C | 255 | 1.388 | 56.653 | 16.899 | 1.00 | 28.87 | 6 |
| ATOM | 1003 | CB | ASP | C | 255 | 1.580 | 56.705 | 18.457 | 1.00 | 27.97 | 6 |
| ATOM | 1004 | CG | ASP | C | 255 | 0.731 | 57.830 | 19.007 | 1.00 | 38.75 | 6 |
| ATOM | 1005 | OD1 | ASP | C | 255 | −0.377 | 58.016 | 18.460 | 1.00 | 39.85 | 8 |
| ATOM | 1006 | OD2 | ASP | C | 255 | 1.167 | 58.483 | 19.981 | 1.00 | 49.40 | 8 |
| ATOM | 1007 | C | ASP | C | 255 | 2.398 | 57.629 | 16.324 | 1.00 | 26.53 | 6 |
| ATOM | 1008 | O | ASP | C | 255 | 3.180 | 58.334 | 16.965 | 1.00 | 30.14 | 8 |
| ATOM | 1009 | N | CYS | C | 256 | 2.413 | 57.598 | 14.957 | 1.00 | 23.58 | 7 |
| ATOM | 1010 | CA | CYS | C | 256 | 3.298 | 58.532 | 14.225 | 1.00 | 23.99 | 6 |
| ATOM | 1011 | C | CYS | C | 256 | 2.648 | 58.853 | 12.873 | 1.00 | 23.60 | 6 |
| ATOM | 1012 | O | CYS | C | 256 | 1.527 | 58.447 | 12.512 | 1.00 | 25.41 | 8 |
| ATOM | 1013 | CB | CYS | C | 256 | 4.637 | 57.834 | 13.913 | 1.00 | 27.13 | 6 |
| ATOM | 1014 | SG | CYS | C | 256 | 4.516 | 56.303 | 12.969 | 1.00 | 25.36 | 16 |
| ATOM | 1015 | N | CYS | C | 257 | 3.385 | 59.714 | 12.151 | 1.00 | 24.12 | 7 |
| ATOM | 1016 | CA | CYS | C | 257 | 2.892 | 60.177 | 10.853 | 1.00 | 23.16 | 6 |
| ATOM | 1017 | C | CYS | C | 257 | 4.139 | 60.542 | 10.014 | 1.00 | 24.72 | 6 |
| ATOM | 1018 | O | CYS | C | 257 | 4.847 | 61.504 | 10.308 | 1.00 | 35.05 | 8 |
| ATOM | 1019 | CB | CYS | C | 257 | 2.010 | 61.419 | 11.084 | 1.00 | 25.12 | 6 |
| ATOM | 1020 | SG | CYS | C | 257 | 1.467 | 62.126 | 9.517 | 1.00 | 38.79 | 16 |
| ATOM | 1021 | N | GLY | C | 258 | 4.489 | 59.747 | 9.012 | 1.00 | 28.13 | 7 |
| ATOM | 1022 | CA | GLY | C | 258 | 5.588 | 60.028 | 8.166 | 1.00 | 29.38 | 6 |
| ATOM | 1023 | C | GLY | C | 258 | 6.986 | 59.897 | 8.749 | 1.00 | 27.80 | 6 |
| ATOM | 1024 | O | GLY | C | 258 | 7.302 | 59.270 | 9.763 | 1.00 | 27.20 | 8 |
| ATOM | 1025 | N | SER | C | 259 | 7.907 | 60.517 | 7.979 | 1.00 | 23.88 | 7 |
| ATOM | 1026 | CA | SER | C | 259 | 9.319 | 60.378 | 8.276 | 1.00 | 24.44 | 6 |
| ATOM | 1027 | CB | SER | C | 259 | 9.939 | 59.307 | 7.342 | 1.00 | 24.84 | 6 |
| ATOM | 1028 | OG | SER | C | 259 | 11.346 | 59.213 | 7.645 | 1.00 | 24.95 | 8 |
| ATOM | 1029 | C | SER | C | 259 | 10.034 | 61.697 | 8.068 | 1.00 | 23.27 | 6 |
| ATOM | 1030 | O | SER | C | 259. | 9.868 | 62.267 | 6.973 | 1.00 | 25.69 | 8 |
| ATOM | 1031 | N | SER | C | 260 | 10.980 | 62.031 | 8.914 | 1.00 | 23.41 | 7 |
| ATOM | 1032 | CA | SER | C | 260 | 11.848 | 63.181 | 8.666 | 1.00 | 26.33 | 6 |
| ATOM | 1033 | CB | SER | C | 260 | 12.884 | 63.261 | 9.785 | 1.00 | 27.51 | 6 |
| ATOM | 1034 | OG | SER | C | 260 | 12.179 | 63.570 | 10.989 | 1.00 | 28.13 | 8 |
| ATOM | 1035 | C | SER | C | 260 | 12.676 | 63.039 | 7.371 | 1.00 | 29.57 | 6 |

-continued

| | | | | | | | | | | |
|---|---|---|---|---|---|---|---|---|---|---|
| \multicolumn{11}{c}{PDB FILE LISTING - cd811e1.pdb} |
| ATOM | 1036 | O | SER | C | 260 | 13.077 | 64.066 | 6.849 | 1.00 | 30.79 | 8 |
| ATOM | 1037 | N | THR | C | 261 | 12.896 | 61.841 | 6.873 | 1.00 | 26.07 | 7 |
| ATOM | 1038 | CA | THR | C | 261 | 13.692 | 61.604 | 5.669 | 1.00 | 27.09 | 6 |
| ATOM | 1039 | CB | THR | C | 261 | 14.272 | 60.165 | 5.682 | 1.00 | 33.47 | 6 |
| ATOM | 1040 | OG1 | THR | C | 261 | 13.261 | 59.151 | 5.651 | 1.00 | 27.38 | 8 |
| ATOM | 1041 | CG2 | THR | C | 261 | 15.173 | 59.975 | 6.879 | 1.00 | 32.39 | 6 |
| ATOM | 1042 | C | THR | C | 261 | 12.864 | 61.784 | 4.414 | 1.00 | 28.01 | 6 |
| ATOM | 1043 | O | THR | C | 261 | 13.421 | 61.744 | 3.288 | 1.00 | 30.80 | 8 |
| ATOM | 1044 | N | LEU | C | 262 | 11.552 | 61.893 | 4.543 | 1.00 | 24.40 | 7 |
| ATOM | 1045 | CA | LEU | C | 262 | 10.639 | 61.952 | 3.428 | 1.00 | 25.43 | 6 |
| ATOM | 1046 | CB | LEU | C | 262 | 9.914 | 60.611 | 3.138 | 1.00 | 28.21 | 6 |
| ATOM | 1047 | CG | LEU | C | 262 | 10.883 | 59.510 | 2.708 | 1.00 | 26.53 | 6 |
| ATOM | 1048 | CD1 | LEU | C | 262 | 10.350 | 58.121 | 2.895 | 1.00 | 30.08 | 6 |
| ATOM | 1049 | CD2 | LEU | C | 262 | 11.259 | 59.683 | 1.219 | 1.00 | 28.90 | 6 |
| ATOM | 1050 | C | LEU | C | 262 | 9.616 | 63.049 | 3.657 | 1.00 | 23.19 | 6 |
| ATOM | 1051 | O | LEU | C | 262 | 8.439 | 62.766 | 3.792 | 1.00 | 26.41 | 8 |
| ATOM | 1052 | N | THR | C | 263 | 10.094 | 64.280 | 3.767 | 1.00 | 26.39 | 7 |
| ATOM | 1053 | CA | THR | C | 263 | 9.161 | 65.386 | 4.059 | 1.00 | 27.72 | 6 |
| ATOM | 1054 | CB | THR | C | 263 | 9.896 | 66.696 | 4.405 | 1.00 | 25.97 | 6 |
| ATOM | 1055 | OG1 | THR | C | 263 | 10.729 | 66.986 | 3.282 | 1.00 | 30.14 | 8 |
| ATOM | 1056 | CG2 | THR | C | 263 | 10.827 | 66.427 | 5.589 | 1.00 | 27.82 | 6 |
| ATOM | 1057 | C | THR | C | 263 | 8.032 | 65.629 | 3.102 | 1.00 | 26.70 | 6 |
| ATOM | 1058 | O | THR | C | 263 | 6.878 | 65.844 | 3.504 | 1.00 | 28.71 | 8 |
| ATOM | 1059 | N | ALA | C | 264 | 8.304 | 65.522 | 1.773 | 1.00 | 26.68 | 7 |
| ATOM | 1060 | CA | ALA | C | 264 | 7.204 | 65.683 | 0.833 | 1.00 | 28.81 | 6 |
| ATOM | 1061 | CB | ALA | C | 264 | 7.792 | 65.684 | −0.583 | 1.00 | 37.35 | 6 |
| ATOM | 1062 | C | ALA | C | 264 | 6.131 | 64.613 | 0.943 | 1.00 | 29.88 | 6 |
| ATOM | 1063 | O | ALA | C | 264 | 4.928 | 64.893 | 0.823 | 1.00 | 27.29 | 8 |
| ATOM | 1064 | N | LEU | C | 265 | 6.556 | 63.336 | 1.110 | 1.00 | 26.34 | 7 |
| ATOM | 1065 | CA | LEU | C | 265 | 5.538 | 62.287 | 1.253 | 1.00 | 25.11 | 6 |
| ATOM | 1066 | CB | LEU | C | 265 | 6.196 | 60.887 | 1.270 | 1.00 | 28.31 | 6 |
| ATOM | 1067 | CG | LEU | C | 265 | 6.907 | 60.588 | −0.062 | 1.00 | 29.73 | 6 |
| ATOM | 1068 | CD1 | LEU | C | 265 | 7.569 | 59.240 | 0.095 | 1.00 | 33.59 | 6 |
| ATOM | 1069 | CD2 | LEU | C | 265 | 5.839 | 60.531 | −1.146 | 1.00 | 28.63 | 6 |
| ATOM | 1070 | C | LEU | C | 265 | 4.751 | 62.425 | 2.549 | 1.00 | 23.39 | 6 |
| ATOM | 1071 | O | LEU | C | 265 | 3.559 | 62.162 | 2.563 | 1.00 | 26.66 | 8 |
| ATOM | 1072 | N | THR | C | 266 | 5.439 | 63.023 | 3.542 | 1.00 | 25.29 | 7 |
| ATOM | 1073 | CA | THR | C | 266 | 4.716 | 63.271 | 4.808 | 1.00 | 22.08 | 6 |
| ATOM | 1074 | CB | THR | C | 266 | 5.727 | 63.729 | 5.881 | 1.00 | 23.25 | 6 |
| ATOM | 1075 | OG1 | THR | C | 266 | 6.648 | 62.625 | 6.056 | 1.00 | 25.07 | 8 |
| ATOM | 1076 | CG2 | THR | C | 266 | 5.058 | 63.990 | 7.240 | 1.00 | 23.91 | 6 |
| ATOM | 1077 | C | THR | C | 266 | 3.654 | 64.375 | 4.578 | 1.00 | 22.75 | 6 |
| ATOM | 1078 | O | THR | C | 266 | 2.556 | 64.260 | 5.081 | 1.00 | 28.42 | 8 |
| ATOM | 1079 | N | THR | C | 267 | 4.040 | 65.386 | 3.793 | 1.00 | 25.87 | 7 |
| ATOM | 1080 | CA | THR | C | 267 | 3.019 | 66.421 | 3.509 | 1.00 | 26.21 | 6 |
| ATOM | 1081 | CB | THR | C | 267 | 3.635 | 67.461 | 2.586 | 1.00 | 28.25 | 6 |
| ATOM | 1082 | OG1 | THR | C | 267 | 4.745 | 68.101 | 3.197 | 1.00 | 28.51 | 8 |
| ATOM | 1083 | CG2 | THR | C | 267 | 2.581 | 68.472 | 2.123 | 1.00 | 27.94 | 6 |
| ATOM | 1084 | C | THR | C | 267 | 1.818 | 65.733 | 2.855 | 1.00 | 27.78 | 6 |
| ATOM | 1085 | O | THR | C | 267 | 0.690 | 65.985 | 3.208 | 1.00 | 29.01 | 8 |
| ATOM | 1086 | N | SER | C | 268 | 2.094 | 64.819 | 1.906 | 1.00 | 27.61 | 7 |
| ATOM | 1087 | CA | SER | C | 268 | 0.979 | 64.143 | 1.229 | 1.00 | 25.35 | 6 |
| ATOM | 1088 | CB | SER | C | 268 | 1.548 | 63.536 | −0.058 | 1.00 | 32.95 | 6 |
| ATOM | 1089 | OG | SER | C | 268 | 0.564 | 62.685 | −0.630 | 1.00 | 44.07 | 8 |
| ATOM | 1090 | C | SER | C | 268 | 0.101 | 63.347 | 2.138 | 1.00 | 30.80 | 6 |
| ATOM | 1091 | O | SER | C | 268 | −1.147 | 63.435 | 2.174 | 1.00 | 33.02 | 8 |
| ATOM | 1092 | N | VAL | C | 269 | 0.728 | 62.580 | 3.065 | 1.00 | 27.58 | 7 |
| ATOM | 1093 | CA | VAL | C | 269 | −0.081 | 61.844 | 4.023 | 1.00 | 34.13 | 6 |
| ATOM | 1094 | CB | VAL | C | 269 | 0.621 | 60.665 | 4.655 | 1.00 | 38.22 | 6 |
| ATOM | 1095 | CG1 | VAL | C | 269 | 0.872 | 59.601 | 3.584 | 1.00 | 45.09 | 6 |
| ATOM | 1096 | CG2 | VAL | C | 269 | 1.899 | 61.022 | 5.375 | 1.00 | 44.36 | 6 |
| ATOM | 1097 | C | VAL | C | 269 | −0.922 | 62.762 | 4.888 | 1.00 | 30.87 | 6 |
| ATOM | 1098 | O | VAL | C | 269 | −2.068 | 62.347 | 5.141 | 1.00 | 33.47 | 8 |
| ATOM | 1099 | N | LEU | C | 270 | −0.426 | 63.946 | 5.266 | 1.00 | 28.56 | 7 |
| ATOM | 1100 | CA | LEU | C | 270 | −1.285 | 64.827 | 6.067 | 1.00 | 30.65 | 6 |
| ATOM | 1101 | CB | LEU | C | 270 | −0.460 | 66.044 | 6.549 | 1.00 | 36.56 | 6 |
| ATOM | 1102 | CG | LEU | C | 270 | 0.538 | 65.662 | 7.647 | 1.00 | 34.36 | 6 |
| ATOM | 1103 | CD1 | LEU | C | 270 | 1.529 | 66.803 | 7.862 | 1.00 | 41.70 | 6 |
| ATOM | 1104 | CD2 | LEU | C | 270 | −0.232 | 65.408 | 8.925 | 1.00 | 35.94 | 6 |
| ATOM | 1105 | C | LEU | C | 270 | −2.396 | 65.387 | 5.189 | 1.00 | 33.16 | 6 |
| ATOM | 1106 | O | LEU | C | 270 | −3.505 | 65.574 | 5.686 | 1.00 | 45.89 | 8 |
| ATOM | 1107 | N | LYS | C | 271 | −2.124 | 65.660 | 3.938 | 1.00 | 34.32 | 7 |
| ATOM | 1108 | CA | LYS | C | 271 | −3.134 | 66.246 | 3.050 | 1.00 | 41.10 | 6 |
| ATOM | 1109 | CB | LYS | C | 271 | −2.472 | 66.769 | 1.783 | 1.00 | 32.67 | 6 |
| ATOM | 1110 | CG | LYS | C | 271 | −2.127 | 68.233 | 1.717 | 1.00 | 43.61 | 6 |
| ATOM | 1111 | CD | LYS | C | 271 | −0.952 | 68.551 | 0.830 | 1.00 | 50.73 | 6 |
| ATOM | 1112 | CE | LYS | C | 271 | −1.260 | 69.015 | −0.572 | 1.00 | 54.10 | 6 |

-continued

PDB FILE LISTING - cd811e1.pdb

| ATOM | 1113 | NZ | LYS | C | 271 | −0.039 | 69.130 | −1.431 | 1.00 | 56.13 | 7 |
|------|------|-----|-----|---|-----|--------|--------|--------|------|-------|---|
| ATOM | 1114 | C | LYS | C | 271 | −4.193 | 65.214 | 2.672 | 1.00 | 46.38 | 6 |
| ATOM | 1115 | O | LYS | C | 271 | −5.236 | 65.554 | 2.114 | 1.00 | 47.27 | 8 |
| ATOM | 1116 | N | ASN | C | 272 | −3.879 | 63.946 | 2.880 | 1.00 | 45.09 | 7 |
| ATOM | 1117 | CA | ASN | C | 272 | −4.778 | 62.853 | 2.522 | 1.00 | 43.41 | 6 |
| ATOM | 1118 | CB | ASN | C | 272 | −4.086 | 61.857 | 1.593 | 1.00 | 50.61 | 6 |
| ATOM | 1119 | CG | ASN | C | 272 | −3.723 | 62.457 | 0.250 | 1.00 | 49.74 | 6 |
| ATOM | 1120 | OD1 | ASN | C | 272 | −2.963 | 61.847 | −0.503 | 1.00 | 60.30 | 8 |
| ATOM | 1121 | ND2 | ASN | C | 272 | −4.256 | 63.636 | −0.037 | 1.00 | 52.35 | 7 |
| ATOM | 1122 | C | ASN | C | 272 | −5.367 | 62.117 | 3.710 | 1.00 | 42.86 | 6 |
| ATOM | 1123 | O | ASN | C | 272 | −5.855 | 60.989 | 3.575 | 1.00 | 42.83 | 8 |
| ATOM | 1124 | N | ASN | C | 273 | −5.378 | 62.712 | 4.895 | 1.00 | 42.22 | 7 |
| ATOM | 1125 | CA | ASN | C | 273 | −5.956 | 62.073 | 6.073 | 1.00 | 44.58 | 6 |
| ATOM | 1126 | CB | ASN | C | 273 | −7.465 | 62.188 | 6.138 | 1.00 | 52.14 | 6 |
| ATOM | 1127 | CG | ASN | C | 273 | −8.169 | 61.943 | 7.449 | 1.00 | 66.60 | 6 |
| ATOM | 1128 | OD1 | ASN | C | 273 | −9.311 | 61.452 | 7.442 | 1.00 | 61.59 | 8 |
| ATOM | 1129 | ND2 | ASN | C | 273 | −7.599 | 62.249 | 8.609 | 1.00 | 53.47 | 7 |
| ATOM | 1130 | C | ASN | C | 273 | −5.447 | 60.654 | 6.272 | 1.00 | 44.46 | 6 |
| ATOM | 1131 | O | ASN | C | 273 | −6.213 | 59.729 | 6.565 | 1.00 | 42.25 | 8 |
| ATOM | 1132 | N | LEU | C | 274 | −4.120 | 60.506 | 6.183 | 1.00 | 33.07 | 7 |
| ATOM | 1133 | CA | LEU | C | 274 | −3.513 | 59.186 | 6.407 | 1.00 | 37.06 | 6 |
| ATOM | 1134 | CB | LEU | C | 274 | −2.550 | 58.789 | 5.288 | 1.00 | 33.35 | 6 |
| ATOM | 1135 | CG | LEU | C | 274 | −3.171 | 58.526 | 3.908 | 1.00 | 36.17 | 6 |
| ATOM | 1136 | CD1 | LEU | C | 274 | −2.201 | 58.059 | 2.854 | 1.00 | 35.69 | 6 |
| ATOM | 1137 | CD2 | LEU | C | 274 | −4.292 | 57.498 | 4.023 | 1.00 | 42.68 | 6 |
| ATOM | 1138 | C | LEU | C | 274 | −2.827 | 59.212 | 7.772 | 1.00 | 35.03 | 6 |
| ATOM | 1139 | O | LEU | C | 274 | −2.224 | 58.213 | 8.172 | 1.00 | 39.17 | 8 |
| ATOM | 1140 | N | CYS | C | 275 | −3.049 | 60.262 | 8.549 | 1.00 | 34.81 | 7 |
| ATOM | 1141 | CA | CYS | C | 275 | −2.477 | 60.330 | 9.886 | 1.00 | 36.93 | 6 |
| ATOM | 1142 | C | CYS | C | 275 | −3.551 | 60.482 | 10.979 | 1.00 | 41.89 | 6 |
| ATOM | 1143 | O | CYS | C | 275 | −4.507 | 61.231 | 10.816 | 1.00 | 42.44 | 8 |
| ATOM | 1144 | CB | CYS | C | 275 | −1.450 | 61.458 | 9.952 | 1.00 | 37.22 | 6 |
| ATOM | 1145 | SG | CYS | C | 275 | 0.032 | 61.171 | 8.939 | 1.00 | 40.09 | 16 |
| ATOM | 1146 | N | PRO | C | 276 | −3.307 | 59.747 | 12.085 | 1.00 | 43.00 | 7 |
| ATOM | 1147 | CD | PRO | C | 276 | −2.168 | 58.833 | 12.246 | 1.00 | 46.79 | 6 |
| ATOM | 1148 | CA | PRO | C | 276 | −4.227 | 59.720 | 13.270 | 1.00 | 45.18 | 6 |
| ATOM | 1149 | CB | PRO | C | 276 | −3.501 | 58.834 | 14.281 | 1.00 | 43.00 | 6 |
| ATOM | 1150 | CG | PRO | C | 276 | −2.108 | 58.658 | 13.734 | 1.00 | 44.89 | 6 |
| ATOM | 1151 | C | PRO | C | 276 | −4.522 | 61.074 | 13.906 | 1.00 | 44.90 | 6 |
| ATOM | 1152 | O | PRO | C | 276 | −3.683 | 61.964 | 13.848 | 1.00 | 40.22 | 8 |
| ATOM | 1153 | N | SER | C | 277 | −5.702 | 61.239 | 14.523 | 1.00 | 49.31 | 7 |
| ATOM | 1154 | CA | SER | C | 277 | −6.057 | 62.560 | 15.080 | 1.00 | 53.44 | 6 |
| ATOM | 1155 | CB | SER | C | 277 | −7.590 | 62.750 | 15.034 | 1.00 | 61.29 | 6 |
| ATOM | 1156 | OG | SER | C | 277 | −7.984 | 63.864 | 15.817 | 1.00 | 59.45 | 8 |
| ATOM | 1157 | C | SER | C | 277 | −5.531 | 62.914 | 16.533 | 1.00 | 56.84 | 6 |
| ATOM | 1158 | O | SER | C | 277 | −6.323 | 63.093 | 17.457 | 1.00 | 58.71 | 8 |
| ATOM | 1159 | N | GLY | C | 278 | −4.196 | 63.036 | 16.701 | 1.00 | 72.91 | 7 |
| ATOM | 1160 | CA | GLY | C | 278 | −3.535 | 63.382 | 17.979 | 0.00 | 72.16 | 6 |
| ATOM | 1161 | C | GLY | C | 278 | −2.623 | 64.645 | 17.863 | 0.00 | 71.11 | 6 |
| ATOM | 1162 | O | GLY | C | 278 | −1.651 | 64.671 | 17.108 | 0.00 | 72.04 | 8 |
| ATOM | 1163 | N | GLY | C | 279 | −3.014 | 65.688 | 18.600 | 0.00 | 67.96 | 7 |
| ATOM | 1164 | CA | GLY | C | 279 | −2.296 | 66.962 | 18.676 | 0.00 | 66.01 | 6 |
| ATOM | 1165 | C | GLY | C | 279 | −0.889 | 66.636 | 19.187 | 0.00 | 61.41 | 6 |
| ATOM | 1166 | O | GLY | C | 279 | 0.045 | 67.424 | 19.020 | 0.00 | 60.21 | 8 |
| ATOM | 1167 | N | ASN | C | 280 | −0.768 | 65.439 | 19.816 | 0.00 | 43.63 | 7 |
| ATOM | 1168 | CA | ASN | C | 280 | 0.471 | 64.860 | 20.274 | 1.00 | 41.26 | 6 |
| ATOM | 1169 | CB | ASN | C | 280 | 0.281 | 63.676 | 21.248 | 1.00 | 51.58 | 6 |
| ATOM | 1170 | CG | ASN | C | 280 | 1.538 | 62.874 | 21.591 | 1.00 | 65.06 | 6 |
| ATOM | 1171 | OD1 | ASN | C | 280 | 2.201 | 63.121 | 22.603 | 1.00 | 62.58 | 8 |
| ATOM | 1172 | ND2 | ASN | C | 280 | 1.863 | 61.923 | 20.739 | 1.00 | 69.23 | 7 |
| ATOM | 1173 | C | ASN | C | 280 | 1.134 | 64.414 | 19.000 | 1.00 | 39.27 | 6 |
| ATOM | 1174 | O | ASN | C | 280 | 2.367 | 64.438 | 18.861 | 1.00 | 43.66 | 8 |
| ATOM | 1175 | N | ILE | C | 281 | 0.309 | 63.983 | 18.044 | 1.00 | 37.18 | 7 |
| ATOM | 1176 | CA | ILE | C | 281 | 0.909 | 63.540 | 16.783 | 1.00 | 39.37 | 6 |
| ATOM | 1177 | CB | ILE | C | 281 | −0.106 | 62.955 | 15.765 | 1.00 | 35.78 | 6 |
| ATOM | 1178 | CG2 | ILE | C | 281 | 0.541 | 62.824 | 14.398 | 1.00 | 53.65 | 6 |
| ATOM | 1179 | CG1 | ILE | C | 281 | −0.652 | 61.595 | 16.245 | 1.00 | 34.01 | 6 |
| ATOM | 1180 | CD1 | ILE | C | 281 | 0.391 | 60.510 | 16.337 | 1.00 | 39.13 | 6 |
| ATOM | 1181 | C | ILE | C | 281 | 1.619 | 64.698 | 16.132 | 1.00 | 37.32 | 6 |
| ATOM | 1182 | O | ILE | C | 281 | 2.790 | 64.607 | 15.753 | 1.00 | 37.87 | 8 |
| ATOM | 1183 | N | ILE | C | 282 | 0.906 | 65.826 | 16.001 | 1.00 | 29.62 | 7 |
| ATOM | 1184 | CA | ILE | C | 282 | 1.445 | 66.989 | 15.332 | 1.00 | 29.15 | 6 |
| ATOM | 1185 | CB | ILE | C | 282 | 0.318 | 68.006 | 15.057 | 1.00 | 29.10 | 6 |
| ATOM | 1186 | CG2 | ILE | C | 282 | 0.792 | 69.228 | 14.292 | 1.00 | 33.23 | 6 |
| ATOM | 1187 | CG1 | ILE | C | 282 | −0.887 | 67.372 | 14.382 | 1.00 | 37.23 | 6 |
| ATOM | 1188 | CD1 | ILE | C | 282 | −0.521 | 66.651 | 13.108 | 1.00 | 39.06 | 6 |
| ATOM | 1189 | C | ILE | C | 282 | 2.622 | 67.555 | 16.086 | 1.00 | 27.74 | 6 |

-continued

PDB FILE LISTING - cd811e1.pdb

| ATOM | 1190 | O   | ILE | C | 282 | 3.616  | 67.958 | 15.470 | 1.00 | 27.48 | 8  |
|------|------|-----|-----|---|-----|--------|--------|--------|------|-------|-----|
| ATOM | 1191 | N   | SER | C | 283 | 2.536  | 67.671 | 17.429 | 1.00 | 31.63 | 7  |
| ATOM | 1192 | CA  | SER | C | 283 | 3.632  | 68.234 | 18.186 | 1.00 | 28.41 | 6  |
| ATOM | 1193 | CB  | SER | C | 283 | 3.217  | 68.521 | 19.632 | 1.00 | 37.49 | 6  |
| ATOM | 1194 | OG  | SER | C | 283 | 3.292  | 67.403 | 20.469 | 1.00 | 52.68 | 8  |
| ATOM | 1195 | C   | SER | C | 283 | 4.900  | 67.401 | 18.084 | 1.00 | 30.27 | 6  |
| ATOM | 1196 | O   | SER | C | 283 | 6.003  | 67.938 | 18.285 | 1.00 | 30.36 | 8  |
| ATOM | 1197 | N   | ASN | C | 284 | 4.773  | 66.116 | 17.783 | 1.00 | 26.22 | 7  |
| ATOM | 1198 | CA  | ASN | C | 284 | 5.959  | 65.269 | 17.620 | 1.00 | 27.42 | 6  |
| ATOM | 1199 | CB  | ASN | C | 284 | 5.744  | 64.023 | 18.532 | 1.00 | 29.26 | 6  |
| ATOM | 1200 | CG  | ASN | C | 284 | 5.959  | 64.586 | 19.955 | 1.00 | 36.37 | 6  |
| ATOM | 1201 | OD1 | ASN | C | 284 | 7.018  | 65.179 | 20.173 | 1.00 | 34.52 | 8  |
| ATOM | 1202 | ND2 | ASN | C | 284 | 4.959  | 64.417 | 20.770 | 1.00 | 39.70 | 7  |
| ATOM | 1203 | C   | ASN | C | 284 | 6.060  | 64.717 | 16.192 | 1.00 | 22.07 | 6  |
| ATOM | 1204 | O   | ASN | C | 284 | 6.730  | 63.711 | 15.988 | 1.00 | 27.09 | 8  |
| ATOM | 1205 | N   | LEU | C | 285 | 5.436  | 65.408 | 15.232 | 1.00 | 25.57 | 7  |
| ATOM | 1206 | CA  | LEU | C | 285 | 5.477  | 64.935 | 13.835 | 1.00 | 24.22 | 6  |
| ATOM | 1207 | CB  | LEU | C | 285 | 5.021  | 66.064 | 12.899 | 1.00 | 28.37 | 6  |
| ATOM | 1208 | CG  | LEU | C | 285 | 5.034  | 65.744 | 11.397 | 1.00 | 27.69 | 6  |
| ATOM | 1209 | CD1 | LEU | C | 285 | 4.105  | 64.552 | 11.189 | 1.00 | 27.75 | 6  |
| ATOM | 1210 | CD2 | LEU | C | 285 | 4.488  | 66.992 | 10.655 | 1.00 | 24.39 | 6  |
| ATOM | 1211 | C   | LEU | C | 285 | 6.822  | 64.396 | 13.386 | 1.00 | 28.96 | 6  |
| ATOM | 1212 | O   | LEU | C | 285 | 6.917  | 63.272 | 12.850 | 1.00 | 26.23 | 8  |
| ATOM | 1213 | N   | PHE | C | 286 | 7.891  | 65.192 | 13.539 | 1.00 | 25.55 | 7  |
| ATOM | 1214 | CA  | PHE | C | 286 | 9.221  | 64.787 | 13.177 | 1.00 | 23.44 | 6  |
| ATOM | 1215 | CB  | PHE | C | 286 | 9.906  | 65.839 | 12.290 | 1.00 | 23.03 | 6  |
| ATOM | 1216 | CG  | PHE | C | 286 | 9.199  | 65.986 | 10.955 | 1.00 | 20.67 | 6  |
| ATOM | 1217 | CD1 | PHE | C | 286 | 8.607  | 67.187 | 10.626 | 1.00 | 23.30 | 6  |
| ATOM | 1218 | CD2 | PHE | C | 286 | 9.115  | 64.917 | 10.076 | 1.00 | 24.24 | 6  |
| ATOM | 1219 | CE1 | PHE | C | 286 | 7.950  | 67.339 | 9.417  | 1.00 | 28.29 | 6  |
| ATOM | 1220 | CE2 | PHE | C | 286 | 8.487  | 65.083 | 8.856  | 1.00 | 25.76 | 6  |
| ATOM | 1221 | CZ  | PHE | C | 286 | 7.926  | 66.293 | 8.495  | 1.00 | 25.94 | 6  |
| ATOM | 1222 | C   | PHE | C | 286 | 10.085 | 64.498 | 14.414 | 1.00 | 24.30 | 6  |
| ATOM | 1223 | O   | PHE | C | 286 | 11.143 | 63.917 | 14.225 | 1.00 | 28.00 | 8  |
| ATOM | 1224 | N   | LYS | C | 287 | 9.635  | 64.960 | 15.579 | 1.00 | 25.79 | 7  |
| ATOM | 1225 | CA  | LYS | C | 287 | 10.472 | 64.671 | 16.761 | 1.00 | 28.66 | 6  |
| ATOM | 1226 | CB  | LYS | C | 287 | 9.975  | 65.378 | 18.014 | 1.00 | 30.74 | 6  |
| ATOM | 1227 | CG  | LYS | C | 287 | 10.046 | 66.886 | 17.851 | 1.00 | 39.07 | 6  |
| ATOM | 1228 | CD  | LYS | C | 287 | 9.564  | 67.582 | 19.120 | 1.00 | 37.66 | 6  |
| ATOM | 1229 | CE  | LYS | C | 287 | 10.235 | 67.045 | 20.364 | 1.00 | 44.51 | 6  |
| ATOM | 1230 | NZ  | LYS | C | 287 | 9.589  | 67.630 | 21.579 | 1.00 | 51.78 | 7  |
| ATOM | 1231 | C   | LYS | C | 287 | 10.393 | 63.163 | 17.058 | 1.00 | 27.32 | 6  |
| ATOM | 1232 | O   | LYS | C | 287 | 11.378 | 62.681 | 17.638 | 1.00 | 32.08 | 8  |
| ATOM | 1233 | N   | GLU | C | 288 | 9.262  | 62.558 | 16.853 | 1.00 | 25.65 | 7  |
| ATOM | 1234 | CA  | GLU | C | 288 | 9.168  | 61.109 | 17.057 | 1.00 | 26.38 | 6  |
| ATOM | 1235 | CB  | GLU | C | 288 | 8.405  | 60.799 | 18.330 | 1.00 | 32.61 | 6  |
| ATOM | 1236 | CG  | GLU | C | 288 | 8.883  | 61.580 | 19.545 | 1.00 | 35.86 | 6  |
| ATOM | 1237 | CD  | GLU | C | 288 | 7.953  | 61.282 | 20.715 | 1.00 | 49.68 | 6  |
| ATOM | 1238 | OE1 | GLU | C | 288 | 7.772  | 62.105 | 21.631 | 1.00 | 55.75 | 8  |
| ATOM | 1239 | OE2 | GLU | C | 288 | 7.361  | 60.177 | 20.724 | 1.00 | 63.52 | 8  |
| ATOM | 1240 | C   | GLU | C | 288 | 8.424  | 60.477 | 15.876 | 1.00 | 24.79 | 6  |
| ATOM | 1241 | O   | GLU | C | 288 | 7.289  | 60.032 | 15.983 | 1.00 | 25.16 | 8  |
| ATOM | 1242 | N   | ASP | C | 289 | 9.125  | 60.434 | 14.753 | 1.00 | 26.85 | 7  |
| ATOM | 1243 | CA  | ASP | C | 289 | 8.568  | 59.980 | 13.508 | 1.00 | 24.56 | 6  |
| ATOM | 1244 | CB  | ASP | C | 289 | 9.369  | 60.684 | 12.398 | 1.00 | 25.50 | 6  |
| ATOM | 1245 | CG  | ASP | C | 289 | 10.715 | 60.115 | 12.072 | 1.00 | 27.35 | 6  |
| ATOM | 1246 | OD1 | ASP | C | 289 | 11.562 | 60.768 | 11.372 | 1.00 | 26.87 | 8  |
| ATOM | 1247 | OD2 | ASP | C | 289 | 11.060 | 58.983 | 12.489 | 1.00 | 26.73 | 8  |
| ATOM | 1248 | C   | ASP | C | 289 | 8.519  | 58.474 | 13.355 | 1.00 | 25.27 | 6  |
| ATOM | 1249 | O   | ASP | C | 289 | 8.888  | 57.761 | 14.315 | 1.00 | 24.29 | 8  |
| ATOM | 1250 | N   | CYS | C | 290 | 7.889  | 57.995 | 12.292 | 1.00 | 22.72 | 7  |
| ATOM | 1251 | CA  | CYS | C | 290 | 7.722  | 56.512 | 12.197 | 1.00 | 21.85 | 6  |
| ATOM | 1252 | C   | CYS | C | 290 | 9.039  | 55.781 | 12.183 | 1.00 | 23.09 | 6  |
| ATOM | 1253 | O   | CYS | C | 290 | 8.987  | 54.628 | 12.645 | 1.00 | 24.17 | 8  |
| ATOM | 1254 | CB  | CYS | C | 290 | 6.862  | 56.136 | 11.009 | 1.00 | 26.13 | 6  |
| ATOM | 1255 | SG  | CYS | C | 290 | 5.240  | 56.851 | 11.104 | 1.00 | 24.30 | 16 |
| ATOM | 1256 | N   | HIS | C | 291 | 10.181 | 56.308 | 11.712 | 1.00 | 21.89 | 7  |
| ATOM | 1257 | CA  | HIS | C | 291 | 11.421 | 55.547 | 11.830 | 1.00 | 19.74 | 6  |
| ATOM | 1258 | CB  | HIS | C | 291 | 12.547 | 56.294 | 11.070 | 1.00 | 25.39 | 6  |
| ATOM | 1259 | CG  | HIS | C | 291 | 12.326 | 56.132 | 9.596  | 1.00 | 23.25 | 6  |
| ATOM | 1260 | CD2 | HIS | C | 291 | 11.317 | 55.748 | 8.792  | 1.00 | 26.31 | 6  |
| ATOM | 1261 | ND1 | HIS | C | 291 | 13.423 | 56.382 | 8.784  | 1.00 | 27.59 | 7  |
| ATOM | 1262 | CE1 | HIS | C | 291 | 13.078 | 56.155 | 7.514  | 1.00 | 30.34 | 6  |
| ATOM | 1263 | NE2 | HIS | C | 291 | 11.831 | 55.757 | 7.489  | 1.00 | 25.82 | 7  |
| ATOM | 1264 | C   | HIS | C | 291 | 11.759 | 55.412 | 13.318 | 1.00 | 22.34 | 6  |
| ATOM | 1265 | O   | HIS | C | 291 | 12.280 | 54.354 | 13.735 | 1.00 | 25.37 | 8  |
| ATOM | 1266 | N   | GLN | C | 292 | 11.615 | 56.518 | 14.052 | 1.00 | 20.97 | 7  |

-continued

| | | | | PDB FILE LISTING - cd811e1.pdb | | | | | |
|---|---|---|---|---|---|---|---|---|---|
| ATOM | 1267 | CA | GLN | C | 292 | 11.899 | 56.386 | 15.511 | 1.00 | 21.60 | 6 |
| ATOM | 1268 | CB | GLN | C | 292 | 11.760 | 57.772 | 16.145 | 1.00 | 27.40 | 6 |
| ATOM | 1269 | CG | GLN | C | 292 | 12.000 | 57.661 | 17.656 | 1.00 | 28.40 | 6 |
| ATOM | 1270 | CD | GLN | C | 292 | 13.484 | 57.430 | 17.859 | 1.00 | 32.24 | 6 |
| ATOM | 1271 | OE1 | GLN | C | 292 | 14.393 | 58.103 | 17.336 | 1.00 | 39.00 | 8 |
| ATOM | 1272 | NE2 | GLN | C | 292 | 13.874 | 56.455 | 18.679 | 1.00 | 35.20 | 7 |
| ATOM | 1273 | C | GLN | C | 292 | 10.977 | 55.406 | 16.173 | 1.00 | 22.96 | 6 |
| ATOM | 1274 | O | GLN | C | 292 | 11.439 | 54.599 | 17.005 | 1.00 | 25.46 | 8 |
| ATOM | 1275 | N | LYS | C | 293 | 9.706 | 55.391 | 15.844 | 1.00 | 20.49 | 7 |
| ATOM | 1276 | CA | LYS | C | 293 | 8.766 | 54.437 | 16.454 | 1.00 | 24.11 | 6 |
| ATOM | 1277 | CB | LYS | C | 293 | 7.316 | 54.705 | 16.123 | 1.00 | 21.49 | 6 |
| ATOM | 1278 | CG | LYS | C | 293 | 6.906 | 56.132 | 16.541 | 1.00 | 20.82 | 6 |
| ATOM | 1279 | CD | LYS | C | 293 | 7.166 | 56.246 | 18.080 | 1.00 | 26.19 | 6 |
| ATOM | 1280 | CE | LYS | C | 293 | 6.380 | 57.510 | 18.465 | 1.00 | 31.71 | 6 |
| ATOM | 1281 | NZ | LYS | C | 293 | 6.412 | 57.682 | 19.953 | 1.00 | 43.53 | 7 |
| ATOM | 1282 | C | LYS | C | 293 | 9.094 | 52.995 | 16.091 | 1.00 | 24.90 | 6 |
| ATOM | 1283 | O | LYS | C | 293 | 9.021 | 52.081 | 16.925 | 1.00 | 25.35 | 8 |
| ATOM | 1284 | N | ILE | C | 294 | 9.502 | 52.769 | 14.834 | 1.00 | 23.01 | 7 |
| ATOM | 1285 | CA | ILE | C | 294 | 9.914 | 51.416 | 14.443 | 1.00 | 21.69 | 6 |
| ATOM | 1286 | CB | ILE | C | 294 | 10.149 | 51.365 | 12.898 | 1.00 | 20.45 | 6 |
| ATOM | 1287 | CG2 | ILE | C | 294 | 10.902 | 50.053 | 12.595 | 1.00 | 22.39 | 6 |
| ATOM | 1288 | CG1 | ILE | C | 294 | 8.826 | 51.424 | 12.182 | 1.00 | 22.59 | 6 |
| ATOM | 1289 | CD1 | ILE | C | 294 | 9.013 | 51.723 | 10.682 | 1.00 | 22.71 | 6 |
| ATOM | 1290 | C | ILE | C | 294 | 11.139 | 50.978 | 15.210 | 1.00 | 21.79 | 6 |
| ATOM | 1291 | O | ILE | C | 294 | 11.250 | 49.852 | 15.725 | 1.00 | 23.79 | 8 |
| ATOM | 1292 | N | ASP | C | 295 | 12.098 | 51.912 | 15.441 | 1.00 | 23.67 | 7 |
| ATOM | 1293 | CA | ASP | C | 295 | 13.281 | 51.560 | 16.213 | 1.00 | 23.07 | 6 |
| ATOM | 1294 | CB | ASP | C | 295 | 14.291 | 52.722 | 16.301 | 1.00 | 27.78 | 6 |
| ATOM | 1295 | CG | ASP | C | 295 | 15.082 | 52.938 | 15.034 | 1.00 | 37.31 | 6 |
| ATOM | 1296 | OD1 | ASP | C | 295 | 15.209 | 51.983 | 14.243 | 1.00 | 32.94 | 8 |
| ATOM | 1297 | OD2 | ASP | C | 295 | 15.570 | 54.098 | 14.872 | 1.00 | 41.42 | 8 |
| ATOM | 1298 | C | ASP | C | 295 | 12.825 | 51.240 | 17.666 | 1.00 | 23.22 | 6 |
| ATOM | 1299 | O | ASP | C | 295 | 13.357 | 50.303 | 18.289 | 1.00 | 26.53 | 8 |
| ATOM | 1300 | N | ASP | C | 296 | 11.931 | 52.047 | 18.194 | 1.00 | 23.58 | 7 |
| ATOM | 1301 | CA | ASP | C | 296 | 11.458 | 51.889 | 19.570 | 1.00 | 23.39 | 6 |
| ATOM | 1302 | CB | ASP | C | 296 | 10.529 | 53.012 | 20.025 | 1.00 | 27.78 | 6 |
| ATOM | 1303 | CG | ASP | C | 296 | 11.224 | 54.362 | 20.124 | 1.00 | 29.71 | 6 |
| ATOM | 1304 | OD1 | ASP | C | 296 | 12.461 | 54.427 | 20.176 | 1.00 | 31.37 | 8 |
| ATOM | 1305 | OD2 | ASP | C | 296 | 10.444 | 55.326 | 20.197 | 1.00 | 39.13 | 8 |
| ATOM | 1306 | C | ASP | C | 296 | 10.756 | 50.552 | 19.733 | 1.00 | 27.01 | 6 |
| ATOM | 1307 | O | ASP | C | 296 | 10.850 | 49.914 | 20.794 | 1.00 | 29.39 | 8 |
| ATOM | 1308 | N | LEU | C | 297 | 10.007 | 50.102 | 18.742 | 1.00 | 23.26 | 7 |
| ATOM | 1309 | CA | LEU | C | 297 | 9.314 | 48.820 | 18.800 | 1.00 | 26.92 | 6 |
| ATOM | 1310 | CB | LEU | C | 297 | 8.515 | 48.599 | 17.481 | 1.00 | 23.50 | 6 |
| ATOM | 1311 | CG | LEU | C | 297 | 7.865 | 47.206 | 17.409 | 1.00 | 25.96 | 6 |
| ATOM | 1312 | CD1 | LEU | C | 297 | 6.821 | 46.978 | 18.514 | 1.00 | 23.25 | 6 |
| ATOM | 1313 | CD2 | LEU | C | 297 | 7.209 | 47.043 | 16.056 | 1.00 | 30.08 | 6 |
| ATOM | 1314 | C | LEU | C | 297 | 10.319 | 47.700 | 18.994 | 1.00 | 22.60 | 6 |
| ATOM | 1315 | O | LEU | C | 297 | 10.238 | 46.833 | 19.871 | 1.00 | 25.36 | 8 |
| ATOM | 1316 | N | PHE | C | 298 | 11.370 | 47.704 | 18.181 | 1.00 | 22.46 | 7 |
| ATOM | 1317 | CA | PHE | C | 298 | 12.397 | 46.657 | 18.190 | 1.00 | 22.98 | 6 |
| ATOM | 1318 | CB | PHE | C | 298 | 13.146 | 46.534 | 16.828 | 1.00 | 21.20 | 6 |
| ATOM | 1319 | CG | PHE | C | 298 | 12.215 | 45.936 | 15.763 | 1.00 | 21.65 | 6 |
| ATOM | 1320 | CD1 | PHE | C | 298 | 11.603 | 46.775 | 14.851 | 1.00 | 23.88 | 6 |
| ATOM | 1321 | CD2 | PHE | C | 298 | 11.945 | 44.579 | 15.727 | 1.00 | 19.61 | 6 |
| ATOM | 1322 | CE1 | PHE | C | 298 | 10.711 | 46.287 | 13.918 | 1.00 | 23.10 | 6 |
| ATOM | 1323 | CE2 | PHE | C | 298 | 10.976 | 44.082 | 14.879 | 1.00 | 22.89 | 6 |
| ATOM | 1324 | CZ | PHE | C | 298 | 10.385 | 44.944 | 13.954 | 1.00 | 22.89 | 6 |
| ATOM | 1325 | C | PHE | C | 298 | 13.346 | 46.765 | 19.366 | 1.00 | 22.24 | 6 |
| ATOM | 1326 | O | PHE | C | 298 | 13.995 | 45.762 | 19.696 | 1.00 | 26.14 | 8 |
| ATOM | 1327 | N | SER | C | 299 | 13.452 | 47.932 | 19.987 | 1.00 | 25.90 | 7 |
| ATOM | 1328 | CA | SER | C | 299 | 14.264 | 48.166 | 21.163 | 1.00 | 27.99 | 6 |
| ATOM | 1329 | CB | SER | C | 299 | 14.694 | 49.677 | 21.208 | 1.00 | 28.04 | 6 |
| ATOM | 1330 | OG | SER | C | 299 | 15.551 | 49.835 | 20.076 | 1.00 | 48.85 | 8 |
| ATOM | 1331 | C | SER | C | 299 | 13.465 | 47.944 | 22.441 | 1.00 | 27.66 | 6 |
| ATOM | 1332 | O | SER | C | 299 | 14.116 | 47.914 | 23.506 | 1.00 | 33.14 | 8 |
| ATOM | 1333 | N | GLY | C | 300 | 12.146 | 47.836 | 22.389 | 1.00 | 25.96 | 7 |
| ATOM | 1334 | CA | GLY | C | 300 | 11.389 | 47.595 | 23.618 | 1.00 | 26.90 | 6 |
| ATOM | 1335 | C | GLY | C | 300 | 11.182 | 48.875 | 24.404 | 1.00 | 30.76 | 6 |
| ATOM | 1336 | O | GLY | C | 300 | 11.023 | 48.830 | 25.639 | 1.00 | 31.00 | 8 |
| ATOM | 1337 | N | LYS | C | 301 | 11.073 | 49.975 | 23.685 | 1.00 | 29.45 | 7 |
| ATOM | 1338 | CA | LYS | C | 301 | 10.905 | 51.285 | 24.343 | 1.00 | 33.22 | 6 |
| ATOM | 1339 | CB | LYS | C | 301 | 12.104 | 52.130 | 23.800 | 1.00 | 34.54 | 6 |
| ATOM | 1340 | CG | LYS | C | 301 | 13.438 | 51.692 | 24.356 | 1.00 | 45.39 | 6 |
| ATOM | 1341 | CD | LYS | C | 301 | 14.579 | 52.509 | 23.760 | 1.00 | 55.89 | 6 |
| ATOM | 1342 | CE | LYS | C | 301 | 15.883 | 52.152 | 24.454 | 1.00 | 63.37 | 6 |
| ATOM | 1343 | NZ | LYS | C | 301 | 15.809 | 50.819 | 25.114 | 1.00 | 64.44 | 7 |

-continued

PDB FILE LISTING - cd811e1.pdb

| | | | | | | | | | | |
|---|---|---|---|---|---|---|---|---|---|---|
| ATOM | 1344 | C   | LYS | C | 301 | 9.716   | 52.056 | 23.798  | 1.00 | 34.37 | 6 |
| ATOM | 1345 | O   | LYS | C | 301 | 9.632   | 53.265 | 24.050  | 1.00 | 41.72 | 8 |
| ATOM | 1346 | N   | HIS | C | 302 | 8.910   | 51.471 | 22.953  | 1.00 | 34.82 | 7 |
| ATOM | 1347 | CA  | HIS | C | 302 | 7.804   | 52.130 | 22.291  | 1.00 | 37.17 | 6 |
| ATOM | 1348 | CB  | HIS | C | 302 | 7.209   | 51.176 | 21.276  | 1.00 | 36.32 | 6 |
| ATOM | 1349 | CG  | HIS | C | 302 | 6.061   | 51.594 | 20.444  | 1.00 | 49.41 | 6 |
| ATOM | 1350 | CD2 | HIS | C | 302 | 5.233   | 52.660 | 20.480  | 1.00 | 59.81 | 6 |
| ATOM | 1351 | ND1 | HIS | C | 302 | 5.644   | 50.821 | 19.377  | 1.00 | 48.06 | 7 |
| ATOM | 1352 | CE1 | HIS | C | 302 | 4.594   | 51.386 | 18.808  | 1.00 | 59.89 | 6 |
| ATOM | 1353 | NE2 | HIS | C | 302 | 4.330   | 52.514 | 19.455  | 1.00 | 63.35 | 7 |
| ATOM | 1354 | C   | HIS | C | 302 | 6.748   | 52.610 | 23.267  | 1.00 | 38.73 | 6 |
| ATOM | 1355 | O   | HIS | C | 302 | 6.229   | 51.770 | 24.028  | 1.00 | 38.79 | 8 |
| ATOM | 1356 | OXT | HIS | C | 302 | 6.450   | 53.825 | 23.192  | 1.00 | 50.99 | 8 |
| ATOM | 1357 | OW  | WAT | W | 1   | −4.224  | 33.423 | 34.144  | 1.00 | 53.27 | 8 |
| ATOM | 1358 | OW  | WAT | W | 2   | 18.813  | 49.538 | 11.784  | 1.00 | 43.86 | 8 |
| ATOM | 1359 | OW  | WAT | W | 3   | 18.261  | 39.681 | 10.865  | 1.00 | 39.76 | 8 |
| ATOM | 1360 | OW  | WAT | W | 4   | 8.904   | 33.078 | 11.851  | 1.00 | 38.31 | 8 |
| ATOM | 1361 | OW  | WAT | W | 5   | 4.199   | 60.972 | 19.377  | 1.00 | 52.52 | 8 |
| ATOM | 1362 | OW  | WAT | W | 6   | 14.477  | 53.540 | 5.612   | 1.00 | 48.28 | 8 |
| ATOM | 1363 | OW  | WAT | W | 7   | 11.280  | 35.102 | −0.408  | 1.00 | 43.88 | 8 |
| ATOM | 1364 | OW  | WAT | W | 8   | 10.087  | 32.358 | 34.001  | 1.00 | 39.96 | 8 |
| ATOM | 1365 | OW  | WAT | W | 9   | 15.416  | 57.414 | 13.859  | 1.00 | 48.04 | 8 |
| ATOM | 1366 | OW  | WAT | W | 10  | 1.929   | 52.862 | 20.272  | 1.00 | 55.69 | 8 |
| ATOM | 1367 | OW  | WAT | W | 11  | 4.935   | 60.748 | 16.928  | 1.00 | 39.08 | 8 |
| ATOM | 1368 | OW  | WAT | W | 12  | −3.393  | 52.954 | −1.588  | 1.00 | 50.38 | 8 |
| ATOM | 1369 | OW  | WAT | W | 13  | −13.253 | 36.368 | 20.479  | 1.00 | 42.42 | 8 |
| ATOM | 1370 | OW  | WAT | W | 14  | 0.313   | 32.026 | 34.781  | 1.00 | 47.16 | 8 |
| ATOM | 1371 | OW  | WAT | W | 15  | −6.564  | 45.853 | 14.770  | 1.00 | 68.25 | 8 |
| ATOM | 1372 | OW  | WAT | W | 16  | 12.038  | 51.785 | 0.724   | 1.00 | 41.22 | 8 |
| ATOM | 1373 | OW  | WAT | W | 17  | 14.999  | 64.994 | 4.375   | 1.00 | 48.22 | 8 |
| ATOM | 1374 | OW  | WAT | W | 18  | 17.970  | 48.546 | 24.089  | 1.00 | 68.67 | 8 |
| ATOM | 1375 | OW  | WAT | W | 19  | 18.217  | 40.214 | 24.483  | 1.00 | 47.37 | 8 |
| ATOM | 1376 | OW  | WAT | W | 20  | 1.939   | 28.873 | 14.169  | 1.00 | 44.69 | 8 |
| ATOM | 1377 | OW  | WAT | W | 21  | 3.847   | 66.616 | −1.008  | 1.00 | 44.63 | 8 |
| ATOM | 1378 | OW  | WAT | W | 22  | −3.915  | 63.084 | 7.867   | 1.00 | 45.45 | 8 |
| ATOM | 1379 | OW  | WAT | W | 23  | 19.360  | 45.486 | 31.250  | 1.00 | 63.22 | 8 |
| ATOM | 1380 | OW  | WAT | W | 24  | 10.025  | 47.358 | 30.471  | 1.00 | 67.04 | 8 |
| ATOM | 1381 | OW  | WAT | W | 25  | 13.664  | 53.469 | 2.124   | 1.00 | 42.64 | 8 |
| ATOM | 1382 | OW  | WAT | W | 26  | −5.012  | 60.157 | −2.193  | 1.00 | 61.60 | 8 |
| ATOM | 1383 | OW  | WAT | W | 27  | 6.815   | 67.394 | 21.507  | 1.00 | 52.80 | 8 |
| ATOM | 1384 | OW  | WAT | W | 28  | 17.915  | 33.402 | 34.758  | 1.00 | 44.35 | 8 |
| ATOM | 1385 | OW  | WAT | W | 29  | 16.731  | 42.979 | 3.382   | 1.00 | 84.13 | 8 |
| ATOM | 1386 | OW  | WAT | W | 30  | −6.288  | 67.664 | 0.468   | 1.00 | 45.25 | 8 |
| ATOM | 1387 | OW  | WAT | W | 31  | 7.402   | 62.280 | 10.335  | 1.00 | 42.54 | 8 |
| ATOM | 1388 | OW  | WAT | W | 32  | 15.598  | 43.947 | 1.369   | 1.00 | 56.42 | 8 |
| ATOM | 1389 | OW  | WAT | W | 33  | −7.926  | 47.819 | 12.072  | 1.00 | 44.03 | 8 |
| ATOM | 1390 | OW  | WAT | W | 34  | 16.998  | 49.958 | 15.318  | 1.00 | 48.80 | 8 |
| ATOM | 1391 | OW  | WAT | W | 35  | 8.586   | 64.846 | 22.173  | 1.00 | 69.56 | 8 |
| ATOM | 1392 | OW  | WAT | W | 36  | −0.416  | 48.332 | 28.972  | 1.00 | 49.67 | 8 |
| ATOM | 1393 | OW  | WAT | W | 37  | −1.687  | 35.124 | 10.272  | 1.00 | 51.02 | 8 |
| ATOM | 1394 | OW  | WAT | W | 38  | 8.930   | 32.323 | 14.635  | 1.00 | 43.76 | 8 |
| ATOM | 1395 | OW  | WAT | W | 39  | 14.596  | 53.388 | 26.734  | 1.00 | 54.53 | 8 |
| ATOM | 1396 | OW  | WAT | W | 40  | −11.348 | 62.652 | 8.819   | 1.00 | 63.88 | 8 |
| ATOM | 1397 | OW  | WAT | W | 41  | 3.903   | 62.050 | 15.465  | 1.00 | 38.48 | 8 |
| ATOM | 1398 | OW  | WAT | W | 42  | −7.252  | 41.756 | 19.850  | 1.00 | 52.81 | 8 |
| ATOM | 1399 | OW  | WAT | W | 43  | −1.996  | 56.577 | 17.341  | 1.00 | 59.40 | 8 |
| ATOM | 1400 | OW  | WAT | W | 44  | 4.137   | 49.725 | 23.884  | 1.00 | 48.85 | 8 |
| ATOM | 1401 | OW  | WAT | W | 45  | 15.737  | 51.416 | 6.167   | 1.00 | 38.54 | 8 |
| ATOM | 1402 | OW  | WAT | W | 46  | −5.011  | 40.117 | 20.046  | 1.00 | 38.42 | 8 |
| ATOM | 1403 | OW  | WAT | W | 47  | −13.873 | 33.451 | 19.673  | 1.00 | 42.16 | 8 |
| ATOM | 1404 | OW  | WAT | W | 48  | 11.057  | 53.487 | −1.251  | 1.00 | 51.34 | 8 |
| ATOM | 1405 | OW  | WAT | W | 49  | 14.300  | 48.217 | 26.182  | 1.00 | 45.81 | 8 |
| ATOM | 1406 | OW  | WAT | W | 50  | 12.120  | 58.997 | −1.940  | 1.00 | 63.88 | 8 |
| ATOM | 1407 | OW  | WAT | W | 51  | −0.336  | 33.581 | 11.855  | 1.00 | 48.03 | 8 |
| ATOM | 1408 | OW  | WAT | W | 52  | 16.829  | 63.174 | 4.226   | 1.00 | 48.59 | 8 |
| ATOM | 1409 | OW  | WAT | W | 53  | 16.022  | 41.438 | 23.130  | 1.00 | 41.43 | 8 |
| ATOM | 1410 | OW  | WAT | W | 54  | −15.200 | 36.945 | 22.654  | 1.00 | 28.98 | 8 |
| ATOM | 1411 | OW  | WAT | W | 55  | 13.277  | 40.851 | 6.595   | 1.00 | 29.49 | 8 |
| ATOM | 1412 | OW  | WAT | W | 56  | 12.069  | 61.338 | 14.855  | 1.00 | 27.04 | 8 |
| ATOM | 1413 | OW  | WAT | W | 57  | 3.227   | 32.023 | 23.771  | 1.00 | 30.91 | 8 |
| ATOM | 1414 | OW  | WAT | W | 58  | 9.562   | 62.631 | 0.352   | 1.00 | 32.41 | 8 |
| ATOM | 1415 | OW  | WAT | W | 59  | 6.585   | 69.144 | 1.589   | 1.00 | 39.21 | 8 |
| ATOM | 1416 | OW  | WAT | W | 60  | 5.345   | 68.911 | −0.882  | 1.00 | 44.18 | 8 |
| ATOM | 1417 | OW  | WAT | W | 61  | −0.751  | 50.368 | 19.292  | 1.00 | 32.73 | 8 |
| ATOM | 1418 | OW  | WAT | W | 62  | 17.617  | 40.863 | 26.974  | 1.00 | 32.29 | 8 |
| ATOM | 1419 | OW  | WAT | W | 63  | 1.179   | 39.116 | 32.520  | 1.00 | 34.20 | 8 |
| ATOM | 1420 | OW  | WAT | W | 64  | −3.110  | 37.236 | 22.171  | 1.00 | 33.88 | 8 |

-continued

| | | PDB FILE LISTING - cd811e1.pdb | | | | | | | |
|---|---|---|---|---|---|---|---|---|---|
| ATOM | 1421 | OW | WAT | W | 65 | 14.044 | 57.099 | 4.209 | 1.00 | 33.65 | 8 |
| ATOM | 1422 | OW | WAT | W | 66 | 15.989 | 40.653 | 9.396 | 1.00 | 30.96 | 8 |
| ATOM | 1423 | OW | WAT | W | 67 | 5.371 | 35.579 | 5.640 | 1.00 | 34.67 | 8 |
| ATOM | 1424 | OW | WAT | W | 68 | −4.275 | 34.135 | 21.863 | 1.00 | 40.99 | 8 |
| ATOM | 1425 | OW | WAT | W | 69 | −10.323 | 38.406 | 25.608 | 1.00 | 36.01 | 8 |
| ATOM | 1426 | OW | WAT | W | 70 | −2.810 | 46.901 | 24.190 | 1.00 | 39.93 | 8 |
| ATOM | 1427 | OW | WAT | W | 71 | 13.870 | 64.852 | 12.989 | 1.00 | 34.39 | 8 |
| ATOM | 1428 | OW | WAT | W | 72 | 4.793 | 27.473 | 30.299 | 1.00 | 46.24 | 8 |
| ATOM | 1429 | OW | WAT | W | 73 | −15.971 | 32.066 | 20.578 | 1.00 | 38.92 | 8 |
| ATOM | 1430 | OW | WAT | W | 74 | 5.399 | 34.420 | 8.086 | 1.00 | 39.29 | 8 |
| ATOM | 1431 | OW | WAT | W | 75 | −0.519 | 32.450 | 14.342 | 1.00 | 33.68 | 8 |
| ATOM | 1432 | OW | WAT | W | 76 | 2.179 | 32.697 | 11.146 | 1.00 | 36.98 | 8 |
| ATOM | 1433 | OW | WAT | W | 77 | 10.170 | 56.080 | −0.241 | 1.00 | 39.89 | 8 |
| ATOM | 1434 | OW | WAT | W | 78 | 5.714 | 48.333 | 1.212 | 1.00 | 37.11 | 8 |
| ATOM | 1435 | OW | WAT | W | 79 | −4.290 | 33.857 | 16.226 | 1.00 | 37.36 | 8 |
| ATOM | 1436 | OW | WAT | W | 80 | 2.780 | 25.857 | 19.866 | 1.00 | 36.02 | 8 |
| ATOM | 1437 | OW | WAT | W | 81 | 12.798 | 43.202 | 2.474 | 1.00 | 34.74 | 8 |
| ATOM | 1438 | OW | WAT | W | 82 | −7.897 | 39.332 | 18.472 | 1.00 | 41.75 | 8 |
| ATOM | 1439 | OW | WAT | W | 83 | 16.117 | 44.618 | 21.247 | 1.00 | 31.97 | 8 |
| ATOM | 1440 | OW | WAT | W | 84 | 11.055 | 65.023 | 0.596 | 1.00 | 38.11 | 8 |
| ATOM | 1441 | OW | WAT | W | 85 | 12.824 | 45.673 | 3.486 | 1.00 | 33.54 | 8 |
| ATOM | 1442 | OW | WAT | W | 86 | 15.100 | 60.207 | 1.681 | 1.00 | 45.21 | 8 |
| ATOM | 1443 | OW | WAT | W | 87 | −4.960 | 50.919 | 0.707 | 1.00 | 47.99 | 8 |
| ATOM | 1444 | OW | WAT | W | 88 | 9.128 | 42.918 | 32.795 | 1.00 | 44.27 | 8 |
| ATOM | 1445 | OW | WAT | W | 89 | 9.762 | 58.054 | 20.187 | 1.00 | 47.67 | 8 |
| ATOM | 1446 | OW | WAT | W | 90 | 12.540 | 34.153 | 9.788 | 1.00 | 45.77 | 8 |
| ATOM | 1447 | OW | WAT | W | 91 | 17.905 | 51.635 | 10.678 | 1.00 | 40.67 | 8 |
| ATOM | 1448 | OW | WAT | W | 92 | −3.398 | 39.623 | 8.128 | 1.00 | 45.41 | 8 |
| ATOM | 1449 | OW | WAT | W | 93 | 6.924 | 42.895 | −0.650 | 1.00 | 42.91 | 8 |
| ATOM | 1450 | OW | WAT | W | 94 | 7.797 | 55.535 | 21.646 | 1.00 | 50.17 | 8 |
| ATOM | 1451 | OW | WAT | W | 95 | 12.822 | 64.411 | 2.584 | 1.00 | 37.53 | 8 |
| ATOM | 1452 | OW | WAT | W | 96 | 10.955 | 46.835 | −5.508 | 1.00 | 45.36 | 8 |
| ATOM | 1453 | OW | WAT | W | 97 | 13.257 | 59.487 | 9.888 | 1.00 | 36.34 | 8 |
| ATOM | 1454 | OW | WAT | W | 98 | 14.865 | 39.030 | 19.548 | 1.00 | 41.41 | 8 |
| ATOM | 1455 | OW | WAT | W | 99 | −2.138 | 41.902 | 25.462 | 1.00 | 41.60 | 8 |
| ATOM | 1456 | OW | WAT | W | 100 | −3.706 | 31.806 | 24.679 | 1.00 | 40.94 | 8 |
| ATOM | 1457 | OW | WAT | W | 101 | 5.836 | 33.167 | 1.082 | 1.00 | 43.31 | 8 |
| ATOM | 1458 | OW | WAT | W | 102 | 23.483 | 39.507 | 35.275 | 1.00 | 57.98 | 8 |
| ATOM | 1459 | OW | WAT | W | 103 | 17.559 | 63.021 | 7.407 | 1.00 | 50.25 | 8 |
| ATOM | 1460 | OW | WAT | W | 104 | 19.056 | 43.139 | 28.930 | 1.00 | 42.00 | 8 |
| ATOM | 1461 | OW | WAT | W | 105 | 19.572 | 41.453 | 18.032 | 1.00 | 45.63 | 8 |
| ATOM | 1462 | OW | WAT | W | 106 | 6.525 | 39.243 | −0.417 | 1.00 | 40.74 | 8 |
| ATOM | 1463 | OW | WAT | W | 107 | 3.627 | 31.518 | 12.831 | 1.00 | 38.63 | 8 |
| ATOM | 1464 | OW | WAT | W | 108 | 5.366 | 58.591 | 23.270 | 1.00 | 55.71 | 8 |
| ATOM | 1465 | OW | WAT | W | 109 | −0.088 | 26.458 | 16.764 | 1.00 | 52.60 | 8 |
| ATOM | 1466 | OW | WAT | W | 110 | 17.119 | 48.571 | −9.546 | 1.00 | 47.91 | 8 |
| ATOM | 1467 | OW | WAT | W | 111 | 1.096 | 44.692 | 2.583 | 1.00 | 40.04 | 8 |
| ATOM | 1468 | OW | WAT | W | 112 | 16.042 | 35.471 | 8.298 | 1.00 | 50.36 | 8 |
| ATOM | 1469 | OW | WAT | W | 113 | 12.648 | 35.159 | 33.701 | 1.00 | 39.34 | 8 |
| ATOM | 1470 | OW | WAT | W | 114 | 3.337 | 49.000 | −0.094 | 1.00 | 52.85 | 8 |
| ATOM | 1471 | OW | WAT | W | 115 | 20.033 | 39.068 | 22.889 | 1.00 | 58.35 | 8 |
| ATOM | 1472 | OW | WAT | W | 116 | 10.097 | 47.403 | 34.472 | 1.00 | 58.00 | 8 |
| ATOM | 1473 | OW | WAT | W | 117 | 10.830 | 41.416 | −3.209 | 1.00 | 41.27 | 8 |
| ATOM | 1474 | OW | WAT | W | 118 | 12.754 | 36.719 | 35.635 | 1.00 | 54.11 | 8 |
| ATOM | 1475 | OW | WAT | W | 119 | −0.813 | 31.338 | 21.906 | 1.00 | 46.66 | 8 |
| ATOM | 1476 | OW | WAT | W | 120 | 3.965 | 25.061 | 22.618 | 1.00 | 44.72 | 8 |
| ATOM | 1477 | OW | WAT | W | 121 | 13.777 | 59.149 | 13.305 | 1.00 | 41.18 | 8 |
| ATOM | 1478 | OW | WAT | W | 122 | 4.277 | 55.533 | 20.931 | 1.00 | 46.53 | 8 |
| ATOM | 1479 | OW | WAT | W | 123 | −7.345 | 30.636 | 20.890 | 1.00 | 46.01 | 8 |
| ATOM | 1480 | OW | WAT | W | 124 | 16.037 | 45.847 | −5.475 | 1.00 | 50.06 | 8 |
| ATOM | 1481 | OW | WAT | W | 125 | −3.061 | 47.338 | 18.259 | 1.00 | 41.61 | 8 |
| ATOM | 1482 | OW | WAT | W | 126 | 10.453 | 31.620 | 10.805 | 1.00 | 50.39 | 8 |
| ATOM | 1483 | OW | WAT | W | 127 | 17.496 | 40.971 | 20.796 | 1.00 | 55.25 | 8 |
| ATOM | 1484 | OW | WAT | W | 128 | −6.207 | 32.805 | 19.155 | 1.00 | 58.66 | 8 |
| ATOM | 1485 | OW | WAT | W | 129 | 16.601 | 45.869 | −1.260 | 1.00 | 59.55 | 8 |
| ATOM | 1486 | OW | WAT | W | 130 | 2.484 | 51.452 | 22.049 | 1.00 | 47.45 | 8 |
| ATOM | 1487 | OW | WAT | W | 131 | 11.516 | 67.657 | 23.120 | 1.00 | 55.77 | 8 |
| ATOM | 1488 | OW | WAT | W | 132 | 5.346 | 61.188 | 13.510 | 1.00 | 29.53 | 8 |
| ATOM | 1489 | OW | WAT | W | 133 | 13.484 | 40.850 | 3.961 | 1.00 | 38.04 | 8 |
| ATOM | 1490 | OW | WAT | W | 134 | 6.017 | 48.953 | 24.748 | 1.00 | 98.99 | 8 |
| ATOM | 1491 | OW | WAT | W | 135 | 12.715 | 45.073 | 31.090 | 1.00 | 47.26 | 8 |
| ATOM | 1492 | OW | WAT | W | 136 | 8.319 | 40.420 | −2.773 | 1.00 | 47.04 | 8 |
| ATOM | 1493 | OW | WAT | W | 137 | −8.731 | 32.859 | 33.302 | 1.00 | 49.10 | 8 |
| ATOM | 1494 | OW | WAT | W | 138 | 15.813 | 48.959 | 17.249 | 1.00 | 53.10 | 8 |
| ATOM | 1495 | OW | WAT | W | 139 | −15.705 | 39.364 | 21.958 | 1.00 | 63.55 | 8 |
| ATOM | 1496 | OW | WAT | W | 140 | −5.095 | 45.138 | 17.428 | 1.00 | 45.00 | 8 |
| ATOM | 1497 | OW | WAT | W | 141 | −13.312 | 30.683 | 20.947 | 1.00 | 53.07 | 8 |

-continued

| PDB FILE LISTING - cd811e1.pdb | | | | | | | | | |
|---|---|---|---|---|---|---|---|---|---|
| ATOM | 1498 | OW | WAT | W | 142 | −13.192 | 60.851 | 8.504 | 1.00 | 52.13 | 8 |
| ATOM | 1499 | OW | WAT | W | 143 | 23.328 | 40.686 | 16.795 | 1.00 | 47.26 | 8 |
| ATOM | 1500 | OW | WAT | W | 144 | 13.616 | 60.813 | 17.279 | 1.00 | 43.28 | 8 |
| ATOM | 1501 | OW | WAT | W | 145 | 12.017 | 47.329 | −3.100 | 1.00 | 48.09 | 8 |
| ATOM | 1502 | OW | WAT | W | 146 | 10.595 | 61.299 | −1.506 | 1.00 | 49.06 | 8 |
| ATOM | 1503 | OW | WAT | W | 147 | 8.027 | 61.147 | −4.069 | 1.00 | 52.20 | 8 |
| ATOM | 1504 | OW | WAT | W | 148 | −6.283 | 49.644 | 10.949 | 1.00 | 57.39 | 8 |
| ATOM | 1505 | OW | WAT | W | 149 | −9.469 | 40.692 | 26.922 | 1.00 | 43.53 | 8 |
| ATOM | 1506 | OW | WAT | W | 150 | 19.210 | 50.226 | 21.171 | 1.00 | 58.41 | 8 |
| ATOM | 1507 | OW | WAT | W | 151 | 2.611 | 26.546 | 15.184 | 1.00 | 50.95 | 8 |
| ATOM | 1508 | OW | WAT | W | 152 | 3.965 | 46.489 | −3.009 | 1.00 | 57.99 | 8 |
| ATOM | 1509 | OW | WAT | W | 153 | 16.271 | 55.882 | 11.030 | 1.00 | 48.24 | 8 |
| ATOM | 1510 | OW | WAT | W | 154 | 1.184 | 67.205 | −1.174 | 1.00 | 47.38 | 8 |
| ATOM | 1511 | OW | WAT | W | 155 | 2.482 | 46.558 | 0.974 | 1.00 | 67.17 | 8 |
| ATOM | 1512 | OW | WAT | W | 156 | 11.027 | 55.889 | 23.958 | 1.00 | 54.67 | 8 |
| ATOM | 1513 | OW | WAT | W | 157 | −4.446 | 30.923 | 22.181 | 1.00 | 62.18 | 8 |
| ATOM | 1514 | OW | WAT | W | 158 | −3.844 | 44.313 | 24.890 | 1.00 | 42.34 | 8 |
| ATOM | 1515 | OW | WAT | W | 159 | 14.549 | 53.163 | 20.560 | 1.00 | 49.30 | 8 |
| ATOM | 1516 | OW | WAT | W | 160 | −3.797 | 31.575 | 19.705 | 1.00 | 69.49 | 8 |
| ATOM | 1517 | OW | WAT | W | 161 | 6.756 | 25.504 | 17.575 | 1.00 | 49.43 | 8 |
| ATOM | 1518 | OW | WAT | W | 162 | 10.788 | 30.257 | 35.433 | 1.00 | 36.60 | 8 |
| ATOM | 1519 | OW | WAT | W | 163 | 21.237 | 50.223 | 9.133 | 1.00 | 56.25 | 8 |
| ATOM | 1520 | OW | WAT | W | 164 | −6.177 | 45.663 | 3.966 | 1.00 | 58.49 | 8 |
| ATOM | 1521 | OW | WAT | W | 165 | −1.644 | 33.990 | 22.144 | 1.00 | 32.61 | 8 |
| ATOM | 1522 | OW | WAT | W | 166 | 20.594 | 39.565 | 9.528 | 1.00 | 54.57 | 8 |
| ATOM | 1523 | OW | WAT | W | 167 | 15.964 | 59.646 | 9.793 | 1.00 | 50.70 | 8 |
| ATOM | 1524 | OW | WAT | W | 168 | 7.316 | 50.423 | 25.713 | 1.00 | 47.49 | 8 |
| ATOM | 1525 | OW | WAT | W | 169 | 23.295 | 32.789 | 15.200 | 1.00 | 57.39 | 8 |
| ATOM | 1526 | OW | WAT | W | 170 | −6.898 | 46.350 | 20.730 | 1.00 | 50.13 | 8 |
| ATOM | 1527 | OW | WAT | W | 171 | −8.760 | 52.976 | −3.940 | 1.00 | 55.95 | 8 |
| ATOM | 1528 | OW | WAT | W | 172 | −2.895 | 48.110 | 26.454 | 1.00 | 68.31 | 8 |
| ATOM | 1529 | OW | WAT | W | 173 | −1.144 | 71.221 | 17.499 | 1.00 | 50.95 | 8 |
| ATOM | 1530 | OW | WAT | W | 174 | 12.604 | 56.338 | 22.115 | 1.00 | 55.77 | 8 |
| ATOM | 1531 | OW | WAT | W | 175 | 22.778 | 50.987 | 6.750 | 1.00 | 51.42 | 8 |
| ATOM | 1532 | OW | WAT | W | 176 | 9.430 | 60.647 | −6.523 | 1.00 | 61.73 | 8 |
| ATOM | 1533 | OW | WAT | W | 177 | 15.767 | 60.697 | 14.713 | 1.00 | 61.57 | 8 |
| ATOM | 1534 | OW | WAT | W | 178 | 22.291 | 46.306 | 8.351 | 1.00 | 64.25 | 8 |
| ATOM | 1535 | OW | WAT | W | 179 | 14.393 | 57.247 | 1.565 | 1.00 | 50.53 | 8 |
| ATOM | 1536 | OW | WAT | W | 180 | 6.277 | 72.244 | 1.677 | 1.00 | 56.50 | 8 |
| ATOM | 1537 | OW | WAT | W | 181 | −5.357 | 56.977 | 16.549 | 1.00 | 63.38 | 8 |
| ATOM | 1538 | OW | WAT | W | 182 | 20.252 | 47.811 | 25.759 | 1.00 | 59.54 | 8 |
| ATOM | 1539 | OW | WAT | W | 183 | −0.767 | 65.909 | −2.025 | 1.00 | 59.74 | 8 |
| ATOM | 1540 | OW | WAT | W | 184 | 8.023 | 52.581 | −3.823 | 1.00 | 57.61 | 8 |
| ATOM | 1541 | OW | WAT | W | 185 | 22.973 | 31.298 | 13.186 | 1.00 | 61.46 | 8 |
| ATOM | 1542 | OW | WAT | W | 186 | 21.890 | 46.952 | 18.566 | 1.00 | 62.99 | 8 |
| ATOM | 1543 | OW | WAT | W | 187 | 12.545 | 56.301 | −0.180 | 1.00 | 62.12 | 8 |
| ATOM | 1544 | OW | WAT | W | 188 | 0.899 | 33.958 | 8.083 | 1.00 | 52.91 | 8 |
| ATOM | 1545 | OW | WAT | W | 189 | −4.871 | 46.670 | 29.841 | 1.00 | 66.19 | 8 |
| ATOM | 1546 | OW | WAT | W | 190 | −1.898 | 31.738 | 34.170 | 1.00 | 52.17 | 8 |
| ATOM | 1547 | OW | WAT | W | 191 | −1.189 | 41.151 | 2.866 | 1.00 | 53.86 | 8 |
| ATOM | 1548 | OW | WAT | W | 192 | 22.565 | 44.586 | 11.059 | 1.00 | 62.34 | 8 |
| ATOM | 1549 | OW | WAT | W | 193 | −5.244 | 44.118 | 13.781 | 1.00 | 60.66 | 8 |
| ATOM | 1550 | OW | WAT | W | 194 | 5.422 | 49.607 | −0.947 | 1.00 | 53.84 | 8 |
| END | | | | | | | | | | | |

The invention claimed is:

1. A method for modulating the ability of a tetraspanin protein to form a dimer with the wild-type tetraspanin, comprising the step of mutating at least one of the amino acids corresponding to human CD81 (SEQ ID NO:1) residues 114, 119, 123, 125, 126, 129, 142, 146, 149, 150, 153, 154, 197, 198, 199 and 200; wherein said mutated tetraspanin protein has a decreased ability to form a dimer with the wild-type tetraspanin.

2. The method of claim 1, wherein in the step of mutating at least one of the amino acids a non-polar residue is replaced by a polar residue.

3. The method of claim 1, wherein in the step of mutating at least one of the amino acids a non-polar residue is replaced by another non-polar residue.

4. The method of claim 1, wherein the tetraspanin is selected from the group consisting of CD9, TSPAN2, CD53, CD82, CD63, TALLA-1, and NET4.

5. The method of claim 4, wherein the tetraspanin is CD82.

6. The method of claim 4, wherein the tetraspanin is CD63.

7. A method for modulating the ability of a tetraspanin CD81 protein to form a dimer with a wild-type tetraspanin, comprising the step of mutating at least one of the amino acids corresponding to human CD81 (SEQ ID NO:1) residues 114, 119, 123, 125, 126, 129, 142, 146, 149, 150, 153, 154, 197, 198, 199 and 200; wherein said tetraspanin CD81 protein has a decreased ability to form a dimer with the wild-type tetraspanin.

8. A mutant tetraspanin protein which, compared with the wild-type protein, has a decreased ability to form a dimer with the wild-type protein.

9. The mutant tetraspanin of claim 8, wherein the mutant has a non-wild-type amino acid at one or more residues corresponding to human CD81 (SEQ ID NO:1) residues 114, 119, 123, 125, 126, 129, 142, 146, 149, 150, 153, 154, 197, 198, 199 and 200.

10. The mutant tetraspanin of claim 9, wherein the tetraspanin is selected from the group consisting of CD9, TSPAN2, CD53, CD82, CD63, TALLA-1, and NET4.

11. The method of claim 10, wherein the tetraspanin is CD82.

12. The method of claim 10, wherein the tetraspanin is CD63.

13. The mutant tetraspanin of claim 9, wherein the tetraspanin is CD81.

14. A tetraspanin dimer, wherein one or both of the monomers is a mutant tetraspanin according to any one of claims 8 to 13.

* * * * *